United States Patent
Olde et al.

(10) Patent No.: US 9,433,356 B2
(45) Date of Patent: Sep. 6, 2016

(54) DEVICES, A COMPUTER PROGRAM PRODUCT AND A METHOD FOR DATA EXTRACTION

(75) Inventors: Bo Olde, Lund (SE); Kristian Solem, Kavlinge (SE)

(73) Assignee: Gambro Lundia AB, Lund (SE)

( * ) Notice: Subject to any disclaimer, the term of this patent is extended or adjusted under 35 U.S.C. 154(b) by 1109 days.

(21) Appl. No.: 13/380,631

(22) PCT Filed: Jun. 24, 2010

(86) PCT No.: PCT/EP2010/058958
§ 371 (c)(1),
(2), (4) Date: Mar. 16, 2012

(87) PCT Pub. No.: WO2010/149726
PCT Pub. Date: Dec. 29, 2010

(65) Prior Publication Data
US 2012/0283581 A1 Nov. 8, 2012

Related U.S. Application Data

(66) Substitute for application No. 61/220,662, filed on Jun. 26, 2009.

(30) Foreign Application Priority Data

Jun. 26, 2009 (SE) .................................... 0900891

(51) Int. Cl.
| | |
|---|---|
| *A61B 5/02* | (2006.01) |
| *A61B 5/021* | (2006.01) |
| *A61B 5/08* | (2006.01) |
| *A61B 5/00* | (2006.01) |
| *A61M 1/36* | (2006.01) |

(52) U.S. Cl.
CPC ............... *A61B 5/02* (2013.01); *A61B 5/021* (2013.01); *A61B 5/0816* (2013.01);
(Continued)

(58) Field of Classification Search
CPC combination set(s) only.
See application file for complete search history.

(56) References Cited

U.S. PATENT DOCUMENTS

| | | |
|---|---|---|
| 3,882,861 A | 5/1975 | Kettering et al. |
| 3,946,731 A | 3/1976 | Lichtenstein |

(Continued)

FOREIGN PATENT DOCUMENTS

| | | |
|---|---|---|
| CN | 1662178 | 8/2005 |
| CN | 101010110 | 8/2007 |

(Continued)

OTHER PUBLICATIONS

Thermoregulation, Wikipedia https://en.wikipedia.org/wiki/Thermoregulation (Thermoregulation).*

(Continued)

*Primary Examiner* — Michael Kahelin
*Assistant Examiner* — Mitchell E Alter
(74) *Attorney, Agent, or Firm* — K&L Gates LLP

(57) ABSTRACT

A monitoring device receives a measurement signal obtained by a pressure sensor in an extracorporeal fluid system, such as an extracorporeal blood circuit for a dialysis machine which is in contact with a vascular system of a subject via a fluid connection. The monitoring device processes the measurement signal to identify pressure data that represents pulses originating from a first physiological phenomenon in the subject, excluding the heart of the subject. The first physiological phenomenon may be any of reflexes, voluntary muscle contractions, non-voluntary muscle contractions, a breathing system of the subject, an autonomous system of the subject for blood pressure regulation, or an autonomous system of the subject for body temperature regulation. The monitoring device may detect, present, track or predict a disordered condition of the subject using the pressure data, or monitor the integrity of the fluid connection based on the pressure data.

10 Claims, 29 Drawing Sheets

(52) U.S. Cl.
CPC .......... *A61B 5/4094* (2013.01); *A61B 5/4818* (2013.01); *A61M 1/3639* (2013.01); *A61B 5/0823* (2013.01); *A61B 5/411* (2013.01); *A61M 2205/3331* (2013.01); *A61M 2230/06* (2013.01); *A61M 2230/40* (2013.01); *A61M 2230/63* (2013.01)

(56) References Cited

U.S. PATENT DOCUMENTS

| | | | |
|---|---|---|---|
| 4,185,641 A | 1/1980 | Minior et al. | |
| 4,239,047 A | 12/1980 | Griggs, III et al. | |
| 4,277,227 A | 7/1981 | Jenkins | |
| 4,353,368 A | 10/1982 | Slovak et al. | |
| 4,392,847 A | 7/1983 | Whitney et al. | |
| 4,450,527 A | 5/1984 | Sramek | |
| 4,501,483 A | 2/1985 | Romansky et al. | |
| 4,534,756 A | 8/1985 | Nelson | |
| 4,541,282 A | 9/1985 | Auerweck et al. | |
| 4,648,869 A | 3/1987 | Bobo, Jr. | |
| 4,710,163 A | 12/1987 | Butterfield | |
| 4,828,543 A | 5/1989 | Weiss et al. | |
| 4,846,792 A | 7/1989 | Bobo, Jr. et al. | |
| 4,923,598 A | 5/1990 | Schal | |
| 4,959,050 A | 9/1990 | Bobo, Jr. | |
| 4,972,826 A | 11/1990 | Koehler et al. | |
| 4,979,940 A | 12/1990 | Bobo, Jr. et al. | |
| 4,981,467 A | 1/1991 | Bobo, Jr. et al. | |
| 5,026,348 A | 6/1991 | Venegas | |
| 5,100,374 A | 3/1992 | Kageyama | |
| 5,146,414 A | 9/1992 | McKown et al. | |
| 5,178,603 A | 1/1993 | Prince | |
| 5,243,990 A | 9/1993 | Aung et al. | |
| 5,311,871 A | 5/1994 | Yock | |
| 5,427,695 A | 6/1995 | Brown | |
| 5,557,263 A | 9/1996 | Fisher et al. | |
| 5,623,377 A | 4/1997 | Behrens et al. | |
| 5,693,008 A | 12/1997 | Brugger et al. | |
| 5,790,036 A | 8/1998 | Fisher et al. | |
| 5,830,365 A | 11/1998 | Schneditz | |
| 5,863,421 A | 1/1999 | Peter, Jr. et al. | |
| 5,910,252 A | 6/1999 | Truitt et al. | |
| 6,066,261 A | 5/2000 | Spickermann | |
| 6,071,421 A | 6/2000 | Brown | |
| 6,077,443 A | 6/2000 | Goldau | |
| 6,090,048 A * | 7/2000 | Hertz et al. | 600/485 |
| 6,167,765 B1 | 1/2001 | Weitzel | |
| 6,187,199 B1 | 2/2001 | Goldau | |
| 6,200,485 B1 | 3/2001 | Kitaevich et al. | |
| 6,221,040 B1 | 4/2001 | Kleinekofort | |
| 6,337,049 B1 | 1/2002 | Tamari | |
| 6,572,576 B2 | 6/2003 | Brugger et al. | |
| 6,575,927 B1 | 6/2003 | Weitzel et al. | |
| 6,595,942 B2 | 7/2003 | Kleinekofort | |
| 6,623,443 B1 | 9/2003 | Polaschegg | |
| 6,649,063 B2 | 11/2003 | Brugger et al. | |
| 6,663,585 B1 | 12/2003 | Ender | |
| 6,730,055 B2 | 5/2004 | Bainbridge et al. | |
| 6,736,789 B1 | 5/2004 | Spickermann | |
| 6,767,333 B1 | 7/2004 | Muller et al. | |
| 6,773,670 B2 | 8/2004 | Stringer et al. | |
| 6,780,159 B2 | 8/2004 | Sandler et al. | |
| 6,804,991 B2 | 10/2004 | Balschat et al. | |
| 6,827,698 B1 | 12/2004 | Kleinekofort | |
| 6,880,404 B2 | 4/2005 | Überreiter | |
| 6,899,691 B2 | 5/2005 | Bainbridge et al. | |
| 6,979,306 B2 | 12/2005 | Moll | |
| 7,040,142 B2 | 5/2006 | Burbank | |
| 7,060,047 B2 | 6/2006 | Lodi et al. | |
| 7,087,033 B2 | 8/2006 | Brugger et al. | |
| 7,169,352 B1 | 1/2007 | Felt et al. | |
| 7,172,569 B2 | 2/2007 | Kleinekofort | |
| 7,172,570 B2 | 2/2007 | Cavalcanti et al. | |
| 7,276,041 B2 | 10/2007 | Moll | |
| 7,410,473 B2 | 8/2008 | Levin et al. | |
| 7,537,687 B2 | 5/2009 | Toyoda et al. | |
| 7,615,028 B2 | 11/2009 | O'Mahony | |
| 8,152,751 B2 | 4/2012 | Roger et al. | |
| 8,197,421 B2 | 6/2012 | Freeman et al. | |
| 8,603,020 B2 | 12/2013 | Roger et al. | |
| 2001/0007930 A1 | 7/2001 | Kleinekofort | |
| 2002/0004636 A1 | 1/2002 | Tsubata | |
| 2002/0198483 A1 | 12/2002 | Wariar et al. | |
| 2003/0006175 A1* | 1/2003 | Kawaguchi | 210/87 |
| 2003/0009123 A1 | 1/2003 | Brugger et al. | |
| 2003/0128125 A1 | 7/2003 | Burbank et al. | |
| 2003/0130607 A1 | 7/2003 | Delnevo et al. | |
| 2003/0152482 A1 | 8/2003 | O'Mahony et al. | |
| 2004/0030277 A1 | 2/2004 | O'Mahony et al. | |
| 2004/0041792 A1 | 3/2004 | Criscione | |
| 2004/0171977 A1 | 9/2004 | Paolini et al. | |
| 2004/0186409 A1 | 9/2004 | Cavalcanti et al. | |
| 2004/0210144 A1 | 10/2004 | Amano et al. | |
| 2004/0228760 A1 | 11/2004 | Stringer et al. | |
| 2005/0004502 A1 | 1/2005 | O'Mahony et al. | |
| 2005/0010118 A1* | 1/2005 | Toyoda et al. | 600/486 |
| 2005/0051472 A1 | 3/2005 | Chionh et al. | |
| 2005/0131332 A1 | 6/2005 | Kelly et al. | |
| 2005/0230313 A1 | 10/2005 | O'Mahony et al. | |
| 2006/0047193 A1 | 3/2006 | Zhang | |
| 2006/0081517 A1 | 4/2006 | Toyoda et al. | |
| 2006/0122552 A1 | 6/2006 | O'Mahony | |
| 2007/0004996 A1 | 1/2007 | Lovejoy et al. | |
| 2007/0004997 A1 | 1/2007 | Felt et al. | |
| 2007/0010779 A1 | 1/2007 | Utterberg et al. | |
| 2007/0078368 A1 | 4/2007 | Felt et al. | |
| 2007/0093774 A1 | 4/2007 | Felt et al. | |
| 2007/0108128 A1 | 5/2007 | Kopperschmidt et al. | |
| 2007/0112289 A1 | 5/2007 | Cavalcanti et al. | |
| 2007/0179433 A1 | 8/2007 | Jonsson et al. | |
| 2007/0232980 A1 | 10/2007 | Felt et al. | |
| 2007/0276270 A1 | 11/2007 | Tran | |
| 2008/0015486 A1 | 1/2008 | Zhang et al. | |
| 2008/0077072 A1 | 3/2008 | Keenan et al. | |
| 2008/0108930 A1 | 5/2008 | Weitzel et al. | |
| 2008/0171960 A1 | 7/2008 | Brieske et al. | |
| 2008/0183120 A1 | 7/2008 | Utterberg et al. | |
| 2008/0195022 A1 | 8/2008 | Lucke et al. | |
| 2008/0214979 A1 | 9/2008 | Brugger et al. | |
| 2010/0004552 A1 | 1/2010 | Zhang et al. | |
| 2010/0168925 A1 | 7/2010 | Hilgers et al. | |
| 2012/0095381 A1 | 4/2012 | Tonelli | |
| 2013/0006130 A1 | 1/2013 | Olde et al. | |

FOREIGN PATENT DOCUMENTS

| | | |
|---|---|---|
| CN | 101466419 | 6/2009 |
| DE | 196 09 698 | 9/1997 |
| DE | 198 48 235 | 3/2000 |
| EP | 0 121 931 | 10/1984 |
| EP | 0 232 599 | 8/1987 |
| EP | 0 248 633 A2 | 12/1987 |
| EP | 0 300 315 | 1/1989 |
| EP | 0 332 330 | 9/1989 |
| EP | 0 361 793 | 4/1990 |
| EP | 0 895 787 | 2/1999 |
| EP | 1 273 315 A1 | 1/2003 |
| EP | 1 472 973 | 11/2004 |
| EP | 1 666 078 A2 | 6/2006 |
| EP | 1 736 185 | 12/2006 |
| JP | 60-232168 | 11/1985 |
| JP | 2-7938 | 1/1990 |
| JP | 10-328148 | 12/1998 |
| JP | 11104233 | 4/1999 |
| JP | 2005-027800 | 2/2005 |
| JP | 2005040518 | 2/2005 |
| JP | 2005-233681 | 9/2005 |
| JP | 2006/110118 | 4/2006 |
| JP | 2006/110120 | 4/2006 |
| JP | 2008-295517 | 12/2008 |
| WO | WO 91/00113 | 1/1991 |
| WO | 97/10013 A1 | 3/1997 |
| WO | WO 99/29356 | 6/1999 |
| WO | WO 00/18451 | 4/2000 |
| WO | 02053025 | 7/2002 |

(56) References Cited

FOREIGN PATENT DOCUMENTS

| WO | WO 02/102441 | 12/2002 |
|----|--------------|---------|
| WO | WO 03/002174 | 1/2003 |
| WO | WO 03/006944 | 1/2003 |
| WO | WO 03/058567 | 1/2003 |
| WO | WO 03/058608 | 1/2003 |
| WO | WO 2005/019416 | 3/2005 |
| WO | 2005/062973 | 7/2005 |
| WO | WO 2006/122001 | 11/2006 |
| WO | 2009/156174 | 12/2009 |
| WO | 2009/156175 | 12/2009 |
| WO | 98/20918 A1 | 12/2011 |

OTHER PUBLICATIONS

Vasoconstriction, Wikipedia https://en.wikipedia.org/wiki/Vasoconstriction (Vasoconstriction).*
Swedish Patent Application No. 0800890-6, filed Apr. 17, 2008.
U.S. Appl. No. 61/045,642, filed Apr. 17, 2008.
Wabel et al., Ansatze zur Identifikation von Patientenparametern während der Hamodialysetherapie, Identification of Patient Parameters during Hemodialysis, vol. 50, Issue May 2002 pp. 220-227 ISSN (Print) 0178-2312, Published Online Sep. 25, 2009—English Translation—11 pages.
Office Action issued in CN application 201510095301.1, mailed May 5, 2016, 12 pages.

* cited by examiner

DEVICES, A COMPUTER PROGRAM PRODUCT AND A METHOD FOR DATA EXTRACTION

RELATED APPLICATION

This application is the US national phase of international application PCT/EP2010/058958 filed 24 Jun. 2010 which designates the U.S. and claims priority to SE Application No. 0900891-3 filed 26 Jun. 2009 and U.S. Application No. 61/220,662 filed 26 Jun. 2009, the entire contents of each of which is hereby incorporated by reference.

BACKGROUND OF THE INVENTION

1. Technical Field

The present invention generally relates to extraction of data originating from a physiological phenomenon in a subject, in particular when the vascular system of the subject is in connection with an extracorporeal fluid system. The present invention is e.g. applicable in arrangements for extracorporeal blood treatment.

2. Background Art

Vital signs are measures of various physiological statistics often taken by health professionals in order to assess body functions. Vital signs of a subject, e.g. heart rate, blood pressure, oxygen saturation, electrocardiography (ECG), respiratory rate and autonomous regulation, such as blood pressure and body temperature, may be measured, monitored and interpreted to detect various disorders of the patient, for instance respiratory and heart related disorders. Typical equipment used for retrieving the vital signs includes a thermometer, a pulse oximeter, a capnograph and a pulse watch. Though a pulse may often be taken manually, a stethoscope may be required for a subject with a weak pulse.

With external vital sign monitors, such as a thermometer, a stethoscope, a photoplethysmograph (PPG), a pulse oximeter or a capnograph, it is possible to measure pulse, oxygen saturation and information on respiration, such as breathing rate and carbon-dioxide concentration in breath of patient.

Patients with kidney function insufficiency often suffer from various other disorders, for instance sleep apnea, periodic breathing and hyperventilation, making monitoring of vital signs of renal patients particularly important. Sleep apnea for instance, is a common disorder in the general population where 2%-25% suffer from it, and it correlates with increased rate of several co-morbidities, such as hypertension, coronary artery disease, arrhythmias, heart failure and stroke. The prevalence of apnea is even higher in the dialysis population where 30% to 80% of dialysis patients suffer from this problem. The reason for this is not clear, but it is believed that hypervolemia and high levels of uremic toxins may worsen the disorder. In addition, many dialysis patients (40%) are diagnosed with heart conditions such as angina pectoris, left ventricular hypertrophy, stroke or congestive heart failure. These patients and other subjects may also suffer from reflex-controlled phenomena, such as vomiting, coughing and hiccups. Hence, there is a particular need to monitor vital signs of patients with kidney function insufficiency.

The origin behind the vital signs are for instance physiological pulse generators, such as the breathing system, the autonomous system for blood pressure regulation and the autonomous system for body temperature regulation, which give rise to cyclic physiological phenomena which are known to cause variations in the blood pressure of a patient.

Blood pressure regulation is part of the complex regulatory system which controls arterial blood pressure and is dependent on sensory inputs related to cardiac output, peripheral resistance to blood flow at the arterioles, the viscosity of the blood, the volume of blood in the arterial system, the elasticity of the arterial walls, etc. Changes in blood pressure are brought about by the control exerted on the same physiological mechanisms.

The signals from which information regarding the vital signs are extracted and the sensors being used may vary and instruments for providing this information is often limited in purpose and functionality. Additionally, measurements of vital signs are often time consuming and require involvement and attention from staff competent in handling each instrument.

It is known, for instance from U.S. Pat. No. 5,243,990, of blood pressure monitors, even ones that are included in dialysis machine systems, that allow measurement of the patient's pulse and blood pressure values (e.g. systolic and diastolic pressure) at specified intervals.

To get a good picture of body functions, it is often desirable to monitor a plurality of vital signs, requiring a number of specialised sensors or monitors connected to the body of a patient, which is costly, cumbersome and distracting.

It is also known that coughing and sneezing may influence physiological measurements obtained from instruments. Coughing may for instance introduce errors in the PPG signal e.g. measured with a pulse oximeter.

Hence, there is a need for alternative and/or improved ways of monitoring vital signs for detecting, presenting, tracking and/or predicting disorders, such as disorders related to the respiratory, vascular and autonomous system of the subject.

Furthermore, in extracorporeal blood treatment, blood is taken out of a patient, treated and then reintroduced into the patient by means of an extracorporeal blood flow circuit. Generally, the blood is circulated through the circuit by one or more pumping devices. The circuit is connected to a blood vessel access of the patient, typically via one or more access devices, such as needles or venous catheters, which are inserted into the blood vessel access. Such extracorporeal blood treatments include hemodialysis, hemodiafiltration, hemofiltration, plasmapheresis, etc.

In extracorporeal blood treatment, it is vital to minimize the risk for malfunctions in the extracorporeal blood flow circuit, since these may lead to a potentially life-threatening condition of the patient. Serious conditions may arise if the extracorporeal blood flow circuit is disrupted, e.g. by an access device for blood extraction (e.g. an arterial needle) coming loose from the blood vessel access, causing air to be sucked into the circuit, or by an access device for blood reintroduction (e.g. a venous needle) coming loose from the blood vessel access, causing the patient to be drained of blood within minutes. Other malfunctions may be caused by the blood vessel access becoming blocked or obstructed, or by the access device being positioned too close to the walls of the blood vessel.

In WO 97/10013, the monitoring involves filtering a measured pressure signal to remove the frequency components that originate from a blood pump, and then detecting the heart signal by analysing the filtered pressure signal. The amplitude of the filtered pressure signal is then taken as an indication of the integrity of the fluid connection. This monitoring technique requires proper filtering and might thus fail if there is a significant frequency overlap between the heart signal and the pulses from the blood pump.

Hence, there is also a need for alternative and/or improved ways of monitoring the integrity of a fluid connection between an extra-corporeal circuit and a vascular system of a subject.

BRIEF SUMMARY OF THE INVENTION

One object of an embodiment of the invention is to provide an alternative or complementary technique for monitoring vital signs of a human or animal subject.

Another object of an embodiment of the invention is to provide an alternative or complementary technique for monitoring the integrity of the fluid connection between the extracorporeal and vascular systems, and also preferably with an improved robustness and/or an increased certainty of detecting a malfunction in the fluid connection.

These and other objects, which will appear from the description below, are at least partly achieved by means of devices, a method and a computer program product according to the independent claims, embodiments thereof being defined by the dependent claims.

Embodiments of the invention are based on the insight that these objects may be achieved by processing measurement signals from pressure sensors in an extracorporeal fluid system in contact with a vascular system of a subject, which signals previously have not been considered possible to extract and/or interpret and which signals now have been found to contain valuable information. Thus, embodiments of the invention enable monitoring of vital signs of a human or animal subject by processing a measurement signal obtained in a pressure measurement, the measurement signal being retrieved from a fluid system external of the subject, i.e. an extracorporeal fluid system, and connected to a vascular system of the subject. Correspondingly, embodiments of the invention enable monitoring of the integrity of a fluid connection between the extracorporeal fluid system and the vascular system of a subject, by processing such a measurement signal.

Embodiments of the invention may, e.g., be used in connection with blood treatment such as dialysis in various forms.

A first aspect of an embodiment of the invention is a device for processing a measurement signal obtained by a pressure sensor in an extracorporeal fluid system connected to a vascular system of a subject, said device comprising: means for receiving the measurement signal; and means for processing the measurement signal for identification of pressure data originating from a first physiological phenomenon in said subject, said physiological phenomenon excluding the heart of said subject.

A second aspect of an embodiment of the invention is a method for processing a measurement signal obtained by a pressure sensor in an extracorporeal fluid system connected to a vascular system of a subject, said method comprising: receiving the measurement signal; and processing the measurement signal for identification of pressure data originating from a first physiological phenomenon in said subject, said physiological phenomenon excluding the heart of said subject.

A third aspect of an embodiment of the invention is a computer program product comprising instructions for causing a computer to perform the method according to the second aspect.

A fourth aspect of an embodiment of the invention is a device for processing a measurement signal obtained by a pressure sensor in an extracorporeal fluid system connected to a vascular system of a subject, said device comprising: an input for receiving the measurement signal; and a signal processor connected to said input and configured to process the measurement signal for identification of pressure data originating from a first physiological phenomenon in said subject, excluding the heart of said subject.

According to these aspects, pressure data from a first physiological phenomenon in the subject, excluding the heart of the subject, is identified in the measurement signal. The first physiological phenomenon may be reflexes in the subject, voluntary or non-voluntary muscle contractions in the subject, the breathing system in the subject, the autonomous system of the subject for blood pressure regulation, or the autonomous system of the subject for body temperature regulation.

The first physiological phenomenon generates one or more pressure waves that propagate from the vascular system via the fluid connection into the extracorporeal fluid system to the pressure sensor, which is in direct or indirect hydrostatic contact with the fluid (e.g. blood) in the extracorporeal fluid system. The pressure sensor generates a pressure pulse for each pressure wave. A "pulse" is thus a set of data samples that define a local increase or decrease (depending on implementation) in signal magnitude within the time-dependent measurement signal. It is to be understood that the pressure sensor may receive pressure waves from other pulse generators, e.g. the heart of the subject and/or a mechanical pulse generator in the extracorporeal fluid system, and that these pressure waves also generate pressure pulses in the measurement signal.

Generally, the identified pressure data represents one or more pulses in the measurement signal that originate from the first physiological phenomenon. However, the pressure data may take many different forms.

In one variant, the pressure data is a parameter value which is extracted directly from the measurement signal. As noted above, the measurement signal may not only include one or more relevant pulses from the first physiological phenomenon, but may also include other pulse signals such as pulses from the heart of the subject, pulses from a mechanical pulse generator in the extracorporeal fluid system, as well as pulses from other physiological phenomena in the subject. However, in certain embodiments, it may be possible to calculate a parameter value that represents the relevant pulses from the first physiological phenomenon in the measurement signal.

In another variant, the pressure data is a time-dependent monitoring signal, which is obtained by processing the measurement signal to improve/facilitate identification of the relevant pulses from the first physiological phenomenon, either in the time domain or in the frequency domain. For example, the processing may result in a significant suppression or even elimination of unwanted or interfering signals in the measurement signal. Such unwanted signals may include pulses from the mechanical pulse generator and/or pulses from the heart of the subject and/or pulses from other physiological phenomena in the subject. After this processing, one or more relevant pulses have been extracted from or "isolated in" the measurement signal. As used herein, "to isolate relevant pulses" indicates that the measurement signal is processed to such an extent that the pulses that originate from the first physiological phenomenon can be detected and analyzed in the identified pressure data. The measurement signal may be processed to at least significantly exclude the heart pulses and/or to at least significantly exclude other unwanted signals, such as the pulses that originate from the mechanical pulse generator. For example, the measurement signal may be low-pass filtered to remove frequencies above about 0.4, 0.45, 0.5, 0.55, 0.6, 0.65, 0.7, 0.75 or 0.8 Hz. In another example, the measurement signal may be band-pass filtered in at least one of the frequency ranges about 0.15 Hz to about 0.4 Hz, about 0.04 Hz to about 0.15 Hz, and about 0.001 Hz to about 0.1 Hz. In yet another example, the measurement signal is high-pass filtered to at least remove frequencies below about 3-5 Hz, and preferably below about 3.5-4 Hz, e.g. to isolate pulses originating from fast muscle contractions, movements and sounds from abdomen and bowels, the subject speaking, etc. It is to be understood that "to isolate relevant pulses" need not exclude that the monitoring signal includes pulses from one or more further physiological phenomena, other than the heart, in the subject. However, in certain embodiments, the monitoring signal may indeed be generated substantially with signal components only from the first physiological phenomenon.

In yet another variant, the pressure data is a parameter value which is extracted from the above-mentioned monitoring signal.

After its identification, the pressure data may be processed or used for the purpose of detecting and/or presenting and/or tracking and/or predicting a disordered condition of the subject. Alternatively or additionally, the pressure data may be processed or used for the purpose of determining the integrity of the fluid connection.

Embodiments of the present invention apply to processing of measurement signals both off-line and on-line, i.e. both during, e.g. concurrently, and subsequent to a treatment, such as dialysis, as well as separated from such a treatment. The measurement signal may comprise raw data or pre-processed data, for instance filtered for signal noise reduction. Embodiments of the present invention are applicable to conditions involving particular sources of signal noise and artefacts, such as a running pump. The processing may for instance involve pre-processing including general signal filtration, removal of particular signal noise (typically measurement noise) and signal artefacts, such as from a running pump, and signal analysis. Embodiments of the present invention are also flexible in advantageously allowing continuous as well as intermittent measurements.

As an advantage of embodiments of the present invention, continuous or intermittent measurements of respiration and autonomic regulation, such as blood pressure regulation and temperature regulation, may be provided directly from the extra-corporeal circulation during e.g. dialysis treatment. Thus, a plurality of vital signs can be monitored simultaneously and continuously using a time-dependent pressure signal from the extra-corporeal circulation, and the need to attach a number of specialised sensors or monitors the body of the subject is reduced.

Embodiments of the invention may be beneficial for unattended patients, e.g. patients performing dialysis at home or nocturnal patients with limited staffing.

Embodiments of the invention also enable monitoring of the integrity of the fluid connection between the extracorporeal fluid system and the vascular system irrespective of any frequency overlap between the heart pulses and the pulses from mechanical pulse generators in the extracorporeal fluid system. For example, the monitoring may be based on pulses originating from a physiological phenomenon, other than the heart, that are shifted in frequency and/or time from pulses originating from the mechanical pulse generators.

Still other objectives, features, aspects and advantages of the present invention will appear from the following detailed description, from the attached claims as well as from the drawings and appendixes.

BRIEF DESCRIPTION OF THE DRAWINGS

Embodiments of the inventive concepts will now be described in more detail with reference to the accompanying schematic drawings.

DETAILED DESCRIPTION OF THE INVENTION

In the following, embodiments will be described with reference to fluid containing systems in general, and in relation to an extracorporeal blood flow circuit in particular. Thereafter, physiological phenomena and embodiments for extracting signals indicative of such physiological phenomena will be described. Then, exemplary embodiments for detecting disorders based on such extracted signals are described, as well as exemplary embodiments for monitoring the integrity of a fluid connection based on such extracted signals.

Throughout the following description, like elements are designated by the same reference signs.

GENERAL

Figure 1:
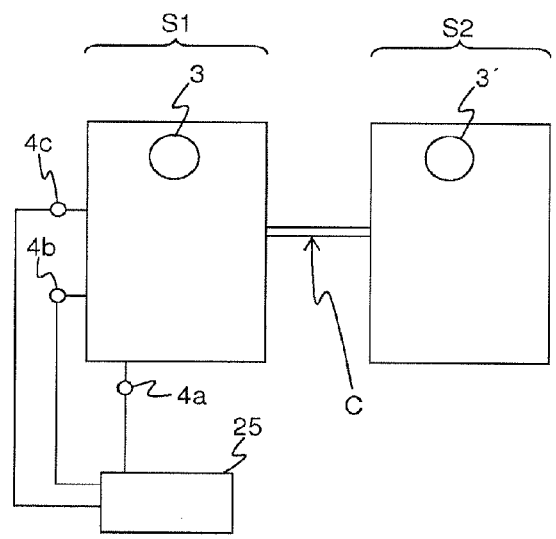
FIG. 1 is a schematic view of a general fluid containing system in which inventive data processing may be used for filtering a pressure signal.

FIG. 1 illustrates a general fluid arrangement in which a fluid connection C is established between a first fluid containing system S1 and a second fluid containing system S2. The fluid connection C may or may not transfer fluid from one system to the other. A first pulse generator 3 is arranged to generate a series of pressure waves in the fluid within the first system S1, and a second pulse generator 3' is arranged to generate single, occasional or a series of pressure waves in the fluid within the second system S2. A single pressure wave may represent a sneezing, occasional pressure waves may represent one or more coughs, and a series of pressure waves may represent regular or non-regular breathing. One or more pressure sensors 4*a*-4*c* are arranged to measure the fluid pressure in the first system S1. As long as the fluid connection C is intact, pressure waves generated by the second pulse generator 3' will travel from the second system S2 to the first system S1, and thus second pulses originating from the second pulse generator 3' will be detected by the pressure sensor(s) 4*a*-4*c* in addition to first pulses originating from the first pulse generator 3. It is to be noted that either one of the first and second pulse generators 3, 3' may include more than one pulse-generating device. Further, any such pulse-generating device may or may not be part of the respective fluid containing system S1, S2. The first fluid system may be an extracorporeal fluid circuit, such as an extracorporeal blood flow circuit of the type which is used for dialysis, and the second fluid system may be a vascular system, such as the blood circuit, of a subject. The second pulse generator 3' may also be referred to as a physiological phenomenon, and it may be a physiological pulse generator, cyclic or non-cyclic, repetitive or non-repetitive, autonomous or non-autonomous. The second pulse generator 3' may be a physiological phenomenon from the group consisting of reflex actions, voluntary muscle contractions, non-voluntary muscle contractions, a breathing system of said subject, an autonomous system of said subject for blood pressure regulation and an autonomous system of said subject for body temperature regulation. A reflex action, also known as a reflex, is to be construed as an involuntary and nearly instantaneous movement in response to a stimulus.

The fluid arrangement of FIG. 1 further includes a surveillance device 25 which is connected to the pressure sensors 4*a*-4*c*. Thereby, the surveillance device 25 acquires one or more measurement signals that may or may not be time-dependent to provide a real time representation of the fluid pressure in the first system S1. The surveillance device 25 monitors the behaviour of a physiological phenomenon of a subject and may issue an alarm or warning signal, and/or alert a control system of the first system S1, to take appropriate action. The surveillance device 25 may or may not process the measurement signal(s) continuously (i.e. on-line). The measurement signal(s) may also comprise a set or batch of measurement signals, extracted for subsequent analysis (i.e. off-line).

The surveillance device 25 optionally monitors the integrity of the fluid connection C, based on the principle that the presence of second pulses indicates that the fluid connection C is intact, whereas absence of second pulses indicates that the fluid connection C is compromised. The absence of second pulses may bring the surveillance device 25 to issue an alarm or warning signal, and/or alert a control system of the first or second fluid containing systems S1, S2 to take appropriate action.

The surveillance device 25 may thus be configured to continuously process the time-dependent measurement signal(s) to determine whether second pulses are present or not. Typically, the determination involves analyzing the measurement signal(s), or a pre-processed version thereof, in the time domain to calculate a value of an evaluation parameter (i.e. a parameter value) which is indicative of the presence or absence of second pulses in the measurement signal(s). Depending on implementation, the surveillance device 25 may use digital components or analogue components, or a combination thereof, for receiving and processing the measurement signal(s).

In the context of the present disclosure, "absence" of a pulse may imply that the pulse has disappeared, or at least that it has decreased sufficiently compared to the pulse deemed to be "present". The assessment of presence or absence may involve calculating an evaluation parameter value based on the measurement signal(s) and comparing the parameter value to a threshold value.

Figure 11:
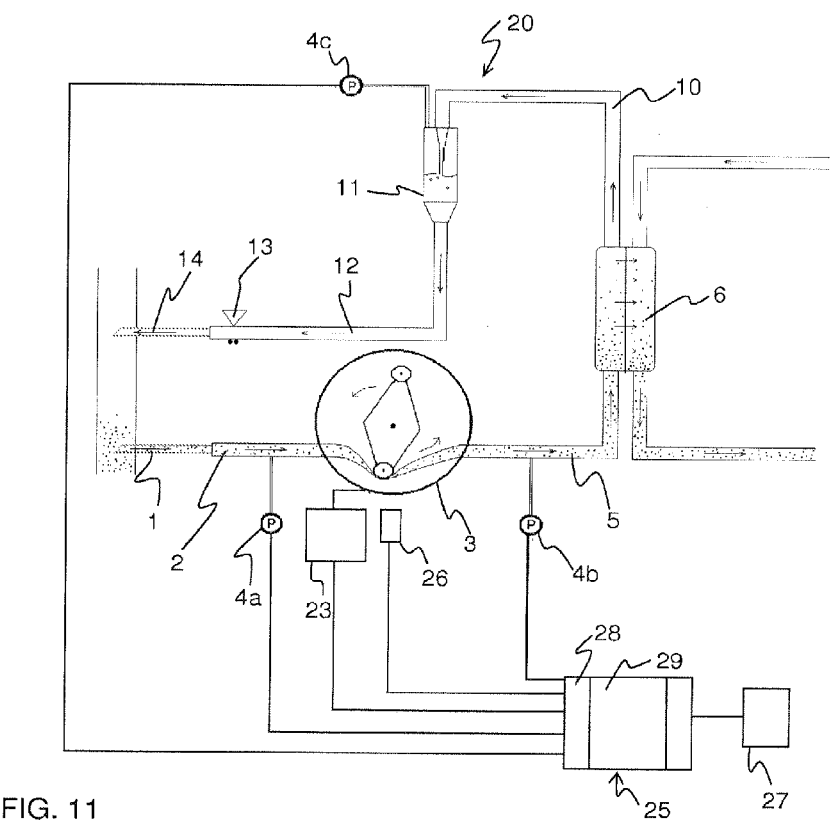
FIG. 11 is a schematic view of a system for hemodialysis treatment including an extracorporeal blood flow circuit.

FIG. 11 shows an example of an extracorporeal blood flow circuit 20 of the type which is used for dialysis. The extracorporeal blood flow circuit 20 comprises an access device for blood extraction in the form of an arterial needle 1, and an arterial tube segment 2 which connects the arterial needle 1 to a blood pump 3 which may be of peristaltic type, as indicated in FIG. 11, or any other suitable type, such as a membrane pump. At the inlet of the pump 3 there is a pressure sensor 4a (hereafter referred to as arterial sensor) which measures the pressure before the pump 3 in the arterial tube segment 2 (in the form of an "arterial pressure signal"). The blood pump 3 forces the blood, via a tube segment 5, to the blood-side of a dialyser 6. Many dialysis machines are additionally provided with a pressure sensor 4b that measures the pressure between the blood pump 3 and the dialyser 6. The blood is lead via a tube segment 10 from the blood-side of the dialyser 6 to a venous drip chamber or deaeration chamber 11 and from there back to the patient via a venous tube segment 12 and an access device for blood reintroduction in the form of a venous needle 14. A pressure sensor 4c (hereafter referred to as venous sensor) is provided to measure the pressure on the venous side of the dialyser 6 (in the form of a "venous pressure signal"). In the illustrated example, the pressure sensor 4c measures the pressure in the venous drip chamber. Both the arterial needle or catheter 1 and the venous needle or catheter 14 are connected to the patient through a blood vessel access. The blood vessel access may be of any suitable type, e.g. a fistula, a Scribner-shunt, a graft, etc. For simplicity, the following discussion presumes that the blood vessel access is a fistula.

In relation to the general arrangement in FIG. 1, the extracorporeal blood flow circuit 20 corresponds to the first fluid containing system S1, the blood pump 3 (as well as any further pulse source(s) within or associated with the circuit 20, such as a dialysis solution pump, valves, etc) corresponds to the first pulse generator 3, the blood system of the patient corresponds to the second fluid containing system S2, and a physiological phenomenon of the patient corresponds to the second pulse generator 3' which thus is located within or associated with the blood system of the patient. The fluid connection C corresponds to one or both of the fluid connections between the blood vessel access and the access device 1, 14.

In FIG. 11, a control unit 23 is provided, i.a. to control the blood flow in the circuit 20 by controlling the revolution speed of the blood pump 3. The extracorporeal blood flow circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

In FIG. 11, the surveillance device 25 comprises a data acquisition part 28 for pre-processing the incoming signal(s), e.g. including an A/D converter with a required minimum sampling rate and resolution, one or more signal amplifiers, one or more filters to remove undesired components of the incoming signal(s), such as offset, high frequency noise and supply voltage disturbances.

In the examples given herein, the data acquisition part 28 comprises a DAQ card USB-6210 from National Instruments with a sampling rate of 1 kHz and resolution of 16 bits, an operation amplifying circuit AD620 from Analog Devices, a high-pass filter with a cut-off frequency of 0.03 Hz (i.a., for removal of signal offset) together with a low-pass filter with a cut-off frequency of 402 Hz (i.a., for removal of high frequency noise). To obtain a short convergence time, a low-order filter is used for the filters. Furthermore, the data acquisition part 28 may include an additional fixed band-pass filter with upper and lower cut-off frequencies to suppress disturbances outside the frequency interval of interest.

The pre-processed data is provided as input to a main data processing part 29, which executes the inventive signal analysis.

Embodiments of the present invention utilize the fact that physiological phenomena arising in the body of a subject cause variations in the blood pressure of the subject. It has been found that these variations are, in turn, conducted via the fluid connection(s), the tube segments, the fluid (blood/air) in the tube segments, any intermediate fluid chamber (e.g. drip chamber 11) and the fluid therein, to one or more pressure transducers in the extracorporeal blood flow circuit. By signal analysis it is then possible to extract these pressure variations, and then subsequently, extract rate, amplitude, phase and shape of signals that represent the phenomena. This information may e.g. be useful to medical staff in observing breathing rate and depth of breath of a subject.

Implementation of the signal analysis may be done by executing a software algorithm in a computer, e.g. by digital filters, by mechanical filters, e.g. restrictors and compliance volumes, or by electronics, e.g. analogue filters or digital circuits dedicated for the purpose.

Hence, measurement data on e.g. respiration, blood pressure and temperature regulation may advantageously be provided on-line and continuously during extra-corporeal circulation. The measurement data may be determined from sensor information obtainable from most extra-corporeal treatment systems without need for extra disposables or making an extra blood access.

Hence, embodiments of the present invention enable the provision of vital signs, e.g. respiration rate and amplitude, and autonomous regulation, of a patient, in particular during dialysis treatment.

Embodiments of the present invention may be implemented as an apparatus, a computer-implemented method and a computer program product for identifying physiological signals with other origins than the heart of the subject. This is achieved by analysis of signals acquired from a tube/vessel in direct hydrostatic contact with the body of a subject via e.g. a needle or catheter inserted into the blood vessel access of a subject.

The physiological signal relevant to the invention may for instance originate from reflexes, voluntary muscle contractions, non-voluntary muscle contractions, breathing of a subject or come from signals related to the autonomic regulation of the subject's body. The frequency ranges of some of these phenomena are normally:

Breathing: approx. 0.15-0.4 Hz, with frequencies centred around approx. 0.25 Hz;

Blood pressure regulation due to the autonomous system: approx. 0.04-0.14 Hz, with frequencies centred around approx. 0.1 Hz;

Temperature regulation due to the autonomous system: approx. 0.001-0.1, with frequencies centred around approx. 0.05 Hz.

For the sake of simplicity, the following description will refer to the dialysis field without excluding a broader scope of applications. It will be assumed that the system signals that are subjected to the analysis are delivered by pressure sensors at the venous and/or the arterial side of the blood line (cf. sensors 4c and 4a, respectively, in FIG. 11) during a dialysis treatment. However, it may be anticipated that other type of sensors, e.g. optical sensors, such as a photoplethysmograpy sensor (PPG), displacement sensors, such as strain gauges and accelerometers, may be used as long as these convey equivalent information about relevant physiological signals from the patient.

Figure 4:
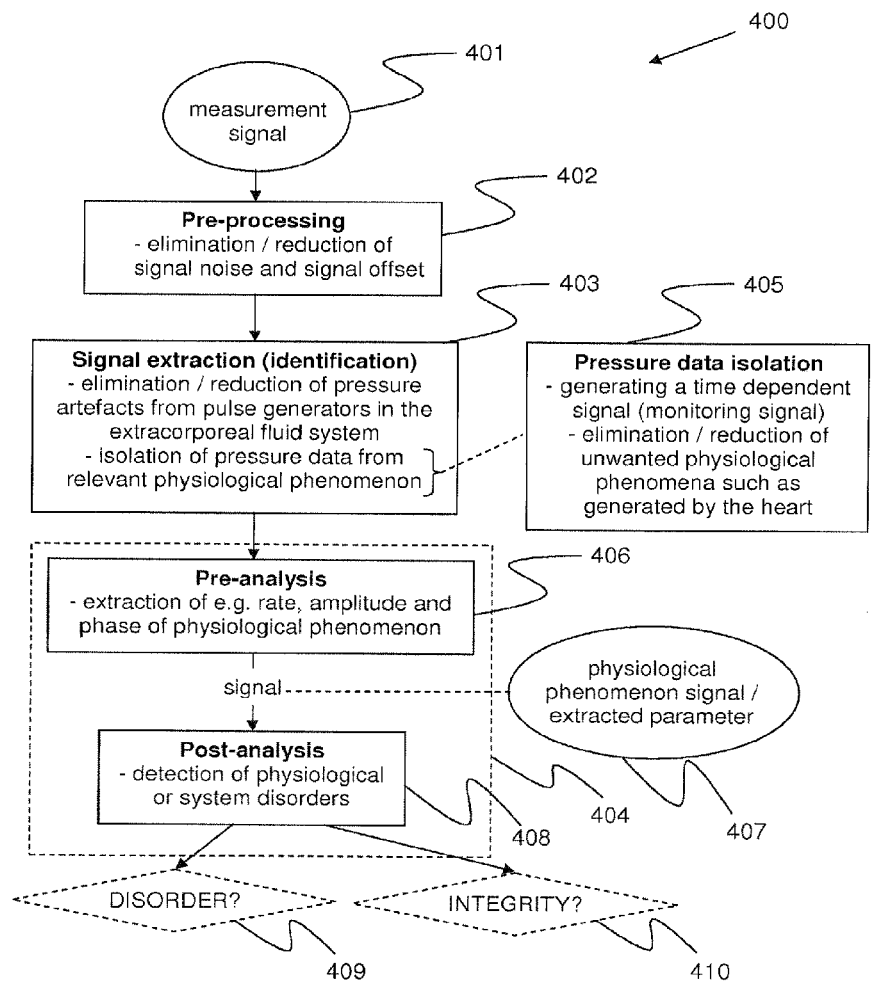
FIG. 4 is flow chart of a signal identification process according to one embodiment of the invention.

FIG. 4 is a flow chart that illustrates steps of a signal analysis process 400 executed by the surveillance device 25 according to an embodiment of the present invention. It is initiated by receiving a measurement signal 401, e.g. from the venous or arterial pressure sensors, comprising a number of pressure induced signal components. The signal analysis process may be divided into a pre-processing part 402, a signal extraction part 403 and an analysis part 404. The pre-processing part 402 includes elimination or reduction of signal noise, e.g. measurement noise, and signal offset, as detailed in the section above relating to the data acquisition part 28. The signal extraction part 403 involves elimination or reduction of pressure artefacts originating from pulse generators in the extracorporeal fluid system and isolation of pressure data originating from a relevant physiological phenomenon. In the context of the present disclosure, "pressure data isolation" 405 denotes a process of generating a time-dependent signal (also denoted monitoring signal herein) which is free or substantially free from pressure modulations caused by any unwanted physiological phenomena. Such unwanted physiological phenomena may vary between different applications, but generally include at least heart beats. The elimination of signal noise and signal offset (cf. part 402), as well as the elimination of pressure artefacts, may be included in algorithms for pressure data isolation. For instance, the measurement signal may be band pass filtered or low pass filtered to isolate a breathing signal, in a way such that signal noise and/or signal offset and/or pressure artefacts are eliminated from the measurement signal. The elimination of pressure artefacts may thus be performed before, after or during the pressure data isolation.

In a pre-analysis step 406 of the analysis part 404, one or more specific signal analysis algorithm(s) are applied for extraction of e.g. rate, amplitude and phase of the relevant physiological phenomenon. In a post-analysis step 408, based on one or more predetermined criteria, the output 407 of the signal analysis algorithm(s) is analysed, e.g. by pattern recognition, for signs of various disorders of physiological or system character, for instance indicated by detection of a disorder in step 409 and detection of the integrity of the fluid connection in step 410. The result of step 409 may be presented, e.g. displayed, to medical staff and may be useful in observing for instance breathing rate and breathing depth of a patient to detect, track or predict disorders and possibly take a corrective action.

In the following, the physiological phenomena will be explained in more detail, e.g. reflexes, voluntary muscle contractions, non-voluntary muscle contractions, the breathing system, the autonomous system for blood pressure regulation and the autonomous system for body temperature regulation for a human or animal. These phenomena may also be referred to as physiological pulse generators due to the blood pressure variations they generate.

Normally, the arterial blood pressure is modulated by 4 mmHg to 6 mmHg in a wavelike manner during respiration. Deep respiration may result in blood pressure variation of 20 mmHg.

The breathing induced modulation of the arterial blood pressure in the subject has several reasons:

"Cross-talk" between different parts of the sympathetic control system of the brain. Signals of the respiratory centre spill over to the centre controlling the vasomotor status causing blood pressure variations, the vasomotor referring to actions upon a blood vessel which alter its diameter by contraction and dilatation.

Breathing modulates the heart rate which modulates cardiac output and blood pressure.

Modulation of cardiac output due to variations of the pressure in the thoracic cavity during breathing. At inspiration the left ventricle of the heart is supplied with a smaller blood volume since more blood is contained in the blood vessels in the chest at the expense of the pump volume of the heart. Blood pressure will then change as the cardiac output varies.

Excitation of baroreceptors of the heart due to respiration. This will cause modulation of blood pressure since the sympathetic system will respond to the stretch of the baroreceptors by changing the blood pressure.

The hydro-static pressure change due to the rise and fall of the chest during respiration of a subject in supine position. At inspiration the centre of gravity is elevated which causes increased pressure.

Figure 2:
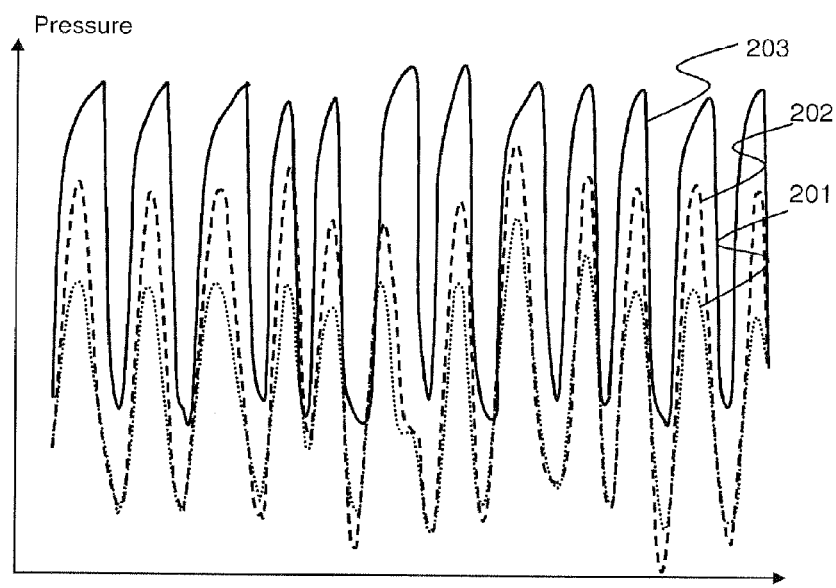
FIG. 2 is a plot of breathing signals generated/extracted from the measurement signal and from a reference instrument (capnograph) as a function of time.
Figure 3:
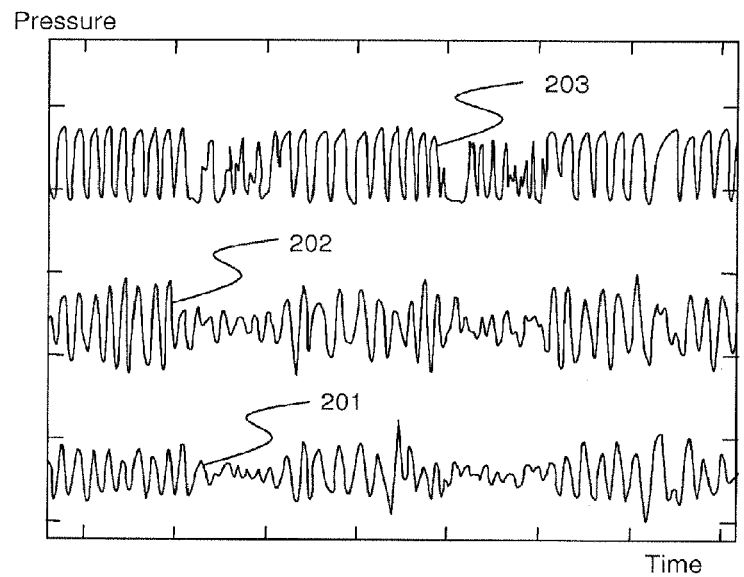
FIG. 3 is another plot of breathing signals from the measurement signals as a function of time.

FIG. 2 illustrates the synchronous breathing signals from the vein 201 (dotted line) and from the artery 202 (dashed line) generated by the signal extraction processing (cf. 402-403 in FIG. 4) of the venous and the arterial pressure signals recorded during a dialysis treatment by the venous and arterial pressure sensors (cf. 4c, 4a in FIG. 11). A "breathing signal", as used herein, denotes a signal representing/reflecting the repetitive cycles of inhalation and exhalation of a subject. The third curve 203 (solid line) shows a reference of the breathing signal provided by an external capnography device based on measurement of $CO_2$ of the respiration flow. FIG. 3 is a similar plot of the breathing signals in FIG. 2 and shows that the amplitude of the breathing signals 201, 202 extracted from the venous and arterial pressure signals, respectively, change in concordance with the depth of breath given by the capnography signal 203.

Vasomotor oscillations appear in the blood pressure in cycles with a length of about 7 seconds to about 26 seconds and an amplitude of about 10 mmHg to about 40 mmHg. The phenomenon is caused by self-oscillation of the sympathetic control system for the blood pressure with the baroreceptors as input signals.

The autonomous system is also involved in temperature control of the body via regulation of the vasomotor response to temperature changes. At low temperatures e.g. the arterioles are contracted to conserve energy of the body, which cause higher blood pressure. Similar to the vasomotor oscillations caused by the blood pressure control system, the temperature control system also give rise to cyclic variations in blood pressure. The temperature cycle rate is normally centred at around 0.05 Hz.

Figure 5:
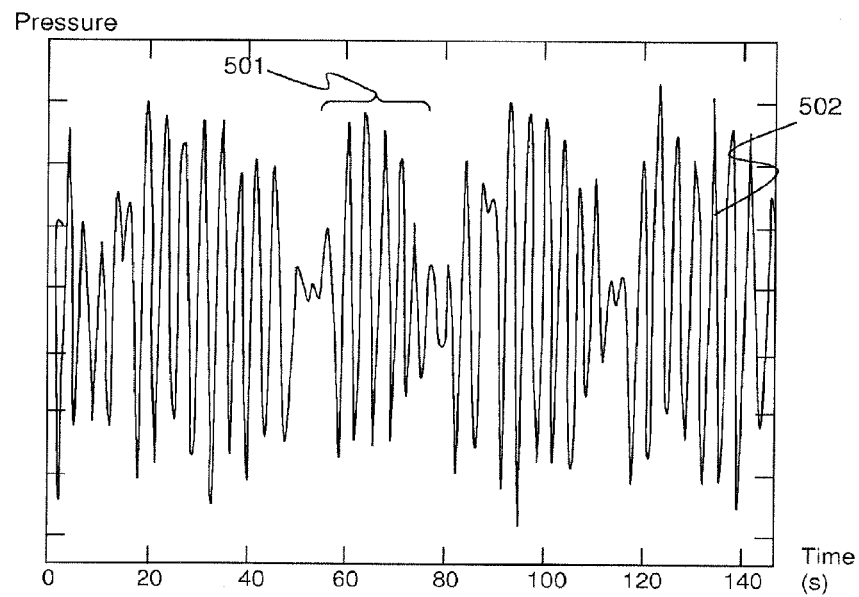
FIG. 5 is a plot of a breathing signal as a function of time.

FIG. 5 shows the modulation 501 of a breathing signal 502 from the venous pressure signal measured by pressure sensor 4c of FIG. 11 due to oscillation of an autonomous control system in the frequency range of temperature regulation.

In the simplest case of pressure signal analysis, no pump or other source of pressure artefacts is present in the extracorporeal fluid circuit connected to the subject during the data acquisition. For instance, the pump may have been shut down.

In the general case, however, one or more pumps are running or other sources of cyclic or non-cyclic, repetitive or non-repetitive artefacts are present during the data acquisition. Information on the cyclic disturbances may be known from external sources, e.g. other sensors or controllers, or may be estimated or reconstructed from system parameters, e.g. the blood flow rate.

Cyclic pressure artefacts may originate from operating a peristaltic pump, repetitive actuation of valves, movements of membranes in balancing chambers. According to the findings in connection with the present invention, artefacts may also originate from mechanical resonance of system components such as swinging movements of blood line energized by e.g. a pump. Frequencies of blood line movements are given by the tube lengths and harmonics thereof and by the beating between any frequencies involved, i.e. between different self-oscillations and pump frequencies. These frequencies may differ between the venous and arterial lines. Mechanical fixation of the blood lines and other free components may remedy the problem of mechanical resonance. Alternatively, an operator may be instructed to touch or jolt the blood lines to identify natural frequencies associated with the blood lines, which information may be used in the analysis for improved removal of components not belonging to the pressure data of interest.

Examples of non-cyclic artefacts are subject movement, valve actuation, movements of tubings, etc.

In the following, various techniques for signal extraction (cf. 403 in FIG. 4) will be briefly discussed.

Signal Extraction

In the following, embodiments for eliminating various artefacts will be described. Then, embodiments for isolating pressure data originating from a relevant physiological phenomenon are described.

The pressure data to be extracted is not limited to a single physiological phenomenon and may originate from one or more physiological phenomena, excluding the heart.

Elimination of Artefacts

Elimination of artefacts may be provided by:

Controlling a pulse generator in the extracorporeal fluid system, such as a pump By temporarily shutting down the pulse generator, or By shifting the frequency of the pulse generator;
Low pass, band pass or high pass filtering;
Spectral analysis and filtering in the frequency domain;
Time domain filtering.

Controlling a Pulse Generator

Artefacts from a pulse generator, such as a pumping device, in the extracorporeal blood flow circuit may be avoided by temporarily shutting down the pulse generator, or by shifting the frequency of the pulse generator away from frequencies of one or more relevant physiological phenomena.

With specific reference to the use of the pressure data for integrity detection (cf. step 410 in FIG. 4), artefacts may be eliminated by feedback control with respect to the relevant physiological signal, e.g. a breathing signal, from an independent source, e.g. a capnograph instrument. Such feedback control may thus be used to set the pump frequency optimally for detection of the relevant physiological signal in the pressure signal. For example, control unit 23 of FIG. 11 may be operated to set the pump frequency based on an external signal in order to facilitate the detection of the relevant physiological signal, i.e. the pump frequency is controlled to minimize overlap in frequency between the pump and the physiological phenomenon of relevance.

Artefact Elimination by Applying Low Pass, Band Pass or High Pass Filters

The measured signal may be fed into a filter, e.g. digital or analogue, with suitable frequency characteristics, such as frequency range and/or centre of frequency range, corresponding to a pulse generator, such as a pump, in the extracorporeal circuit. For instance, in a case where the pulse generator, such as a pump, operates within the frequency range of 1 Hz, a suitable low pass filter may be applied in order to obtain the frequency of the physiological phenomenon below 1 Hz. Correspondingly, a high pass filter may be applied to obtain a physiological phenomenon with frequency higher than the pulse generator.

Spectral Analysis and Filtering in the Frequency Domain

With spectral analysis, detection and elimination of amplitude peaks in a spectrum may for instance be performed by Fast Fourier Transform (FFT) methods. Alternatively, the elimination may be achieved by applying a notch filter or the like at one or more frequencies identified by an FFT method or the like.

Time Domain Filtering

Artefact elimination by filtering in the time domain is further disclosed and exemplified in relation to FIGS. 12-23(b). In addition to FIGS. 12-23(b), reference is also made to Applicant's PCT publication WO2009/156175 which is incorporated herein in its entirety by this reference.

Isolating Pressure Data from a Physiological Phenomenon

Isolating pressure data originating from a relevant physiological phenomenon (cf. 405 in FIG. 4) may be provided by any or a combination of:

Low pass, band pass or high pass filtering;
Spectral analysis and filtering in the frequency domain; or
Time domain filtering.

Pressure data isolation by applying low pass, band pass or high pass filters

The measurement signal may be fed into a filter, e.g. digital or analogue, with suitable frequency characteristics, such as frequency range and/or centre of frequency range, corresponding to a signal of relevant physiological phenomenon where e.g. in case the isolation concerns:

Breathing, a frequency range of approx. 0.15-0.4 Hz will be allowed to pass the filter;

Blood pressure regulation due to the autonomous system, a frequency range of approx. 0.04-0.15 Hz will be allowed to pass the filter; and Temperature regulation due to the autonomous system, a frequency range of approx. 0.001-0.1 Hz will be allowed to pass the filter.

Spectral Analysis and Filtering in the Frequency Domain

With spectral analysis, detection and elimination of amplitude peaks in a spectrum may for instance be performed by Fast Fourier Transform (FFT) methods. Alternatively, the elimination may be achieved by applying a notch filter or the like at one or more frequencies identified by an FFT method or the like.

Pressure Data Isolation by Time Domain Filtering

The signal of interest may be extracted from the pressure signal as an error signal of an adaptive filter. The adaptive filter is fed with both the measurement signal and a predicted signal profile of a cyclic disturbance. The cyclic disturbance may originate from any unwanted physiological phenomenon (e.g. heart pulsation). Particularly, a reconstructed pressure profile originating from the heart may be input to the adaptive filter. This and other time domain filtering techniques for removing unwanted signal components from a measurement signal are further disclosed and exemplified in relation to FIGS. 12-23(b). Although FIGS. 12-23(b) are concerned with eliminating first pulses originating from a pulse generator in an extracorporeal circuit, such as a pumping device, it is equally applicable for eliminating first pulses originating from unwanted physiological phenomena, as long as a predicted signal profile of the first pulses may be obtained. The skilled person realizes that such a predicted signal profile may be obtained in any of the ways described in relation to FIGS. 12-23(b). In addition to FIGS. 12-23(b), reference is also made to Applicant's PCT publication WO2009/156175 which is incorporated herein in its entirety by this reference.

Some of the filtering techniques described above may automatically be achieved by down-sampling in the anti-aliasing filter included in a down-sampling signal processing algorithm. Additionally, some of the above described filtering techniques may also be achieved directly in hardware, e.g., in the Analogue-to-Digital conversion by choosing an appropriate sample frequency, i.e. due to the anti-aliasing filter which is applied before sampling.

Detecting Disorders

This section relates to detection, presenting, tracking and prediction of various physiological disorders, such as sleep apnea, hyperventilation, coughing etc (cf. 409 in FIG. 4). It is based on analysis of the physiological signal that is extracted out of a pressure signal acquired from an extracorporeal fluid system.

On a general level, the detection, presenting, tracking and prediction of physiological disorders may involve calculating an evaluation parameter value based on the isolated pressure data resulting from the aforesaid signal extraction. The evaluation parameter value is then analysed as part of a process for detecting a physiological disorder. As used herein, "tracking" denotes a process of continuously or intermittently determining/trending a physiological phenomenon as reflected by the isolated pressure data as such or by the absolute/relative parameter values extracted from the isolated pressure data. As used herein, "prediction of a disorder" may involve notifying the disorder in advance and/or estimating a risk for the disorder to exist or to emerge.

Different techniques for calculating such an evaluation parameter value are further disclosed and exemplified in relation to FIGS. 24-43, in which the isolated pressure data corresponds to a time-dependent monitoring signal which is obtained by processing at least one measurement signal to essentially eliminate the first pulses (e.g. pump pulses) while retaining the second pulses (e.g. heart pulses). In FIGS. 24-43, the resulting time-dependent monitoring signal may be subjected to a time domain analysis which results in an evaluation parameter value that is used for monitoring the integrity of a fluid connection between the vascular system of a patient and an extracorporeal blood flow circuit. All techniques disclosed in relation to FIGS. 24-43 with respect to the signal processing and evaluation of heart pulses, including the use of timing information, are equally applicable for evaluating other physiological phenomena, such as breathing, autonomic regulation of body temperature, and autonomic regulation of blood pressure, or combinations thereof, for the purpose of detecting various physiological disorders. In addition to FIGS. 24-43, reference is also made to Applicant's PCT publication WO2009/156174 which is incorporated herein in its entirety by this reference.

There are of course other techniques for calculating the evaluation parameter value, including other types of time domain analyses, as well as different types of frequency domain analyses, e.g. as indicated in the following.

Other factors, such as the medical history of the patient, e.g. heart status, blood pressure and heart rate may also be utilized for improving the performance of the detection and monitoring of the various physiological disorders.

The following sections describe a range of different physiological disorders that may be detected in arterial or venous pressure signals. Unless specifically mentioned, it is assumed that there is a medical interest of detecting or monitoring these disorders for diagnostic purposes, for safety and for surveillance.

Figure 6:
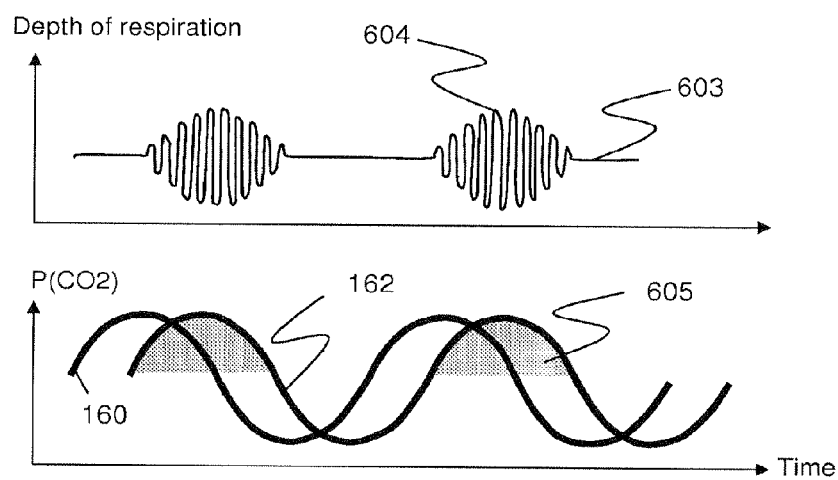
FIG. 6 is a plot of an exemplifying breathing disorder response.

One breathing disorder is periodic breathing disorder, which means that a subject breathes deeply for some time in a repetitive manner and directly after that just slightly or not at all. One type of periodic breathing is called Cheyne-Stokes breathing. FIG. 6 shows an example of Cheyne-Stokes breathing 603, and also shows how the pressure $P(CO_2)$ 160 in the pulmonary (lung) blood and delayed changes in the pressure $P(CO_2)$ 162 of the fluids of the brain's respiratory centre excite the respiratory centre 605 which cause a situation of deep respiration 604. It may be caused by a too long delay for the transport of blood, e.g. due to cardiac failure, from the lungs to the respiratory centre of the brain to allow the feed-back control to work properly. Functional problems of the respiratory centre due to for instance brain damage may also be a reason for periodic breathing.

The periodic breathing and the cycle thereof may according to the present invention be detected both in the time and frequency domain via e.g. filtering, envelop detection, e.g. Hilbert transform, or pattern matching.

Other breathing disorders include apnea (or apnoea) which may be classified as stopped respiration for at least 10 seconds, and hypopnoea which may be classified as reduced respiration volume of ≥50%, but ≤100%, for at least 10 seconds with a ≥4% reduction of oxygen saturation of the blood. Hypopnea is a disorder which involves episodes of overly shallow breathing or an abnormally low respiratory rate. This differs from apnea in that there remains some flow of air. Hypopnea events may happen while asleep or while awake.

Figure 7:
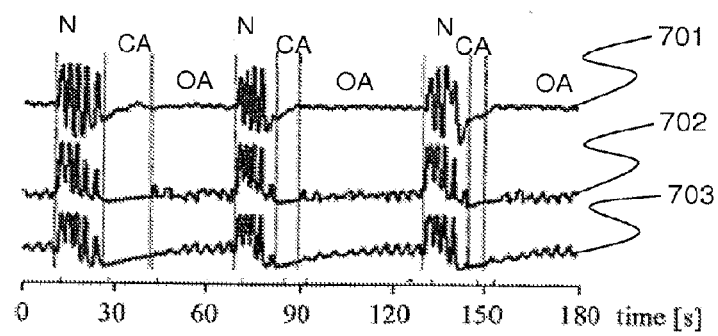
FIG. 7 is a plot of breathing related parameters identified in connection with a breathing disorder.

Sleep apnea may be manifested as repetition of a certain breathing pattern. This may be seen in the three curves of FIG. 7 representing air flow 701, movements of thorax 702 and abdomen 703, respectively. Two main types of apnea are referred to as central and obstructive, denoted CA and OA in FIG. 7. N denotes normal breathing. Central apnea is caused by malfunction of the respiratory centre of the brain, whereas obstructive apnea is caused by blockage of the respiration path of the patient during sleep.

By identifying this kind of pattern in the breathing signal provided from the pressure signal analysis, apnea may be detected. The detection criterion for sleep apnea or hypopnea may e.g. be defined as equal to or more than 5 episodes of apnoea or hypopnea per hour of sleep.

Furthermore, patients in severe, life-threatening situations, e.g. after over-dosing of opiate-based medication or other Central Nervous System (CNS) depressant drugs, may stop respiration or reduce the respiration frequency markedly. Patients that are not observed constantly, e.g. patients performing home-dialysis treatments, may be helped out of dangerous situations if stopped breathing can be detected automatically. A detection criterion for hypoventilation may be rate-related, e.g. be set to the frequency range below normal breathing, e.g. approx. 0.15 Hz, provided that this condition has prevailed at least for a period of certain length, e.g. approx. 30 s. Low amplitude of the breathing signal may also be used as an indicator of hypoventilation by itself or in combination with the rate-related detection criterion.

Heart conditions, such as angina pectoris, left ventricular hypertrophy, stroke or congestive heart failure are sometimes expressed via irregular heart rhythm, ectopic beats and coughing. In case no surveillance of the heart is present, e.g. with electro-cardiogram (ECG), identification of coughing is often used as a clinical marker of heart conditions in dialysis patients. Intense coughing may also indicate infection or allergic reaction, which is also true for sneezing.

Coughing and sneezing may influence physiological measurements obtained from external instruments, e.g. it is known that coughing will introduce errors in a PPG signal (e.g. measured with a pulse oximeter). Thus, detection of coughing or sneezing may also be used in correction procedures for errors and artefacts in other physiological measurements. For instance, it is known that coughing may induce false alarms in a PPG-based method for hypotension prediction. In embodiment of the present invention, detection of coughing and sneezing may thus also be used to reduce the number of false alarms in PPG-based methods for hypotension prediction.

The cough and sneezing reflex comprises a rapid inspiration of air, up to 2.5 liters, followed by a forceful contraction of the abdominal and expiratory muscles causing a rapid increase of the pressure in the lungs (≥100 mmHg) before the air is expelled at high velocity. The lung pressure variations of the two phases inspiration and expiration cause corresponding changes of the blood pressure, which is seen in pressure measurements of an extra-corporeal circuit. Coughing and sneezing may e.g. be detected as a disruption of the normal breathing signal by non-cyclic pressure peaks larger than certain limits and with a duration within a certain range or by pattern matching to standardized or individualized pressure profiles representing coughing or sneezing.

Patients in stressed conditions, e.g. suffering from a panic attack, may breathe at higher rate, which may result in hyperventilation. It may also occur as a consequence of various lung diseases, head injury, stroke and various respiration disorders, e.g. central neurogenic hyperventilation, apneustic respirations, ataxic respiration, Cheyne-Stokes respirations or Biot's respiration. Also, in the case of metabolic acidosis, the body uses hyperventilation as a compensatory mechanism to decrease acidity of the blood. Dialysis patients e.g. may suffer from acidosis which may trigger hyperventilation.

Hyperventilation is linked with an increased risk for disturbances of the blood chemistry ($pCO_2$, pH, and $pO_2$), since it causes reduction of the carbon dioxide concentration of the blood to below its normal level, which, in turn, raises the blood's pH value, making it more alkaline. Alkaline blood chemistry may initiate constriction of the blood vessels which supply the brain and may prevent the transport of certain electrolytes necessary for the function of the nervous system.

Hyperventilation may, but does not always, cause symptoms such as numbness or tingling in the hands, feet and lips, lightheadedness, dizziness, headache, chest pain, slurred speech and sometimes fainting.

Hyperventilation may e.g. be indicated if the rate of the breathing signal generated from pressure analysis is higher than the normal upper range, e.g. approx. 0.4 Hz and in particular approx. 0.8 Hz.

Asthmatic attacks are caused by congestion in the pulmonary tract, which particularly reduces the ability of a subject to exhaust air from its lungs. The flow and the rate of ventilation are decreased while breathing effort is increased. The respiration cycle is therefore clearly disturbed, which may be detected as an abnormal breathing rate with e.g. relatively shorter inspiration compared to expiration. The unusually high pressure amplitude during the extended expiration phase may also be used for detecting asthmatic attacks.

A further disorder which may be detected in one embodiment of the present invention is epilepsy, which is a common chronic neurological disorder characterized by recurrent unprovoked seizures. These seizures are transient signs and/or symptoms of abnormal, excessive or synchronous neuronal activity in the brain. Seizures can cause involuntary changes in body movement or function, sensation, awareness, or behaviour. Specifically it may include series of involuntary muscular contractions due to sudden stretching of the muscle. These may affect the blood pressure of the subject (e.g. by elevation or rhythmic modulation) which in turn may change the venous and arterial pressure in the extracorporeal circuit. A seizure can last from a few seconds to status epilepticus, a severe condition with a continuous seizure that will not stop without intervention.

It is clear that regular respiration is disrupted also when the subject is talking or is having a meal. The corresponding measurement/breathing signals do not show a definite pattern, however it may e.g. be detected by statistical pattern analysis with multivariate statistical methods or with additional signal extraction, external or internal, e.g. with a microphone or a blood volume sensor (it is known that blood volume is reduced in response to food intake). Detection of speech or food intake may be done so as to prevent that the measurement signal is used for detecting a disorder during such speech/food intake. Alternatively or additionally, the presence of speech can be detected by analysing the measurement signal in the frequency region above about 3.5-4 Hz, typically above about 100 Hz. For increased certainty, it may be required that corresponding speech signals are found in measurement signals from plural pressure sensors, e.g. the arterial and venous pressure sensors 4a, 4c in FIG. 4.

The signal levels in the arterial and venous pressure signals may change rapidly due to other physiological mechanisms. Contraction of the abdominal muscles causes increase of blood pressure and consequently also an intermittent rise in the signal levels of the arterial and venous pressure signals. A medically relevant example of this is vomiting, which may be identified as a deep breath followed by forceful contractions of the abdominal muscles and lowering of the diaphragm. Detection of severe repetitive hiccups may also be of interest. These kind of reflex-controlled phenomena have typical patterns which allow detection by matching to standard patterns.

A disorder that is detected during dialysis, in particular nocturnal dialysis, may be automatically communicated to the clinical staff directly or stored in a computer system for off-line monitoring, diagnosing or statistical purposes. It may also be provided as feedback directly to the patient, medical staff and/or machine system to counteract the disorder.

For instance, if the patient cannot constantly be observed during e.g. a dialysis treatment it may be beneficial to identify a deviating breathing pattern such as coughing apnea or epilepsy via automatic detection in the dialysis machine. The medical staff may be notified directly via an alert signal or indirectly as information sent by a communication channel, such as to a server for subsequent retrieval.

An alert or alarm may be issued on detection of a deviation from a normal physiological pattern, such as breathing, of a patient, for instance when the duration of an asthmatic attack, coughing or apnea exceeds a predetermined limit or if vomiting is detected.

Detecting ectopic beats accompanied by Blood Pressure Turbulence (BPT)

An embodiment of the present invention further relates to a method for detecting ectopic heart beats accompanied by Blood Pressure Turbulence (BPT) events by monitoring of the physiological signal generated by signal extraction processing of the pressure signal(s) acquired continuously from an extracorporeal circuit. Hence, there is no need for external instruments for blood pressure measurements to detect BPT events, nor is external instruments for heart monitoring needed for counting the presence of ectopic beats (also denoted EBC) which generate the BPT event.

Figure 8:
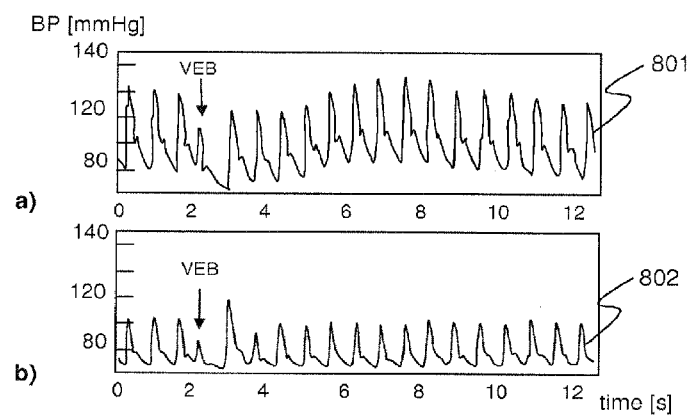
FIG. 8 is a plot of a blood pressure turbulence event (BPT) in a) a healthy subject and b) a subject with unhealthy cardiovascular response.

The blood pressure of a subject is modulated directly after a ventricular ectopic beat (VEB) episode. FIG. 8 shows the blood pressure response after a VEB, i.e. Blood Pressure (BP) response 801 to a VEB in a healthy subject and blood pressure response 802 to a VEB in a patient with idiopathic dilated cardiomyopathy.

Figure 9:
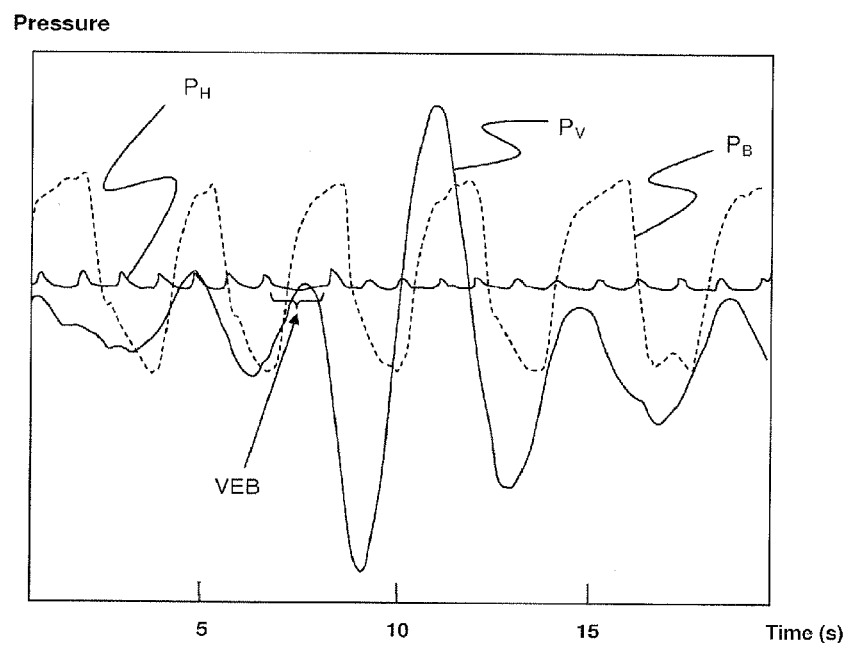
FIG. 9 is a plot of breathing signals in connection with an event of blood pressure turbulence.

FIG. 9 shows an event of BPT taking place during a dialysis treatment. A capnography device is used for providing a reference or benchmark signal of breathing $P_B$, and a reference or benchmark signal of heart pulsations $P_H$ is generated by a pulse oximeter. Signal extraction processing of a venous pressure signal from the extracorporeal circuit results in a pressure signal $P_v$ which isolates pressure data that originates from the breathing system and the autonomous system for blood pressure regulation in the patient. A VEB, indicated with an arrow in FIG. 9, is seen as a prolonged delay between the normal beats of the heart. A sequence of pressure turbulence comes immediately after the VEB and can be identified in the isolated pressure signal $P_v$. To be more precise, the isolated pressure signal $P_v$ will reflect breathing up until the time of the VEB. After the VEB, the isolated pressure signal $P_v$ will reflect the combined effects of breathing and BPT, and after the BPT event has faded away (after about 15 seconds in FIG. 9), only breathing remains. FIG. 9 illustrates that BPT events can be detected in the isolated pressure signal $P_v$, even in the presence of a breathing signal. It is to be understood that the venous pressure signal may be processed for removal of the breathing signal as well, to isolate only pressure data from the autonomous system for blood pressure regulation.

Figure 10:
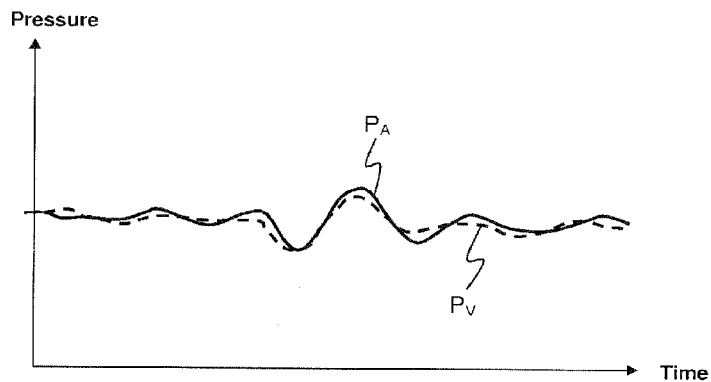
FIG. 10 is a plot of breathing signals as measured at the venous and arterial pressure side, respectively, in connection with an event of blood pressure turbulence.

FIG. 10 illustrates isolated pressure signals $P_v$, $P_A$ obtained during a BPT-event by signal extraction processing of a venous pressure signal and an arterial pressure signal, respectively, from pressure sensors in an extracorporeal circuit. As shown, the isolated pressure signals comprise both breathing and BPT components. This figure illustrates that pressure measurements from both the venous and arterial sites may be used for detecting BPT-events during extra-corporeal circulation. Optionally, the BPT component may be isolated by removing the breathing component.

Detection of the BPT-event can be done in different ways, for instance:

By band-pass filtering of the venous and/or the arterial pressure signals, since the spectral content of BPT is in the low frequency range of approx. 0.04-0.15 Hz, with frequencies typically centred around approx. 0.1 Hz.

By correlation of one or more isolated pressure signals $P_v$, $P_A$ (which, e.g., may isolate pressure data originating from the autonomous system for blood pressure regulation, and possibly also the breathing system) with a standardized pressure profile of a BPT event. If the correlation coefficient is larger than a certain limit, a BPT event is detected.

By averaging isolated pressure data (which, e.g., may originate from the autonomous system for blood pressure regulation, and possibly also the breathing system) after several different VEBs. The averaging may involve combining (adding) isolated pressure signals obtained from plural pressure sensors (e.g. the arterial and venous pressure sensors 4a, 4c in FIG. 4), or combining (adding) sequential segments in one isolated pressure signal.

Detection of BPT events may be useful for determining occurrence and rate of ectopic beats (i.e., EBC) as an indicator of the patient's heart condition. It has also been shown that EBC may be used for detecting/predicting dialysis induced hypotension.

By finding the timing of a VEB in another signal than the isolated pressure signals $P_v$ and $P_A$ (e.g., in the heart pulsations $P_H$), it may be possible to detect impaired or lack of autonomous blood pressure regulation. This may be accomplished by evaluating the magnitude of the BPT event that follows the VEB.

Furthermore, it has been shown that, dialysis patients with reduced BPT (i.e., impaired or lack of autonomous blood pressure regulation) are prone to dialysis induced hypotension, whereas dialysis patients with more normal BPT events are resistant to hypotension. Clinically, it may be advantageous to be able to classify dialysis patients in this manner.

Detection of impaired or lack of all different kinds of autonomous regulations, not only blood pressure regulation, are of medical interest. In addition, magnified or overcompensated autonomous regulation (in contrast to impaired or lack of) are also of medical interest. The status of the autonomous regulation (i.e., impaired, lack of, magnified or overcompensated) may, e.g., be detected by comparing the actual autonomous regulation to a threshold (and/or a pattern) of the different status.

Monitoring the Integrity of a Fluid Connection

Embodiments of the invention further relates to an apparatus, a method and a computer-implemented method for detecting disconnection of an extracorporeal circuit from a subject based on analysis of signals originating from a physiological phenomenon, such as breathing and/or autonomous regulation in the body of the subject.

Turning to FIG. 11, and as discussed by way of introduction, it may be vital to monitor the integrity of the connection of the access device 1, 14 to the blood vessel access with respect to malfunction in the injection and/or extraction of blood there through. In many dialysis machines, one or more of the pressure detectors 4a-4c are not present. In one embodiment of the invention, the integrity of the fluid connection between the blood vessel access and the venous access device 14 is monitored based on a measurement signal from the venous pressure sensor 4c.

Further, in FIG. 11, the surveillance/monitoring device 25 is configured to monitor the integrity of a venous-side fluid connection between the patient and the extracorporeal blood flow circuit 20, specifically by monitoring the presence of a signal component originating from a physiological phenomenon other than the heart of the patient. Absence of such a signal component is taken as an indication of a failure in the integrity of the fluid connection, e.g. that the venous access device 14 is dislodged from the blood vessel access, and brings the device 25 to activate an alarm and/or stop the blood flow, e.g. by stopping the blood pump 3 and activating a clamping device 13 on tube segment 12. The surveillance device 25 is at least connected to receive a measurement signal of the pressure sensor 4c. The device 25 may also be connected to pressure sensors 4a, 4b, as well as any additional sensors included in or attached to the extracorporeal blood flow circuit 20, such as further pressure sensors (4a, 4b in FIG. 11) or a dedicated breathing sensor, e.g. a capnography instrument. As indicated in FIG. 11, the device 25 may also be connected to the control unit 23. Alternatively or additionally, the device 25 may be connected to a measurement device 26 for indicating the frequency and phase of the blood pump 3. The device 25 is tethered or wirelessly connected to a local or remote device 27 for generating an audible/visual/tactile alarm or warning signal. The surveillance device 25 and/or the alarm device 27 may alternatively be incorporated as part of a dialysis apparatus.

In the event of a dislodgement of the venous access device 14, the pathway of all physiological signals from the subject to any sensor of the corresponding side of the extracorporeal circuit 20 is disrupted. This may be detected directly after a short delay needed by the signal analysis algorithm to assert certainty of the conclusion.

The integrity of a fluid connection may be monitored by detecting transmission of a pressure wave across the fluid connection. There is thus a pressure wave generator on one side of the fluid connection and a detection device on the other side. In an embodiment, the patient's breathing system is used as the pressure wave generator whilst a pressure sensor is arranged on the other side of the fluid connection, e.g. in the tube segment which leads from a access device 1, 14 and further into the extracorporeal circuit 20. In further embodiments, the patient's reflexes, voluntary muscle contractions, non-voluntary muscle contractions, the autonomous system of the patient for blood pressure regulation or the autonomous system of the patient for body temperature regulation may be used as the pressure wave generator. In yet further embodiments, the detection of speech is used for monitoring the integrity of the fluid connection. The presence of speech can be detected by analysing the measurement signal in the frequency region above about 3.5-4 Hz, typically above about 100 Hz.

Thus, the integrity of the fluid connection is determined based in the presence or absence of pressure pulses originating from a relevant physiological phenomenon in the patient, excluding the heart. The assessment of presence or absence may involve calculating an evaluation parameter value based on the isolated pressure data resulting from the aforesaid signal extraction, and comparing the evaluation parameter value to a threshold value. Different techniques for calculating such an evaluation parameter value are further disclosed and exemplified in relation to FIGS. 24-43. As noted above, all techniques disclosed in relation to FIGS. 24-43 with respect to the extraction, signal processing and evaluation of heart pulses are equally applicable to other physiological phenomena, such as breathing, autonomic regulation of body temperature, and autonomic regulation of blood pressure, or combinations thereof. In addition to FIGS. 24-43, reference is also made to Applicant's PCT publication WO2009/0156174 which is incorporated herein in its entirety by this reference. It may be emphasized that the above-mentioned dedicated breathing sensor may be used to provide the timing information that may be used for calculating the evaluation parameter value as taught by FIGS. 24-43.

In alternative embodiments, the evaluation parameter value is calculated based on a frequency domain analysis of the isolated pressure data, e.g. by finding an amplitude peak in an FFT spectrum.

In still other embodiments, also described in relation to FIGS. 24-43, when the isolated pressure data includes pressure artefacts from a pulse generator in the extracorporeal circuit, presence and absence of pressure pulses originating from the relevant physiological phenomenon in the patient is detected via beatings, i.e. amplitude modulations, in the isolated pressure data formed by interference between pressure waves generated by the relevant physiological phenomenon and pressure waves generated by the pulse generator. Hence, instead of trying to isolate a signal component generated by the relevant physiological phenomenon in the isolated pressure data, the presence of such a signal component is thus identified via the secondary effect of beating. Generally, beating is a phenomenon which is especially noticeable when two signals with closely spaced frequencies are added together. Thus, the beating signal detection is inherently well-suited to be used when other techniques fails, for instance when the frequency of the relevant physiological phenomenon lies close to a frequency component of the pulse generator, e.g. a pumping device in the extracorporeal circuit.

To avoid an overlapping frequency of the pump and the physiological signal, which may make detection more difficult, the appropriate physiological signal may be chosen depending on the actual pump rate, or the pump frequency may be changed depending on the frequency of the relevant/chosen physiological phenomenon. For example, with a peristaltic blood pump of a typical dialysis machine (~5 ml/pump stroke), the breathing signal would be applicable for blood flow rates substantially in the range of >120 ml/min (i.e. >0.4 Hz) and <45 ml/min (i.e. <0.15 Hz). The autonomous signals would in that case be suitable for blood flow rates >45 ml/min. This means that more than one physiological signal may be suitable for detection of access device dislodgement in some frequency intervals. Note that a heart signal, e.g. isolated in accordance with FIGS. 12-23(b) and processed in accordance with FIGS. 24-43, may be used for dislodgement detection in combination with any of the other physiological signals. Thus, the surveillance device 25 may be configured to actively switch, e.g. based on the blood flow rate or the pump frequency, between different detection modes so as to avoid frequency overlaps, where the different modes may involve isolating pressure data from different physiological phenomena and detecting dislodgement based on absence/presence of a signal component originating from the relevant physiological phenomenon.

The acceptable detection time for dislodgement detection depends on maximum acceptable blood loss and actual blood flow. This means that detection of fluid connection integrity by e.g. breathing or autonomous signals may not be applicable at blood flows higher than an upper limit. Assuming, for example, that the maximum blood loss is 200 ml from dislodgement of the venous access device to detection and that the detection time by autonomous signal is 120 seconds, the acceptable blood flow in that case must be less than approx. 100 ml/min.

In the above-described embodiments, all or part of the functionality of the surveillance/monitoring device 25, including data acquisition part 28 and main processing part 29, may be provided by dedicated hardware and/or by special-purpose software (or firmware) run on one or more general-purpose or special-purpose computing devices. In this context, it is to be understood that each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software controlled computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The computing device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The computing device may include one or more communication interfaces, such as a serial interface, a parallel interface, a USB interface, a wireless interface, a network adapter, etc, as well as one or more data acquisition devices, such as an A/D converter. The special-purpose software may be provided to the computing device on any suitable computer-readable medium, including a record medium, a read-only memory, or an electrical carrier signal.

It should be understood that various changes and modifications to the presently preferred embodiments described herein will be apparent to those skilled in the art. Such changes and modifications may be made without departing from the spirit and scope of the present invention and without diminishing its attendant advantages. It is therefore intended that such changes and modifications be covered by the appended claims. References within this text to a, an, one and first should be construed as one or more.

In the following, a set of items are recited to summarize some aspects and embodiments of the invention as disclosed in the foregoing, possibly taken in combination with the content of FIGS. 12-43 and the accompanying description.

Item 1: A method for processing a measurement signal obtained by a pressure sensor (4a-4c) in an extracorporeal fluid system (S1) connected to a vascular system (S2) of a subject, said method comprising: receiving the measurement signal; and processing the measurement signal for identification of pressure data originating from a first physiological phenomenon in said subject, said physiological phenomenon excluding the heart of said subject.

Item 2: The method of item 1, wherein said physiological phenomenon is included in the group consisting of reflexes, voluntary muscle contractions, non-voluntary muscle contractions, a breathing system of said subject, an autonomous system of said subject for blood pressure regulation and an autonomous system of said subject for body temperature regulation.

Item 3: The method of item 1, wherein said physiological phenomenon is a repetitive physiological pulse generator.

Item 4: The method of any of items 1-3, wherein the step of processing involves filtering the measurement signal in the frequency domain.

Item 5: The method of any of items 1-4, wherein the step of processing involves filtering the measurement signal to remove frequencies above about 0.5 Hz. Alternatively or additionally, the step of processing may involve filtering the measurement signal to remove frequencies below about 3.5 Hz.

Item 6: The method of item 5, wherein the measurement signal is filtered with respect to at least one frequency range included in the group consisting of about 0.15 Hz to about 0.4 Hz, about 0.04 Hz to about 0.15 Hz, and about 0.001 Hz to about 0.1 Hz.

Item 7: The method of any of items 1-6, wherein the extracorporeal fluid system (S1) is associated with a mechanical pulse generator (3), wherein the pressure sensor (4a-4c) is arranged in the extracorporeal fluid system (S1) to detect a first pulse originating from the mechanical pulse generator (3) and a second pulse originating from said physiological phenomenon.

Item 8: The method of item 7, said method comprising: controlling the mechanical pulse generator (3) so as to separate the first and second pulses in the time and/or frequency domain.

Item 9: The method of item 7, said method comprising: intermittently turning off the mechanical pulse generator (3) while obtaining the measurement signal.

Item 10: The method of item 7, said method comprising: obtaining a first pulse profile (u(n)) which is a predicted temporal signal profile of the first pulse, and filtering the measurement signal in the time-domain, using the first pulse profile (u(n)), to essentially eliminate the first pulse while retaining the second pulse.

Item 11: The method of item 10, wherein the step of filtering comprises subtracting the first pulse profile (u(n)) from the measurement signal.

Item 12: The method of item 11, wherein step of subtracting comprises adjusting a phase of the first pulse profile (u(n)) in relation to the measurement signal, wherein said phase is indicated by phase information obtained from a phase sensor (26) coupled to the mechanical pulse generator (3), or from a control unit (23) for the mechanical pulse generator (3). The step of subtracting may also comprise adjusting an amplitude of the first pulse profile in relation to the measurement signal.

Item 13: The method of any one of items 10-12, wherein the first pulse profile (u(n)) is obtained in a reference measurement in said extracorporeal fluid system (S1), wherein the reference measurement comprises the steps of: operating the mechanical pulse generator (3) to generate at least one first pulse, and obtaining the first pulse profile (u(n)) from a reference signal generated by a reference pressure sensor (4a-4c) in the extracorporeal fluid system (S1).

Item 14: The method of item 13, wherein the mechanical pulse generator (3) is operated to generate a sequence of first pulses during the reference measurement, and wherein the first pulse profile (u(n)) is obtained by identifying and averaging a set of first pulse segments in the reference signal.

Item 15: The method of item 13 or 14, wherein the reference measurement is effected intermittently during operation of the extracorporeal fluid system (S1) to provide an updated first pulse profile (u(n)).

Item 16: The method of any one of items 13-15, wherein the pressure sensor (4a-4c) is used as said reference pressure sensor.

Item 17: The method of any one of items 10-12, wherein the step of obtaining comprises obtaining a predetermined signal profile.

Item 18: The method of item 17, wherein the step of obtaining further comprises modifying the predetermined signal profile according to a mathematical model based on a current value of one or more system parameters of the extracorporeal fluid system (S1).

Item 19: The method of any one of items 13-16, wherein the extracorporeal fluid system (S1) is operated, during the reference measurement, such that the reference signal contains a first pulse and no second pulse.

Item 20: The method of any one of items 13-16, wherein the reference measurement comprises: obtaining a combined pulse profile based on a first reference signal containing a first pulse and a second pulse; obtaining a second pulse profile based on a second reference signal containing a second pulse and no first pulse, and obtaining the predicted signal profile by subtracting the second pulse profile from the combined pulse profile.

Item 21: The method of item 20, further comprising the step of obtaining a current value of one or more system parameters of the extracorporeal fluid system (S1), wherein the first pulse profile (u(n)) is obtained as a function of the current value.

Item 22: The method of item 21, wherein said step of obtaining the first pulse profile (u(n)) comprises: identifying, based on the current value, one or more reference profiles ($r_1(n)$, $r_2(n)$) in a reference database; and obtaining the first pulse profile (u(n)) based on said one or more reference profiles ($r_1(n)$, $r_2(n)$).

Item 23: The method of item 22, wherein said one or more system parameters is indicative of the rate of first pulses in the extracorporeal fluid system (S1).

Item 24: The method of item 23, wherein the mechanical pulse generator (3) comprises a pumping device and the system parameter is indicative of a pump frequency of the pumping device.

Item 25: The method of any one of items 22-24, wherein each reference profile ($r_1(n)$, $r_2(n)$) in the reference database is obtained by a reference measurement in the extracorporeal fluid system (S1) for a respective value of said one or more system parameters.

Item 26: The method of item 21, wherein said step of obtaining the first pulse profile (u(n)) comprises: identifying, based on the current value, one or more combinations of energy and phase angle data in a reference database; and obtaining the first pulse profile (u(n)) based on said one or more combinations of energy and phase angle data.

Item 27: The method of item 26, wherein the first pulse profile (u(n)) is obtained by combining a set of sinusoids of different frequencies, wherein the amplitude and phase angle of each sinousoid is given by said one or more combinations of energy and phase angle data.

Item 28: The method of item 21, wherein said step of obtaining the first pulse profile (u(n)) comprises: inputting the current value into an algorithm which calculates the response of the pressure sensor (4a-4c) based on a mathematical model of the extracorporeal fluid system (S1).

Item 29: The method of any one of items 10-28, wherein the step of filtering comprises subtracting the first pulse profile (u(n)) from the measurement signal, and wherein the step of subtracting is preceded by an adjustment step, in which at least one of the amplitude, the time scale and the phase of the first pulse profile (u(n)) is adjusted with respect to the measurement signal.

Item 30: The method of item 29, wherein the adjustment step comprises minimizing a difference between the first pulse profile (u(n)) and the measurement signal.

Item 31: The method of items 10-28, wherein the step of filtering comprises: supplying the first pulse profile (u(n)) as input to an adaptive filter (30); calculating an error signal (e(n)) between the measurement signal and an output signal ($\hat{d}(n)$) of the adaptive filter (30); and providing the error signal (e(n)) as input to the adaptive filter (30), whereby the adaptive filter (30) is arranged to essentially eliminate the first pulse in the error signal (e(n)). Further, the adaptive filter (30) may generate the output signal as a linear combination of M shifted first pulse profiles, specifically with the linear combination being formed by the adaptive filter (30) adjusting the amplitude and phase of M instances of the first pulse profile.

Item 32: The method of item 31, wherein the adaptive filter (30) comprises a finite impulse response filter (32) with filter coefficients that operate on the first pulse profile (u(n)) to generate the output signal ($\hat{d}(n)$), and an adaptive algorithm (34) which optimizes the filter coefficients as a function of the error signal (e(n)) and the first pulse profile (u(n)).

Item 33: The method of item 31 or 32, further comprising the step of controlling the adaptive filter (30) to lock the filter coefficients, based on a comparison of the rate and/or amplitude of the second pulses to a limit value.

Item 34: The method of any of items 1-6, wherein said pressure data is a time-dependent monitoring signal including second pulses originating from said physiological phenomenon, said method further comprising: obtaining a reference pressure signal from a reference sensor in the extracorporeal fluid system (S1); identifying at least one second pulse in the reference pressure signal; calculating an estimated difference in arrival time between the reference sensor and said at least one pressure sensor (4a-4c) based on a difference in fluid pressure between the location of the reference sensor and said at least one pressure sensor (4a-4c); and processing the monitoring signal based on the estimated difference in arrival time.

Item 35: The method of item 34, further comprising the steps of calculating a magnitude value indicative of the magnitude of said at least one second pulse in the reference pressure signal, and comparing the magnitude value to a limit, wherein the step of calculating an estimated difference in arrival time is conditioned upon said step of comparing.

Item 36: The method of any of items 1-35, wherein said processing involves one or more of detecting, tracking and predicting a disordered condition of the subject using said pressure data.

Item 37: The method of item 36, wherein the disordered condition comprises one or more of sneezing, hiccups, vomiting, coughing, blood pressure turbulence, ectopic beats, lack of autonomous regulation, hypotension, disordered breathing, sleep apnea, periodic breathing, hyperventilation, asthmatic attacks, dyspnea, and Cheyne-Stokes respiration.

Item 38: The method of item 36 or 37, wherein said pressure data is a time-dependent monitoring signal including second pulses originating from said physiological phenomenon, said method further comprising: obtaining timing information indicative of the timing of the second pulses in the monitoring signal; processing the monitoring signal based on the timing information, to calculate a parameter value indicative of the second pulses; and analysing the parameter value for detection of the disordered condition.

Item 39: The method of any one of items 1-6, further comprising monitoring the integrity of a fluid connection between said extracorporeal fluid system (S1) and said vascular system (S2) based on said pressure data.

Item 40: The method of item 39, wherein the extracorporeal fluid system (S1) is associated with a mechanical pulse generator (3), wherein the pressure sensor (4a-4c) is arranged in the extracorporeal fluid system (S1) to detect a first pulse originating from the mechanical pulse generator (3) and a second pulse originating from said physiological phenomenon, and wherein said pressure data is a time-dependent monitoring signal including second pulses originating from said physiological phenomenon, said method further comprising calculating a parameter value based on signal values within a time window in the monitoring signal, the parameter value representing a distribution of the signal values; and determining the integrity of the fluid connection (C) based at least partly on the parameter value.

Item 41: The method of item 40, wherein said calculating comprises: calculating the parameter value as a statistical dispersion measure of the signal values within the time window.

Item 42: The method of item 41, wherein the statistical dispersion measure includes at least one of: a standard deviation, a variance, a coefficient of variation, a sum of differences, an energy, a power, a sum of absolute deviations from an average value, and an average of absolute differences from an average value.

Item 43: The method of item 40, wherein said calculating comprises: matching the signal values within the time window to a predicted temporal signal profile of a second pulse.

Item 44: The method of item 43, wherein the parameter value is a correlation value resulting from said matching.

Item 45: The method of item 43 or 44, wherein said calculating comprises: calculating a cross-correlation between the signal values within the time window and the predicted temporal signal profile; and identifying a maximum correlation value in the cross-correlation; wherein said determining comprises: comparing the maximum correlation value to a threshold value.

Item 46: The method of item 45, wherein said calculating comprises: obtaining a time point of the maximum correlation value, and validating the maximum correlation value by comparing the time point to a predicted time point.

Item 47: The method of any one of items 43-46, further comprising the step of obtaining a reference pressure signal from a reference sensor (4a-4c) in the extracorporeal fluid system (S1), wherein the reference sensor (4a-4c) is arranged to detect said second pulses even if the fluid connection (C) is compromised, and calculating the predicted temporal signal profile based on the reference pressure signal.

Item 48: The method of item 47, further comprising the steps of calculating a magnitude value indicative of the magnitude of the physiological pulses in the reference pressure signal, and comparing the magnitude value to a limit, wherein the step of calculating the predicted temporal signal profile based on the reference pressure signal is conditioned upon said step of comparing.

Item 49: The method of item 47 or 48, wherein the step of calculating the predicted temporal signal profile comprises adjusting for a difference in transit time between the reference sensor and said at least one pressure sensor (4a-4c).

Item 50: The method of item 49, wherein said difference in transit time is given by a predefined value.

Item 51: The method of item 49, wherein said difference in transit time is calculated based on a difference in fluid pressure between the location of the reference sensor and said at least one pressure sensor (4a-4c).

Item 52: The method of any one of items 40-51, wherein the time window is selected so as to contain at least one second pulse.

Item 53: The method of item 52, wherein the length of the time window is chosen to exceed a maximum pulse repetition interval of said physiological phenomenon.

Item 54: The method of item 52 or 53, wherein the time window is chosen based on timing information indicative of the timing of the second pulses in the monitoring signal.

Item 55: The method of any one of items 40-54, wherein a step of generating the monitoring signal comprises: filtering the measurement signal to remove the first pulses; deriving, based on timing information indicative of the timing of the second pulses in the measurement signal, a set of signal segments in the thus-filtered measurement signal(s); and aligning and adding the signal segments, based on the timing information.

Item 56: The method of any one of items 40-55, wherein said calculating comprises: identifying a candidate second pulse in the monitoring signal and a corresponding candidate time point; and validating the candidate second pulse based on the candidate time point in relation to timing information indicative of the timing of the second pulses in the monitoring signal.

Item 57: The method of any one of items 54-56, wherein the timing information is obtained from a pulse sensor coupled to the subject.

Item 58: The method of any one of items 54-56, wherein the timing information is obtained as a function of the relative timing of second pulses identified based on preceding parameter values.

Item 59: The method of any one of items 54-56, wherein the extracorporeal fluid system (S1) is an extracorporeal blood flow circuit (20) comprising an arterial access device (1), a blood processing device (6), and a venous access device (14), wherein vascular system (S2) comprises a blood vessel access, wherein the arterial access device (1) is connected to the vascular system (S2), wherein the venous access device (14) is connected to the blood vessel access to form the fluid connection (C), wherein the mechanical pulse generator (3) comprises a pumping device arranged in the extracorporeal blood flow circuit (20) to pump blood from the arterial access device (1) through the blood processing device (6) to the venous access device (14), wherein the monitoring signal is generated based on a venous measurement signal obtained from a venous pressure sensor (4c) located downstream of the pumping device (3), said method comprising: obtaining an arterial measurement signal from an arterial pressure sensor (4a) located upstream of the pumping device (3), identifying at least one second pulse in the arterial measurement signal; and calculating the timing information from the thus-identified second pulse(s).

Item 60: The method of any one of items 54-56, further comprising: intermittently turning off the mechanical pulse generator (3); identifying at least one second pulse in the monitoring signal; and calculating the timing information from the thus-identified second pulse.

Item 61: The method of any one of items 54-56, further comprising: identifying a set of candidate second pulses in the monitoring signal; deriving a sequence of candidate time points based on the set of candidate second pulses; validating the sequence of candidate time points against a temporal criterion; and calculating the timing information as a function of the thus-validated sequence of candidate time points.

Item 62: The method of item 39, wherein the extracorporeal fluid system (S1) is an extracorporeal blood processing system (20) comprising an access device (1, 14), wherein the vascular system (S2) comprises a blood vessel access, and wherein a connection between the access device (1, 14) and the blood vessel access forms the fluid connection (C).

Item 63: The method of item 39, wherein said pressure data is a time-dependent monitoring signal including second pulses originating from said physiological phenomenon, said method further comprising: obtaining timing information indicative of the timing of the second pulses in the monitoring signal; processing the monitoring signal based on the timing information, to calculate a parameter value indicative of presence or absence of the second pulses; and determining the integrity of the fluid connection (C) based at least partly on the parameter value.

Item 64: The method of item 63, wherein said processing comprises: locating a time window in the monitoring signal, based on the timing information; and calculating the parameter value based on the signal values within said time window.

Item 65: The method of item 64, wherein said processing further comprises: selecting the length of the time window based on the timing information.

Item 66: The method of any one of items 63-65, wherein the extracorporeal fluid system (S1) is associated with a mechanical pulse generator (3) that generates first pulses in the extracorporeal fluid system (S1), and wherein a step of generating the monitoring signal comprises: filtering the measurement signal to remove the first pulses.

Item 67: The method of item 66, wherein the step of generating the monitoring signal further comprises: selecting a set of signal segments in the thus-filtered measurement signal; and aligning and adding the signal segments, based on the timing information.

Item 68: The method of item 66 or 67, wherein said calculating comprises: identifying a candidate second pulse in the monitoring signal and a corresponding candidate time point; and validating the candidate second pulse based on the candidate time point in relation to the timing information.

Item 69: The method of any one of items 63-68, wherein the timing information is obtained from a pulse sensor coupled to the subject.

Item 70: The method of any one of items 63-68, wherein the timing information is obtained as a function of the relative timing of second pulses identified based on preceding parameter values.

Item 71: The method of any one of items 63-68, further comprising the step of obtaining a reference pressure signal from a reference sensor (4a-4c) in the extracorporeal fluid system (S1), wherein the reference sensor (4a-4c) is arranged to detect said second pulses even if the fluid connection (C) is compromised, and wherein said step of obtaining the timing information comprises: identifying at least one second pulse in the reference pressure signal and obtaining an estimated difference in arrival time between the reference sensor and said at least one pressure sensor (4a-4c).

Item 72: The method of item 71, wherein the estimated difference in arrival time is given by a predefined value.

Item 73: The method of item 71, wherein the estimated difference in arrival time is calculated based on a difference in fluid pressure between the location of the reference sensor and said at least one pressure sensor (4a-4c).

Item 74: The method of item 71, further comprising the steps of calculating a magnitude value indicative of the magnitude of said at least one second pulse in the reference pressure signal, and comparing the magnitude value to a limit, wherein the step of calculating an estimated difference in arrival time is conditioned upon said step of comparing.

Item 75: The method of any one of items 66-68, wherein the extracorporeal fluid system (S1) is an extracorporeal blood flow circuit comprising an arterial access device (1), a blood processing device (6), and a venous access device (14), wherein the vascular system (S2) comprises a blood vessel access, wherein the arterial access device (1) is connected to the vascular system (S2), wherein the venous access device (14) is connected to the blood vessel access to form the fluid connection (C), wherein the mechanical pulse generator (3) comprises a pumping device arranged in the extracorporeal blood flow circuit (20) to pump blood from the arterial access device (1) through the blood processing device (6) to the venous access device (14), wherein the monitoring signal is generated based on a venous measurement signal obtained from a venous pressure sensor (4c) located downstream of the pumping device (3), said method comprising: obtaining an arterial measurement signal from an arterial pressure sensor (4a) located upstream of the pumping device (3), identifying at least one second pulse in the arterial measurement signal; and calculating the timing information from the thus-identified second pulse(s).

Item 76: The method of any one of items 66-68, further comprising: intermittently turning off the mechanical pulse generator (3); identifying at least one second pulse in the monitoring signal; and calculating the timing information from the thus-identified second pulse.

Item 77: The method of any one of items 66-68, further comprising: identifying a set of candidate second pulses in the monitoring signal; deriving a sequence of candidate time points based on the set of candidate second pulses; validating the sequence of candidate time points against a temporal criterion; and calculating the timing information as a function of the thus-validated sequence of candidate time points.

Item 78: The method of item 63, wherein said obtaining further comprises: identifying a set of candidate second pulses in the monitoring signal; deriving a sequence of candidate time points based on the set of candidate second pulses; generating a set of validated candidate second pulses by validating the sequence of candidate time points against a temporal criterion; wherein said processing comprises:

calculating a set of average representations, each average representation being formed by aligning and adding signal segments of the monitoring signal that correspond to a unique combination of validated candidate second pulses; and calculating the parameter value for each of said average representations; and wherein said determining comprises comparing a maximum parameter value to a threshold value.

Item 79: The method of any one of items 63-66, wherein the parameter value represents a distribution of signal values.

Item 80: The method of any one of items 39-79, further comprising the step of processing the measurement signal for identification of heart data originating from heart beats of said subject, and wherein the integrity of the fluid connection is determined based on said pressure data and said heart data.

Item 100: A computer program product comprising instructions for causing a computer to perform the method of any one of items 1-80.

Item 200: A device for processing a measurement signal obtained by a pressure sensor (4a-4c) in an extracorporeal fluid system (S1) connected to a vascular system (S2) of a subject, said device comprising: an input (28) for receiving the measurement signal; and a signal processor (25) connected to said input (28) and configured to process the measurement signal according to any one of items 1-80.

Item 300: A device for processing a measurement signal obtained by a pressure sensor (4a-4c) in an extracorporeal fluid system (S1) connected to a vascular system (S2) of a subject, said device comprising: means (28) for receiving the measurement signal; and means (29) for processing the measurement signal for identification of pressure data originating from a first physiological phenomenon in said subject, said physiological phenomenon excluding the heart of said subject.

Item 301: The device of item 300, wherein said physiological phenomenon is included in the group consisting of reflexes, voluntary muscle contractions, non-voluntary muscle contractions, a breathing system of said subject, an autonomous system of said subject for blood pressure regulation and an autonomous system of said subject for body temperature regulation.

Item 302: The device of item 300, wherein said physiological phenomenon is a repetitive physiological pulse generator.

Item 303: The device of any of items 300-302, wherein the means (29) for processing is configured to filter the measurement signal in the frequency domain.

Item 304: The device of any of items 300-303, wherein the means (29) for processing is configured to filter the measurement signal to remove frequencies above about 0.5 Hz. Alternatively or additionally, the means (29) for processing may be configured to filter the measurement signal to remove frequencies below about 3.5 Hz.

Item 305: The device of item 304, wherein the means (29) for filtering is configured filter the measurement signal with respect to at least one frequency range included in the group consisting of about 0.15 Hz to about 0.4 Hz, about 0.04 Hz to about 0.15 Hz, and about 0.001 Hz to about 0.1 Hz.

Item 306: The device of any of items 300-305, wherein the extracorporeal fluid system (S1) is associated with a mechanical pulse generator (3), wherein the pressure sensor (4a-4c) is arranged in the extracorporeal fluid system (S1) to detect a first pulse originating from the mechanical pulse generator (3) and a second pulse originating from said physiological phenomenon.

Item 307: The device of item 306, further comprising means (23, 28, 29) for controlling the mechanical pulse generator (3) so as to separate the first and second pulses in the time and/or frequency domain.

Item 308: The device of item 306, further comprising means (23, 28, 29) for intermittently turning off the mechanical pulse generator (3) while obtaining the measurement signal.

Item 309: The device of item 306, further comprising means (29) for obtaining a first pulse profile (u(n)) which is a predicted temporal signal profile of the first pulse, and means (29) for filtering the measurement signal in the time-domain, using the first pulse profile (u(n)), to essentially eliminate the first pulse while retaining the second pulse.

Item 310: The device of item 309, wherein the means (29) of filtering is configured to subtract the first pulse profile (u(n)) from the measurement signal.

Item 311: The device of item 310, wherein the means (29) for filtering is configured to subtract the first pulse profile (u(n)) by adjusting a phase of the first pulse profile (u(n)) in relation to the measurement signal, wherein said phase is indicated by phase information obtained from a phase sensor (26) coupled to the mechanical pulse generator (3), or from a control unit (23) for the mechanical pulse generator (3). The means (29) for filtering may also be configured to adjust an amplitude of the first pulse profile in relation to the measurement signal.

Item 312: The device of any one of items 309-311, further comprising reference measurement means (29) for obtaining the first pulse profile (u(n)) in a reference measurement in said extracorporeal fluid system (S1), wherein the reference measurement means (29) is configured to, while the mechanical pulse generator (3) is operated to generate at least one first pulse, obtain the first pulse profile (u(n)) from a reference signal generated by a reference pressure sensor (4a-4c) in the extracorporeal fluid system (S1).

Item 313: The device of item 312, wherein the mechanical pulse generator (3) is operated to generate a sequence of first pulses during the reference measurement, and wherein reference measurement means (29) is configured to obtain the first pulse profile (u(n)) by identifying and averaging a set of first pulse segments in the reference signal.

Item 314: The device of item 312 or 313, wherein reference measurement means (29) is configured to intermittently effect the reference measurement during operation of the extracorporeal fluid system (S1) to provide an updated first pulse profile (u(n)).

Item 315: The device of any one of items 312-314, wherein the pressure sensor (4a-4c) is used as said reference pressure sensor.

Item 316: The device of any one of items 309-311, wherein the means (29) for obtaining a first pulse profile is configured to obtain a predetermined signal profile.

Item 317: The device of item 316, wherein the means (29) for obtaining a first pulse profile is further configured to modify the predetermined signal profile according to a mathematical model based on a current value of one or more system parameters of the extracorporeal fluid system (S1).

Item 318: The device of any one of items 312-315, wherein the extracorporeal fluid system (S1) is operated, during the reference measurement, such that the reference signal contains a first pulse and no second pulse.

Item 319: The device of any one of items 312-315, wherein the reference measurement means (29) is configured to: obtain a combined pulse profile based on a first reference signal containing a first pulse and a second pulse;

obtain a second pulse profile based on a second reference signal containing a second pulse and no first pulse; and obtain the predicted signal profile by subtracting the second pulse profile from the combined pulse profile.

Item 320: The device of item 319, further comprising means (28, 29) for obtaining a current value of one or more system parameters of the extracorporeal fluid system (S1), wherein the means (29) for obtaining a first pulse profile is configured to obtain the first pulse profile (u(n)) as a function of the current value.

Item 321: The device of item 320, wherein the means (29) for obtaining a first pulse profile (u(n)) is configured to: identify, based on the current value, one or more reference profiles $(r_1)(n), r_2(n))$ in a reference database; and obtain the first pulse profile (u(n)) based on said one or more reference profiles $(r_1)(n), r_2(n))$.

Item 322: The device of item 321, wherein said one or more system parameters is indicative of the rate of first pulses in the extracorporeal fluid system (S1).

Item 323: The device of item 322, wherein the mechanical pulse generator (3) comprises a pumping device and the system parameter is indicative of a pump frequency of the pumping device.

Item 324: The device of any one of items 321-323, wherein each reference profile $(r_1)(n), r_2(n))$ in the reference database is obtained by a reference measurement in the extracorporeal fluid system (S1) for a respective value of said one or more system parameters.

Item 325: The device of item 320, wherein the means (29) for obtaining a first pulse profile (u(n)) is configured to: identify, based on the current value, one or more combinations of energy and phase angle data in a reference database; and obtain the first pulse profile (u(n)) based on said one or more combinations of energy and phase angle data.

Item 326: The device of item 325, wherein the means (29) for obtaining a first pulse profile (u(n)) is configured to obtain the first pulse profile (u(n)) by combining a set of sinusoids of different frequencies, wherein the amplitude and phase angle of each sinusoid is given by said one or more combinations of energy and phase angle data.

Item 327: The device of item 320, wherein the means (29) for obtaining a first pulse profile (u(n)) is configured to: input the current value into an algorithm which calculates the response of the pressure sensor (4a-4c) based on a mathematical model of the extracorporeal fluid system (S1).

Item 328: The device of any one of items 309-327, wherein the means (29) for filtering is configured to adjust at least one of the amplitude, the time scale and the phase of the first pulse profile (u(n)) with respect to the measurement signal and to subtract the thus-adjusted first pulse profile (u(n)) from the measurement signal.

Item 329: The device of item 328, wherein the means (29) for filtering is configured to adjust by minimizing a difference between the first pulse profile (u(n)) and the measurement signal.

Item 330: The device of items 309-327, wherein the means (29) for filtering is configured to: supply the first pulse profile (u(n)) as input to an adaptive filter (30); calculate an error signal (e(n)) between the measurement signal and an output signal (d(n)) of the adaptive filter (30); and provide the error signal (e(n)) as input to the adaptive filter (30), whereby the adaptive filter (30) is arranged to essentially eliminate the first pulse in the error signal (e(n)). Further, the adaptive filter (30) may be configured to generate the output signal as a linear combination of M shifted first pulse profiles, and specifically the adaptive filter (30) may be configured to linearly combine M instances of the first pulse profile, which are properly adjusted in amplitude and phase by the adaptive filter (30).

Item 331: The device of item 330, wherein the adaptive filter (30) comprises a finite impulse response filter (32) with filter coefficients that operate on the first pulse profile (u(n)) to generate the output signal (d̂(n)), and an adaptive algorithm (34) which optimizes the filter coefficients as a function of the error signal (e(n)) and the first pulse profile (u(n)).

Item 332: The device of item 330 or 331, further comprising means (29) for controlling the adaptive filter (30) to lock the filter coefficients, based on a comparison of the rate and/or amplitude of the second pulses to a limit value.

Item 333: The device of any of items 300-305, wherein said pressure data is a time-dependent monitoring signal including second pulses originating from said physiological phenomenon, said device further comprising: means (28) for obtaining a reference pressure signal from a reference sensor in the extracorporeal fluid system (S1); means (29) for identifying at least one second pulse in the reference pressure signal; means (29) for calculating an estimated difference in arrival time between the reference sensor and said at least one pressure sensor (4a-4c) based on a difference in fluid pressure between the location of the reference sensor and said at least one pressure sensor (4a-4c); and means (29) for processing the monitoring signal based on the estimated difference in arrival time.

Item 334: The device of item 333, further comprising means (29) for calculating a magnitude value indicative of the magnitude of said at least one second pulse in the reference pressure signal, and comparing the magnitude value to a limit, wherein the calculating an estimated difference in arrival time is conditioned upon the comparing.

Item 335: The device of any of items 300-334, wherein the means (29) for processing is configured to perform one or more of detecting, tracking and predicting a disordered condition of the subject using said pressure data.

Item 336: The device of item 335, wherein the disordered condition comprises one or more of sneezing, hiccups, vomiting, coughing, blood pressure turbulence, ectopic beats, lack of autonomous regulation, hypotension, disordered breathing, sleep apnea, periodic breathing, hyperventilation, asthmatic attacks, dyspnea, and Cheyne-Stokes respiration.

Item 337: The device of item 335 or 336, wherein said pressure data is a time-dependent monitoring signal including second pulses originating from said physiological phenomenon, said device further comprising: means (29) for obtaining timing information indicative of the timing of the second pulses in the monitoring signal; means (29) for processing the monitoring signal based on the timing information, to calculate a parameter value indicative of the second pulses; and means (29) for analysing the parameter value for detection of the disordered condition.

Item 338: The device of any one of items 300-305, further comprising means (29) for monitoring the integrity of a fluid connection between said extracorporeal fluid system (S1) and said vascular system (S2) based on said pressure data.

Item 339: The device of item 338, wherein the extracorporeal fluid system (S1) is associated with a mechanical pulse generator (3), wherein the pressure sensor (4a-4c) is arranged in the extracorporeal fluid system (S1) to detect a first pulse originating from the mechanical pulse generator (3) and a second pulse originating from said first physiological phenomenon, and wherein said pressure data is a time-dependent monitoring signal including second pulses originating from said physiological phenomenon, said device further comprising means (29) for calculating a parameter value based on signal values within a time window in the monitoring signal, the parameter value representing a distribution of the signal values; and means (29) for determining the integrity of the fluid connection (C) based at least partly on the parameter value.

Item 340: The device of item 339, wherein the means (29) for calculating a parameter value is configured to: calculate the parameter value as a statistical dispersion measure of the signal values within the time window.

Item 341: The device of item 340, wherein the statistical dispersion measure includes at least one of: a standard deviation, a variance, a coefficient of variation, a sum of differences, an energy, a power, a sum of absolute deviations from an average value, and an average of absolute differences from an average value.

Item 342: The device of item 339, wherein the means (29) for calculating a parameter value is configured to: match the signal values within the time window to a predicted temporal signal profile of a second pulse.

Item 343: The device of item 342, wherein the parameter value is a correlation value resulting from said matching.

Item 344: The device of item 342 or 343, wherein the means (29) for calculating a parameter value is configured to: calculate a cross-correlation between the signal values within the time window and the predicted temporal signal profile; and identify a maximum correlation value in the cross-correlation; wherein the means (29) for determining the integrity is configured to: compare the maximum correlation value to a threshold value.

Item 345: The device of item 344, wherein the means (29) for calculating a parameter value is configured to: obtain a time point of the maximum correlation value, and validate the maximum correlation value by comparing the time point to a predicted time point.

Item 346: The device of any one of items 342-345, further comprising means (29) for obtaining a reference pressure signal from a reference sensor (4a-4c) in the extracorporeal fluid system (S1), and means (29) for calculating the predicted temporal signal profile based on the reference pressure signal, wherein the reference sensor (4a-4c) is arranged to detect said second pulses even if the fluid connection (C) is compromised.

Item 347: The device of item 346, further comprising means (29) for calculating a magnitude value indicative of the magnitude of the physiological pulses in the reference pressure signal, and comparing the magnitude value to a limit, wherein the operation of the means (29) for calculating the predicted temporal signal profile based on the reference pressure signal is conditioned upon said comparing.

Item 348: The device of item 346 or 347, wherein the means (29) for calculating the predicted temporal signal profile is configured to adjust for a difference in transit time between the reference sensor and said at least one pressure sensor (4a-4c).

Item 349: The device of item 348, wherein said difference in transit time is given by a predefined value.

Item 350: The device of item 348, wherein said difference in transit time is calculated based on a difference in fluid pressure between the location of the reference sensor and said at least one pressure sensor (4a-4c).

Item 351: The device of any one of items 339-350, wherein the time window is selected so as to contain at least one second pulse.

Item 352: The device of item 351, wherein the length of the time window is chosen to exceed a maximum pulse repetition interval of said first physiological phenomenon.

Item 353: The device of item 351 or 352, wherein the time window is chosen based on timing information indicative of the timing of the second pulses in the monitoring signal.

Item 354: The device of any one of items 339-353, further comprising means (29) for generating the monitoring signal which is configured to generate the monitoring signal by: filtering the measurement signal to remove the first pulses; deriving, based on timing information indicative of the timing of the second pulses in the measurement signal, a set of signal segments in the thus-filtered measurement signal(s); and aligning and adding the signal segments, based on the timing information.

Item 355: The device of any one of items 339-354, wherein the means (29) for calculating a parameter value is configured to: identify a candidate second pulse in the monitoring signal and a corresponding candidate time point; and validate the candidate second pulse based on the candidate time point in relation to timing information indicative of the timing of the second pulses in the monitoring signal.

Item 356: The device of any one of items 353-355, further comprising means (28, 29) for obtaining the timing information from a pulse sensor coupled to the subject.

Item 357: The device of any one of items 353-355, further comprising means (29) for obtaining the timing information as a function of the relative timing of second pulses identified based on preceding parameter values.

Item 358: The device of any one of items 353-355, wherein the extracorporeal fluid system (S1) is an extracorporeal blood flow circuit (20) comprising an arterial access device (1), a blood processing device (6), and a venous access device (14), wherein vascular system (S2) comprises a blood vessel access, wherein the arterial access device (1) is connected to the vascular system (S2), wherein the venous access device (14) is connected to the blood vessel access to form the fluid connection (C), wherein the mechanical pulse generator (3) comprises a pumping device arranged in the extracorporeal blood flow circuit (20) to pump blood from the arterial access device (1) through the blood processing device (6) to the venous access device (14), wherein the monitoring signal is generated based on a venous measurement signal obtained from a venous pressure sensor (4c) located downstream of the pumping device (3). The device may further comprise means (28) for obtaining an arterial measurement signal from an arterial pressure sensor (4a) located upstream of the pumping device (3); means (29) for identifying at least one second pulse in the arterial measurement signal; and means (29) for calculating the timing information from the thus-identified second pulse(s).

Item 359: The device of any one of items 353-355, further comprising: means (23, 28, 29) for intermittently turning off the mechanical pulse generator (3); means (29) for identifying at least one second pulse in the monitoring signal; and means (29) for calculating the timing information from the thus-identified second pulse.

Item 360: The device of any one of items 353-355, further comprising: means (29) for identifying a set of candidate second pulses in the monitoring signal; means (29) for deriving a sequence of candidate time points based on the set of candidate second pulses; means (29) for validating the sequence of candidate time points against a temporal criterion; and means (29) for calculating the timing information as a function of the thus-validated sequence of candidate time points.

Item 361: The device of item 338, wherein the extracorporeal fluid system (S1) is an extracorporeal blood processing system (20) comprising an access device (1, 14), wherein the vascular system (S2) comprises a blood vessel access, and wherein a connection between the access device (1, 14) and the blood vessel access forms the fluid connection (C).

Item 362: The device of item 338, wherein said pressure data is a time-dependent monitoring signal including second pulses originating from said physiological phenomenon, said device further comprising: means (29) for obtaining timing information indicative of the timing of the second pulses in the monitoring signal; means (29) for processing the monitoring signal based on the timing information, to calculate a parameter value indicative of presence or absence of the second pulses; and means (29) for determining the integrity of the fluid connection (C) based at least partly on the parameter value.

Item 363: The device of item 362, wherein the means (29) for processing the monitoring signal is configured to: locate a time window in the monitoring signal, based on the timing information; and calculate the parameter value based on the signal values within said time window.

Item 364: The device of item 363, wherein the means (29) for processing the monitoring signal is further configured to: select the length of the time window based on the timing information.

Item 365: The device of any one of items 362-364, wherein the extracorporeal fluid system (S1) is associated with a mechanical pulse generator (3) that generates first pulses in the extracorporeal fluid system (S1), and wherein the device further comprises means (29) for generating the monitoring signal by filtering the measurement signal to remove the first pulses.

Item 366: The device of item 365, wherein the means (29) for generating the monitoring signal is further configured to: select a set of signal segments in the thus-filtered measurement signal; and align and add the signal segments, based on the timing information.

Item 367: The device of item 365 or 366, wherein the means (29) for processing the monitoring signal is configured to: identify a candidate second pulse in the monitoring signal and a corresponding candidate time point; and validate the candidate second pulse based on the candidate time point in relation to the timing information.

Item 368: The device of any one of items 362-367, wherein the means (28, 29) for obtaining timing information is configured to obtain the timing information from a pulse sensor coupled to the subject.

Item 369: The device of any one of items 362-367, wherein the means (29) for obtaining timing information is configured to obtain the timing information as a function of the relative timing of second pulses identified based on preceding parameter values.

Item 370: The device of any one of items 362-367, further comprising means (28) for obtaining a reference pressure signal from a reference sensor (4a-4c) in the extracorporeal fluid system (S1), wherein the reference sensor (4a-4c) is arranged to detect said second pulses even if the fluid connection (C) is compromised, and wherein the means (29) for obtaining timing information is configured to: identify at least one second pulse in the reference pressure signal and obtain an estimated difference in arrival time between the reference sensor and said at least one pressure sensor (4a-4c).

Item 371: The device of item 370, wherein the estimated difference in arrival time is given by a predefined value.

Item 372: The device of item 370, wherein the estimated difference in arrival time is calculated based on a difference in fluid pressure between the location of the reference sensor and said at least one pressure sensor (4a-4c).

Item 373: The device of item 370, further comprising means (29) for calculating a magnitude value indicative of the magnitude of said at least one second pulse in the reference pressure signal, and comparing the magnitude value to a limit, wherein the calculating of an estimated difference in arrival time is conditioned upon said comparing.

Item 374: The device of any one of items 365-367, wherein the extracorporeal fluid system (S1) is an extracorporeal blood flow circuit comprising an arterial access device (1), a blood processing device (6), and a venous access device (14), wherein the vascular system (S2) comprises a blood vessel access, wherein the arterial access device (1) is connected to the vascular system (S2), wherein the venous access device (14) is connected to the blood vessel access to form the fluid connection (C), wherein the mechanical pulse generator (3) comprises a pumping device arranged in the extracorporeal blood flow circuit (20) to pump blood from the arterial access device (1) through the blood processing device (6) to the venous access device (14), wherein the monitoring signal is generated based on a venous measurement signal obtained from a venous pressure sensor (4c) located downstream of the pumping device (3), said device comprising: means (28) for obtaining an arterial measurement signal from an arterial pressure sensor (4a) located upstream of the pumping device (3); means (29) for identifying at least one second pulse in the arterial measurement signal; and means (29) for calculating the timing information from the thus-identified second pulse(s).

Item 375: The device of any one of items 365-367, further comprising means (23, 28, 29) for intermittently turning off the mechanical pulse generator (3); means (29) for identifying at least one second pulse in the monitoring signal; and means (29) for calculating the timing information from the thus-identified second pulse.

Item 376: The device of any one of items 365-367, further comprising means (29) for identifying a set of candidate second pulses in the monitoring signal; means (29) for deriving a sequence of candidate time points based on the set of candidate second pulses; means (29) for validating the sequence of candidate time points against a temporal criterion; and means (29) for calculating the timing information as a function of the thus-validated sequence of candidate time points.

Item 377: The device of item 362, wherein the means (29) for obtaining timing information is configured to: identify a set of candidate second pulses in the monitoring signal; derive a sequence of candidate time points based on the set of candidate second pulses; generate a set of validated candidate second pulses by validating the sequence of candidate time points against a temporal criterion; wherein the means (29) for processing the monitoring signal is configured to: calculate a set of average representations, each average representation being formed by aligning and adding signal segments of the monitoring signal that correspond to a unique combination of validated candidate second pulses; and calculate the parameter value for each of said average representations; and wherein the means (29) for determining the integrity is configured to compare a maximum parameter value to a threshold value.

Item 378: The device of any one of items 362-365, wherein the parameter value represents a distribution of signal values.

Item 379: The device of any one of items 338-378, further comprising means (29) for processing the measurement signal for identification of heart data originating from heart beats of said subject, and wherein the means (29) for determining the integrity of the fluid connection is configured to determine the integrity based on said pressure data and said heart data.

This section makes reference to FIGS. 12-23(b) and describes a method and device for processing a time-dependent measurement signal.

Figure 12:
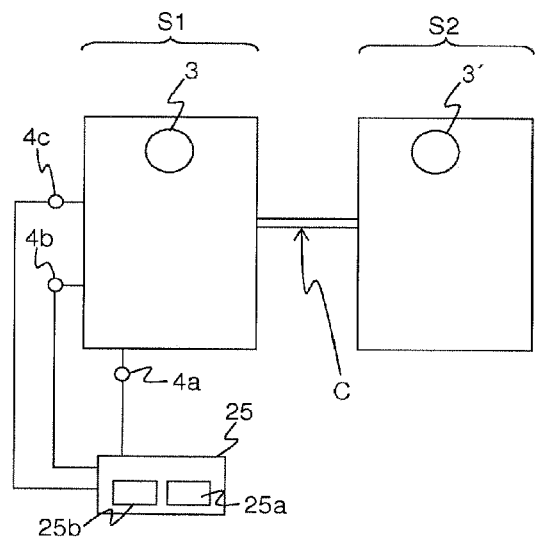
FIG. 12 is a schematic view of a general fluid containing system in which the inventive data processing may be used for filtering a pressure signal.

FIG. 12 illustrates a fluid containing system in which a fluid connection C is established between a first fluid containing sub-system S1 and a second fluid containing sub-system S2. The fluid connection C may or may not transfer fluid from one sub-system to the other. A first pulse generator 3 is arranged to generate a series of pressure waves in the fluid within the first sub-system S1, and a second pulse generator 3' is arranged to generate a series of pressure waves in the fluid within the second sub-system S2. A pressure sensor 4a is arranged to measure the fluid pressure in the first sub-system S1. Pressure waves generated by the second pulse generator 3' will travel from the second sub-system S2 to the first sub-system S1, via the connection C, and thus second pulses originating from the second pulse generator 3' will be detected by the pressure sensor 4a in addition to first pulses originating from the first pulse generator 3. It is to be noted that either one of the first and second pulse generators 3, 3' may include more than one pulse-generating device. Further, any such pulse-generating device may or may not be part of the respective sub-system S1, S2.

The system of FIG. 12 further includes a surveillance device 25 which is connected to the pressure sensor 4a, and possibly to one or more additional pressure sensors 4b, 4c, as indicated in FIG. 12. Thereby, the surveillance device 25 acquires one or more pressure signals that are time-dependent to provide a real time representation of the fluid pressure in the first sub-system S1.

Generally, the surveillance device 25 is configured to monitor a functional state or functional parameter of the fluid containing system, by isolating and analysing one or more second pulses in one of the pressure signals. As will be further exemplified in the following, the functional state or parameter may be monitored to identify a fault condition, e.g. in the first or second sub-systems S1, S2, the second pulse generator 3' or the fluid connection C. Upon identification of a fault condition, the surveillance device 25 may issue an alarm or warning signal and/or alert a control system of the first or second sub-systems S1, S2 to take appropriate action. Alternatively or additionally, the surveillance device 25 may be configured to record or output a time sequence of values of the functional state or parameter.

Depending on implementation, the surveillance device 25 may use digital components or analog components, or a combination thereof, for receiving and processing the pressure signal. The device 25 may thus be a computer, or a similar data processing device, with adequate hardware for acquiring and processing the pressure signal in accordance with different embodiments of the invention. Embodiments of the invention may e.g. be implemented by software instructions that are supplied on a computer-readable medium for execution by a processor 25a in conjunction with a memory unit 25b in the computer.

Typically, the surveillance device 25 is configured to continuously process the time-dependent pressure signal(s) to isolate any second pulses. This processing is schematically depicted in the flow chart of FIG. 13. The illustrated processing involves a step 201 of obtaining a first pulse profile u(n) which is a predicted temporal signal profile of the first pulse(s), and a step 202 of filtering the pressure signal d(n), or a pre-processed version thereof, in the time-domain, using the first pulse profile u(n), to essentially eliminate or cancel the first pulse(s) while retaining the second pulse(s) contained in d(n). In the context of the present disclosure, n indicates a sample number and is thus equivalent to a (relative) time point in a time-dependent signal. In step 203, the resulting filtered signal e(n) is then analysed for the purpose of monitoring the aforesaid functional state or parameter.

The first pulse profile is a shape template or standard signal profile, typically given as a time-sequence of data values, which reflects the shape of the first pulse in the time domain. The first pulse profile is also denoted "predicted signal profile" in the following description.

By "essentially eliminating" is meant that the first pulse(s) is(are) removed from the pressure signal to such an extent that the second pulse(s) can be detected and analysed for the purpose of monitoring the aforesaid functional state or parameter.

By filtering the pressure signal in the time-domain, using the first pulse profile, it is possible to essentially eliminate the first pulses and still retain the second pulses, even if the first and second pulses overlap or nearly overlap in the frequency domain. Such a frequency overlap is not unlikely, e.g. if one or both of the first and second pulses is made up of a combination of frequencies or frequency ranges.

Furthermore, the frequency, amplitude and phase content of the first pulse or the second pulse may vary over time. Such variations may be the result of an active control of the first and/or second pulse generator 3, 3', or be caused by drifts in the first and/or second pulse generator 3, 3' or by changes in the hydrodynamic properties of the sub-systems S1, S2 or the fluid connection C. Frequency variations may occur, e.g., when the second pulse generator 3' is a human heart, and the second sub-system S2 thus is the blood system of a human. In healthy subjects under calm conditions, variations in heart rhythm (heart rate variability, HRV) may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients.

Any frequency overlap may make it impossible or at least difficult to isolate the second pulses in the pressure signal by conventional filtering in the frequency domain, e.g. by operating a comb filter and/or a combination of band-stop or notch filters, typically cascade coupled, on the pressure signal to block out all frequency components originating from the first pulse generator 3. Furthermore, frequency variations make it even harder to successfully isolate second pulses in the pressure signal, since the frequency overlap may vary over time. Even in the absence of any frequency overlap, frequency variations make it difficult to define filters in the frequency domain.

Depending on how well the first pulse profile represents the first pulse(s) in the pressure signal, it may be possible to isolate the second pulses by means of the inventive filtering in the time-domain even if the first and second pulses overlap in frequency, and even if the second pulses are much smaller in amplitude than the first pulses.

Still further, the inventive filtering in the time domain may allow for a faster isolation of second pulses in the pressure signal than a filtering process in the frequency domain. The former may have the ability to isolate a single second pulse in the pressure signal whereas the latter may need to operate on a sequence of first and second pulses in the pressure signal. Thus, the inventive filtering may enable faster determination of the functional state or functional parameter of the fluid containing system.

Figure 14:
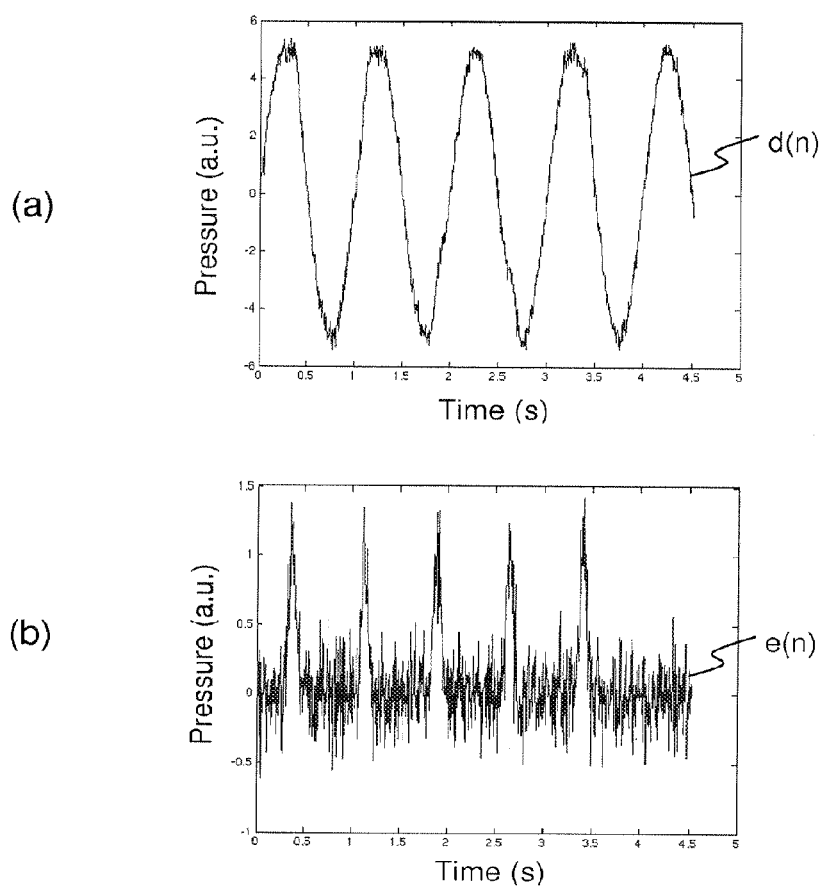
FIG. 14($a$) is a plot of a pressure signal as a function of time, and FIG. 14($b$) is a plot of the pressure signal after filtering.

The effectiveness of the inventive filtering is exemplified in FIG. 14, in which FIG. 14(a) shows an example of a time-dependent pressure signal d(n) containing first and second pulses with a relative magnitude of 10:1. The first and second pulses have a frequency of 1 Hz and 1.33 Hz, respectively. Due to the difference in magnitude, the pressure signal is dominated by the first pulses. FIG. 14(b) shows the time-dependent filtered signal e(n) that is obtained after applying the inventive filtering technique to the pressure signal d(n). The filtered signal e(n) is made up of second pulses and noise. It should be noted that there is an absence of second pulses after about 4 seconds, which may be observed by the surveillance device (25 in FIG. 12) and identified as a fault condition of the fluid containing system.

Figure 13:
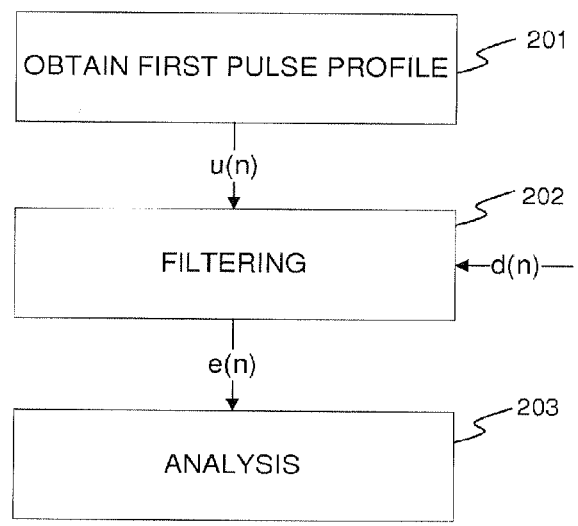
FIG. 13 is a flow chart of a monitoring process according to an embodiment of the invention.

Reverting to FIG. 13, the inventive data processing comprises two main steps: a determination of the first pulse profile u(n) (step 201) and a removal of one or more first pulses from a measurement signal d(n) using the first pulse profile u(n) (step 202).

There are many ways to implement these main steps. For example, the first pulse profile (standard signal profile) may be obtained in a reference measurement, based on a measurement signal from one or more of the pressure sensors 4a-4c in the first sub-system S1, suitably by identifying and possibly averaging a set of first pulse segments in the measurement signal(s). The first pulse profile may or may not be updated intermittently during the actual monitoring of the aforesaid functional state or parameter. Alternatively, a predetermined (i.e. predefined) standard signal profile may be used, which optionally may be modified according to a mathematical model accounting for wear in the first pulse generator, fluid flow rates, tubing dimensions, speed of sound in the fluid, etc. Further, the removal may involve subtracting the first pulse profile from the measurement signal at suitable amplitude and phase. The phase may be indicated by phase information which may be obtained from a signal generated by a phase sensor coupled to the first pulse generator 3, or from a control signal for the first pulse generator 3.

The inventive filtering may also be combined with other filtering techniques to further improve the quality of the filtered signal e(n). In one embodiment, the filtered signal e(n) could be passed through a bandpass filter with a passband in the relevant frequency range for the second pulses. If the second pulses originate from a human heart, the passband may be located within the approximate range of 0.5-4 Hz, corresponding to heart pulse rates of 30-240 beats per minute. In another embodiment, if the current frequency range (or ranges) of the second pulses is known, the passband of the bandpass filter could be actively controlled to a narrow range around the current frequency range. For example, such an active control may be applied whenever the rates of first and second pulses are found to differ by more than a certain limit, e.g. about 10%. The current frequency range may be obtained from the pressure signal, either by intermittently shutting off the first pulse generator 3, or intermittently preventing the first pulses from reaching the relevant pressure sensor 4a-4c. Alternatively, the current frequency range may be obtained from a dedicated sensor in either the first or the second sub-systems S1, S2, or based on a control unit (not shown) for the second pulse generator 3'. According to yet another alternative, the location and/or width of the passband could be set, at least in part, based on patient-specific information, i.e. existing data records for the patient, e.g. obtained in earlier treatments of the same patient. The patient-specific information may be stored in an internal memory of the surveillance device (25 in FIG. 12), on an external memory which is made accessible to the surveillance device, or on a patient card where the information is e.g. transmitted wirelessly to the surveillance device, e.g. by RFID (Radio Frequency IDentification).

These and other embodiments will be explained in further detail below, within the context of a system for extracorporeal blood treatment. To facilitate the following discussion, details of an exemplifying extracorporeal blood flow circuit will be first described.

Monitoring in an Extracorporeal Blood Flow Circuit

Figure 15:
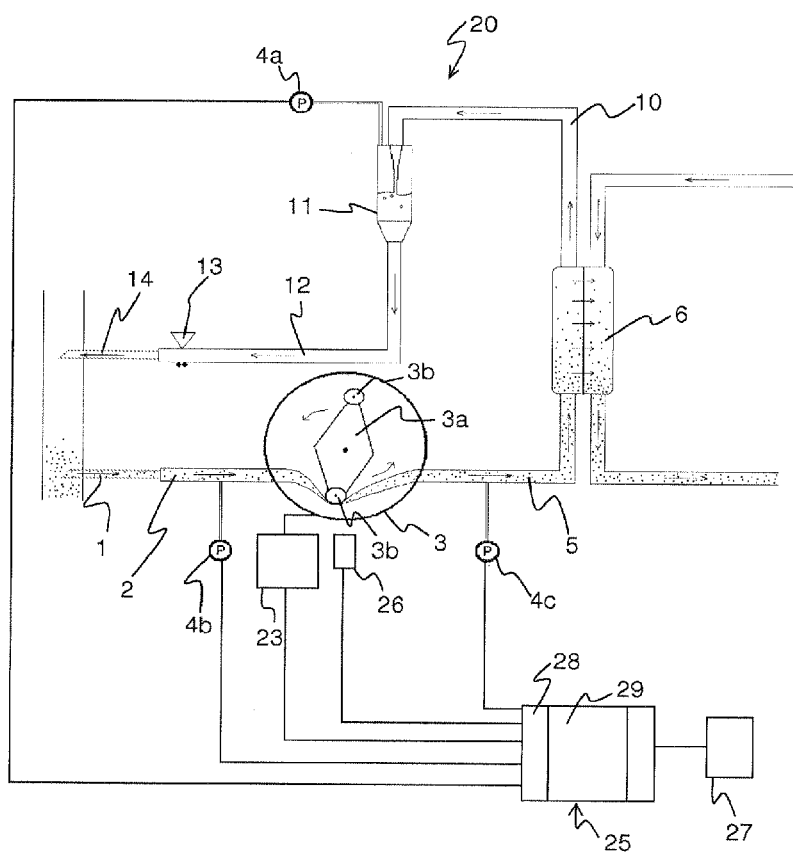
FIG. 15 is a schematic view of a system for hemodialysis treatment including an extracorporeal blood flow circuit.
Figure 16:
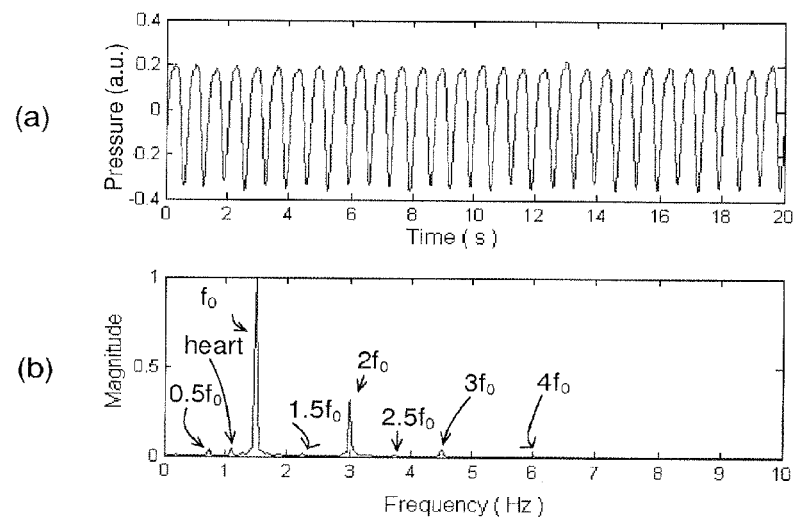
FIG. 16($a$) is a plot in the time domain of a venous pressure signal containing both pump frequency components and a heart signal, and FIG. 16($b$) is a plot of the corresponding signal in the frequency domain.

FIG. 15 shows an example of an extracorporeal blood flow circuit 20 of the type which is used for dialysis. The extracorporeal blood flow circuit 20 (also denoted "extracorporeal circuit") comprises components 1-14 to be described in the following. Thus, the extracorporeal circuit 20 comprises an access device for blood extraction in the form of an arterial needle 1, and an arterial tube segment 2 which connects the arterial needle 1 to a blood pump 3 which may be of peristaltic type, as indicated in FIG. 15. At the inlet of the pump there is a pressure sensor 4b (hereafter referred to as "arterial sensor") which measures the pressure before the pump in the arterial tube segment 2. The blood pump 3 forces the blood, via a tube segment 5, to the blood-side of a dialyser 6. Many dialysis machines are additionally provided with a pressure sensor 4c (hereafter referred to as "system sensor") that measures the pressure between the blood pump 3 and the dialyser 6. The blood is lead via a tube segment 10 from the blood-side of the dialyser 6 to a venous drip chamber or deaeration chamber 11 and from there back to the patient via a venous tube segment 12 and an access device for blood reintroduction in the form of a venous needle 14. A pressure sensor 4a (hereafter referred to as "venous sensor") is provided to measure the pressure on the venous side of the dialyser 6. In the illustrated example, the pressure sensor 4a measures the pressure in the venous drip chamber. Both the arterial needle 1 and the venous needle 14 are connected to the patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters. The access devices 1, 14 may alternatively be combined into a single unit.

In relation to the fluid containing system in FIG. 12, the extracorporeal circuit 20 corresponds to the first sub-system S1, the blood pump 3 (as well as any further pulse source(s) within or associated with the extracorporeal circuit 20, such as a dialysis solution pump, valves, etc) corresponds to the first pulse generator 3, the blood system of the patient corresponds to the second sub-system S2, and the fluid connection C corresponds to at least one of the venous-side and arterial-side fluid connections between the patient and the extracorporeal circuit 20.

In FIG. 15, a control unit 23 is provided, i.a., to control the blood flow in the extracorporeal circuit 20 by controlling the revolution speed of the blood pump 3. The extracorporeal circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

The system in FIG. 15 also includes a surveillance/monitoring device 25, which is connected to receive a pressure signal from at least one of the pressure sensors 4a-4c and which executes the inventive data processing. In the example of FIG. 15, the surveillance device 25 is also connected to the control unit 23. Alternatively or additionally, the device 25 may be connected to a pump sensor 26 for indicating the revolution speed and/or phase of the blood pump 3. It is to be understood that the surveillance device 25 may include inputs for further data, e.g. any other system parameters that represent the overall system state (see e.g. discussion with reference to FIG. 18 below). The device 25 is tethered or wirelessly connected to a local or remote device 27 for generating an audible/visual/tactile alarm or warning signal. Alternatively or additionally, either device 25, 27 may include a display or monitor for displaying the functional state or parameter resulting from the analysis step (203 in FIG. 13), and/or the filtered signal e(n) resulting from the filtering step (202 in FIG. 13), e.g. for visual inspection.

In FIG. 15, the surveillance device 25 comprises a data acquisition part 28 for pre-processing the incoming signal(s), e.g. including an A/D converter with a required minimum sampling rate and resolution, one or more signal amplifiers, and one or more filters to remove undesired components of the incoming signal(s), such as offset, high frequency noise and supply voltage disturbances.

After the pre-processing in the data acquisition part 28, the pre-processed pressure signal is provided as input to a main data processing part 29, which executes the inventive data processing. FIG. 16(a) shows an example of such a pre-processed pressure signal in the time domain, and FIG. 16(b) shows the corresponding power spectrum, i.e. the pre-processed pressure signal in the frequency domain. The power spectrum reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics 2 $f_0$, 3 $f_0$ and 4 $f_0$. The base frequency, also denoted pump frequency in the following, is the frequency of the pump strokes that generate pressure waves in the extracorporeal circuit 20. For example, in a peristaltic pump of the type shown in FIG. 15, two pump strokes are generated for each full revolution of the rotor 3a. FIG. 16(b) also indicates the presence of a frequency component at half the pump frequency (0.5 $f_0$) and harmonics thereof, in this example at least $f_0$, 1.5 $f_0$, 2 $f_0$ and 2.5 $f_0$. FIG. 16(b) also shows a heart signal (at 1.1 Hz) which in this example is approximately 40 times weaker than the blood pump signal at the base frequency $f_0$.

The main data processing part 29 executes the aforesaid steps 201-203. In step 202, the main data processing part 29 operates to filter the pre-processed pressure signal in the time domain, and outputs a filtered signal or monitoring signal (e(n) in FIG. 13) in which the signal components of the blood pump 3 have been removed. The monitoring signal still contains any signal components that originate from the patient (cf. FIG. 14(b)), such as pressure pulses caused by the beating of the patient's heart. There are a number of sources to cyclic physiological phenomena that may generate pressure pulses in the blood stream of the patient, including the heart, the breathing system, or the vasomotor, which is controlled by the autonomic nervous system. Thus, the monitoring signal may contain pressure pulses resulting from a combination of cyclic phenomena in the patient. Generally speaking, the signal components in the monitoring signal may originate from any type of physiological phenomenon in the patient, or combinations thereof, be it cyclic or non-cyclic, repetitive or non-repetitive, autonomous or non-autonomous.

Depending on implementation, the surveillance device 25 may be configured apply further filtering to the monitoring signal to isolate signal components originating from a single cyclic phenomenon in the patient. Alternatively, such signal component filtering is done during the pre-processing of the pressure signal (by the data acquisition part 28). The signal component filtering may be done in the frequency domain, e.g. by applying a cut-off or bandpass filter, since the signal components of the different cyclic phenomena in the patient are typically separated in the frequency domain. Generally, the heart frequency is about 0.5-4 Hz, the breathing frequency is about 0.15-0.4 Hz, the frequency of the autonomous system for regulation of blood pressure is about 0.04-0.14 Hz, the frequency of the autonomous system for regulation of body temperature is about 0.04 Hz.

The surveillance device 25 could be configured to monitor the breathing pattern of the patient, by identifying breathing pulses in the monitoring signal. The resulting information could be used for on-line surveillance for apnoea, hyperventilation, hypoventilation, asthmatic attacks or other irregular breathing behaviours of the patient. The resulting information could also be used to identify coughing, sneezing, vomiting or seizures. The vibrations resulting from coughing/sneezing/vomiting/seizures might disturb other measurement or surveillance equipment that is connected to the patient or the extracorporeal circuit 20. The surveillance device 25 may be arranged to output information about the timing of any coughing/sneezing/vomiting/seizures, such that other measurement or surveillance equipment can take adequate measures to reduce the likelihood that the coughing/sneezing/vomiting/seizures results in erroneous measurements or false alarms. Of course, the ability of identifying coughing/sneezing/vomiting/seizures may also have a medical interest of its own.

The surveillance device 25 could be configured to monitor the heart rate of the patient, by identifying heart pulses in the monitoring signal.

The surveillance device 25 could be configured to collect and store data on the time evolution of the heart rate, the breathing pattern, etc, e.g. for subsequent trending or statistical analysis.

The surveillance device 25 may be configured to monitor the integrity of the fluid connection between the patient and the extracorporeal circuit 20, in particular the venous-side fluid connection (via access device 14). This could be done by monitoring the presence of a signal component originating from, e.g., the patient's heart or breathing system in the monitoring signal. Absence of such a signal component may be taken as an indication of a failure in the integrity of the fluid connection C, and could bring the device 25 to activate an alarm and/or stop the blood flow, e.g. by stopping the blood pump 3 and activating a clamping device 13 on the tube segment 12. For monitoring the integrity of the venous-side fluid connection, also known as VNM (Venous Needle Monitoring), the surveillance device 25 may be configured to generate the monitoring signal based on a pressure signal from the venous sensor 4a. The device 25 may also be connected to pressure sensors 4b, 4c, as well as any additional pressure sensors included in the extracorporeal circuit 20.

The extracorporeal circuit 20 may have the option to operate in a hemodiafiltration mode (HDF mode), in which the control unit 23 activates a second pumping device (HDF pump, not shown) to supply an infusion solution into the blood line upstream and/or downstream of the dialyser 6, e.g. into one or more of tube segments 2, 5, 10 or 12.

Obtaining the Predicted Signal Profile of First Pulses

This section describes different embodiments for predicting or estimating the signal profile of first pulses in the system shown in FIG. 15. The predicted signal profile is typically given as a series of pressure values over a period of time normally corresponding to at least one complete pump cycle of the blood pump 3.

Figure 17:
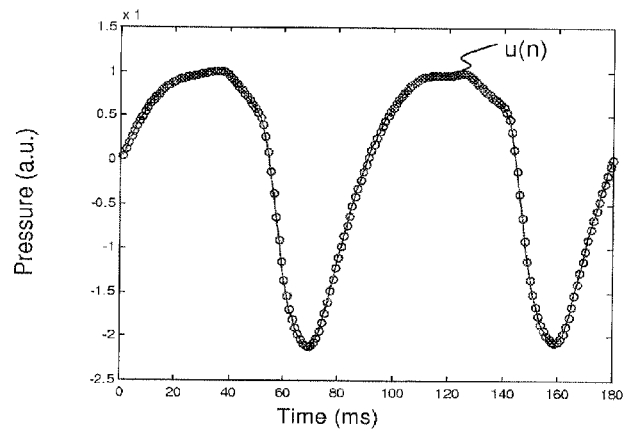
FIG. 17 is a plot of a predicted signal profile originating from a peristaltic pump in the system of FIG. 15.

FIG. 17 illustrates an example of a predicted signal profile for the system in FIG. 15. Since the blood pump 3 is a peristaltic pump, in which two rollers 3b engage a tube segment during a full revolution of the rotor 3a, the pressure profile consists of two pump strokes. The pump strokes may result in different pressure values (pressure profiles), e.g. due to slight differences in the engagement between the rollers 3b and the tube segment, and thus it may be desirable for the predicted signal profile to represent both pump strokes. If a lower accuracy of the predicted signal profile can be tolerated, i.e. if the output of the subsequent removal process is acceptable, the predicted signal profile might represent one pump stroke only.

On a general level, the predicted signal profile may be obtained in a reference measurement, through mathematical simulation of the fluid system, or combinations thereof.

Reference Measurement

A first main group of methods for obtaining the predicted signal profile is based on deriving a time-dependent reference pressure signal ("reference signal") from a pressure sensor in the system, typically (but not necessarily) from the same pressure sensor that provides the measurement signal (pressure signal) that is to be processed for removal of first pulses. During this reference measurement, the second pulses are prevented from reaching the relevant pressure sensor, either by shutting down/deactivating the second pulse generator 3' or by isolating the pressure sensor from the second pulses. In the system of FIG. 15, the reference measurement could be carried out during a priming phase, in which the extracorporeal circuit 20 is detached from the patient and a priming fluid is pumped through the blood lines. Alternatively, the reference measurement could be carried in a simulated treatment with blood or any other fluid. Optionally, the reference measurement could involve averaging a plurality of pressure profiles to reduce noise. For example, a plurality of relevant signal segments may be identified in the reference signal, whereupon these segments are aligned to achieve a proper overlap of the pressure profiles in the different segments and then added together. The identifying of relevant signal segments may be at least partially based on timing information which indicates the expected position of each first pulse in the reference signal. The timing information may be obtained from a trigger point in the output signal of the pump sensor 26, in a control signal of the control unit 23, or in the pressure signal from another one of the pressure sensors 4a-4c. For example, a predicted time point of a first pulse in the reference signal can be calculated based on a known difference in arrival time between the trigger point and the pressure sensor that generates the reference signal. In variant, if the reference signal is periodic, relevant signal segments may be identified by identifying crossing points of the reference signal with a given signal level, wherein the relevant signal segments are identified to extend between any respective pairs of crossing points.

In a first embodiment, the predicted signal profile is directly obtained in a reference measurement before the extracorporeal circuit 20 is connected to the patient, and is then used as input to the subsequent removal process, which is executed when the extracorporeal circuit 20 is connected to the patient. In this embodiment, it is thus assumed that the predicted signal profile is representative of the first pulses when the system is connected to the patient. Suitably, the same pump frequency/speed is used during the reference measurement and during the removal process. It is also desirable that other relevant system parameters are maintained essentially constant.

Figure 18:
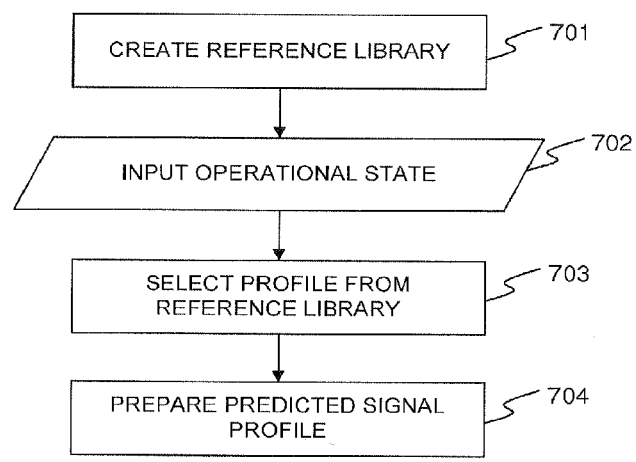
FIG. 18 is a flow chart of a process for obtaining the predicted signal profile.

FIG. 18 is a flow chart of a second embodiment. In the second embodiment, a reference library or database is first created based on the reference measurement (step 701). The resulting reference library is typically stored in a memory unit, e.g. RAM, ROM, EPROM, HDD, Flash, etc (cf. 25b in FIG. 12) of the surveillance device (cf. 25 in FIG. 12). During the reference measurement, reference pressure signals are acquired for a number of different operational states of the extracorporeal circuit. Each operational state is represented by a unique combination of system parameter values. For each operational state, a reference profile is generated to represent the signal profile of the first pulses. The reference profiles together with associated system parameter values are then stored in the reference library, which is implemented as a searchable data structure, such as a list, look-up table, search tree, etc.

During the actual monitoring process, i.e. when first pulses are to be eliminated from the measurement signal, current state information indicating the current operational state of the fluid containing system is obtained from the system, e.g. from a sensor, a control unit or otherwise (step 702). The current state information may include a current value of one or more system parameters. The current value is then matched against the system parameter values in the reference library. Based on the matching, one or more reference profiles are selected (step 703) and used for preparing the predicted signal profile (step 704).

Generally, the aforesaid system parameters represent the overall system state, including but not limited to the structure, settings, status and variables of the fluid containing system or its components. In the system of FIG. 15, exemplary system parameters may include:

Pump-related parameters: number of active pumps connected directly or indirectly (e.g. in a fluid preparation system for the dialyser) to the extracorporeal circuit, type of pumps used (roller pump, membrane pump, etc), flow rate, revolution speed of pumps, shaft position of pump actuator (e.g. angular or linear position), etc.

Dialysis machine setting temperature, ultrafiltration rate, mode changes, valve position/changes, etc.

Disposable dialysis equipment/material: information on pump chamber/pump segment (material, geometry and wear status), type of blood line (material and geometry), type of dialyser, type and geometry of access devices, etc.

Dialysis system variables: actual absolute pressures of the system upstream and downstream of the blood pump, e.g. venous pressure (from sensor 4a), arterial pressure (from sensor 4b) and system pressure (from sensor 4c), gas volumes trapped in the flow path, blood line suspension, fluid type (e.g. blood or dialysis fluid), etc.

Patient status: blood access properties, blood properties such as e.g. hematocrit, plasma protein concentration, etc.

It is to be understood that any number or combination of system parameters may be stored in the reference library and/or used as search variables in the reference library during the monitoring process.

In the following, the second embodiment will be further explained in relation to a number of examples. In all of these examples, the pump revolution frequency ("pump frequency"), or a related parameter (e.g. blood flow rate) is used to indicate the current operational state of the fluid containing system during the monitoring process. In other words, the pump frequency is used as search variable in the reference library. The pump frequency may e.g. be given by a set value for the blood flow rate output from the control unit, or by an output signal of a sensor that indicates the frequency of the pump (cf. pump sensor 26 in FIG. 15). Alternatively, the pump frequency could be obtained by frequency analysis of the pressure signal from any of the sensors 4a-4c during operation of the fluid system. Such frequency analysis could be achieved by applying any form of harmonics analysis to the pressure signal, such as Fourier or wavelet analysis. As indicated in FIG. 16(b), the base frequency $f_0$ of the pump can be identified in a resulting power spectrum.

Figure 19:
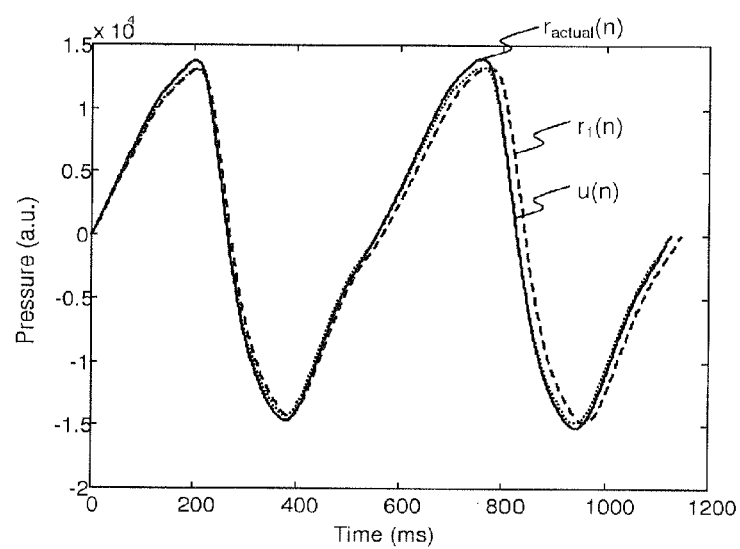
FIG. 19 is a plot to illustrate an extrapolation process for generating the predicted signal profile.

In a first example, the reference library is searched for retrieval of the reference profile that is associated with the pump frequency that lies closest to the current pump frequency. If no exact match is found to the current pump frequency, an extrapolation process is executed to generate the predicted signal profile. In the extrapolation process, the retrieved reference profile is scaled in time to the current pump cycle, based on the known difference ("pump frequency difference") between the current pump frequency and the pump frequency associated with the retrieved reference profile. The amplitude scale may also be adjusted to compensate for amplitude changes due to pump frequency, e.g. based on a known function of amplitude as a function of pump frequency. FIG. 19 illustrates a reference profile $r_1(n)$ obtained at a flow rate of 470 ml/min, and predicted signal profile u(n) which is obtained by scaling the reference profile to a flow rate of 480 ml/min. For comparison only, a reference profile $r_{actual}(n)$ obtained at 480 ml/min is also shown, to illustrate that extrapolation process indeed may yield a properly predicted signal profile.

In a second example, the reference library is again searched based on current pump frequency. If no exact match is found to the current pump frequency, a combination process is executed to generate the predicted signal profile. Here, the reference profiles associated with the two closest matching pump frequencies are retrieved and combined. The combination may be done by re-scaling the pump cycle time of the retrieved reference profiles to the current pump frequency and by calculating the predicted signal profile via interpolation of the re-scaled reference profiles. For example, the predicted signal profile u(n) at the current pump frequency v may be given by:

$$u(n)=g(v-v_i)\cdot r_i(n)+(1-g(v-v_i))\cdot r_j(n),$$

wherein $r_i(n)$ and $r_j(n)$ denotes the two retrieved reference profiles, obtained at a pump frequency $v_i$ and $v_j$, respectively, after re-scaling to the current pump frequency v, and g is a relaxation parameter which is given as a function of the frequency difference $(v-v_i)$, wherein $v_i \leq v \leq v_j$ and $0 \leq g \leq 1$. The skilled person realizes that the predicted signal profile u(n) may be generated by combining more than two reference profiles.

Figure 20A:
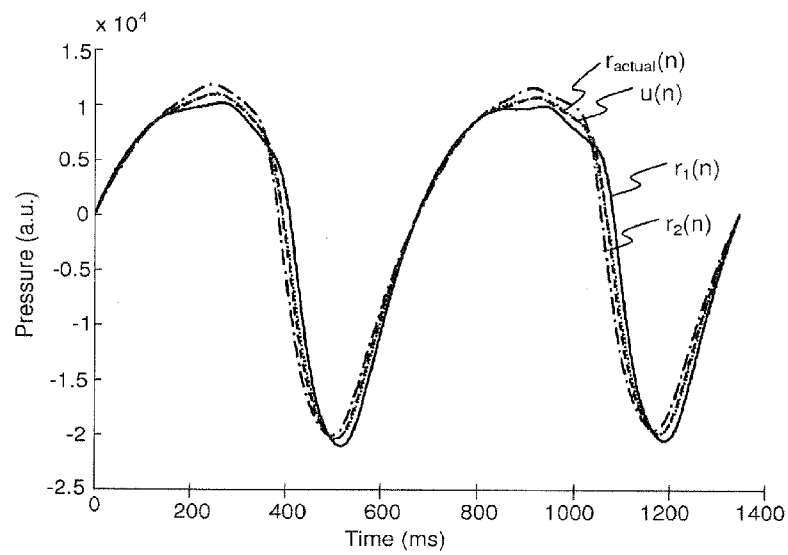
FIG. 20($a$) is a plot to illustrate an interpolation process for generating the predicted signal profile, and FIG. 20($b$) is an enlarged view of FIG. 20($a$).
Figure 20B:
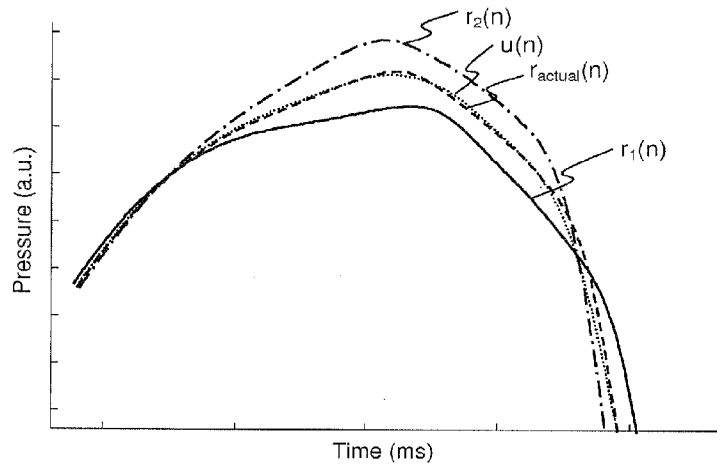

FIG. 20(a) illustrates a predicted signal profile u(n) at a current flow rate of 320 ml/min for a measurement signal obtained from the venous sensor 4a in the system of FIG. 15. The predicted signal profile u(n) has been calculated as an average of a reference profile $r_1(n)$ obtained at a flow rate of 300 ml/min from the venous sensor and a reference profile $r_2(n)$ obtained at a flow rate of 340 ml/min from the venous sensor. For comparison only, a reference profile $r_{actual}(n)$ obtained at 320 ml/min is also shown, to illustrate that the combination process indeed may yield a properly predicted signal profile. In fact, the differences are so small that they are only barely visible in the enlarged view of FIG. 20(b).

The first and second examples may be combined, e.g. by executing the extrapolation process of the first example if the pump frequency difference is less than a certain limit, and otherwise executing the combination process of the second example.

In a third embodiment, like in the second embodiment shown in FIG. 18, a number of reference signals are acquired in the reference measurement, wherein each reference signal is obtained for a specific combination of system parameter values. The reference signals are then processed for generation of reference spectra, which are indicative of the energy and phase angle as function of frequency. These reference spectra may e.g. be obtained by Fourier analysis, or equivalent, of the reference signals. Corresponding energy and phase data are then stored in a reference library together with the associated system parameter values (cf. step 701 in FIG. 18). The implementation of the reference library may be the same as in the second embodiment.

During the actual monitoring process, i.e. when first pulses are to be eliminated from the measurement signal, a current value of one or more system parameters is obtained from the fluid containing system (cf. step 702 in FIG. 18). The current value is then matched against the system parameter values in the reference library. Based on the matching, a specific set of energy and phase data may be retrieved from the reference library to be used for generating the predicted signal profile (cf. step 703 in FIG. 18). Generally, the predicted signal profile is generated by adding sinusoids of appropriate frequency, amplitude and phase, according to the retrieved energy and phase data (cf. step 704 in FIG. 18).

Generally speaking, without limiting the present disclosure, it may be advantageous to generate the predicted signal profile from energy and phase data when the first pulses (to be removed) contain only one or a few base frequencies (and harmonics thereof), since the predicted signal profile can be represented by a small data set (containing energy and phase data for the base frequencies and the harmonics). One the other hand, when the power spectrum of the first pulses is more complex, e.g. a mixture of many base frequencies, it may instead be preferable to generate the predicted signal profile from one or more reference profiles.

Figure 21A:
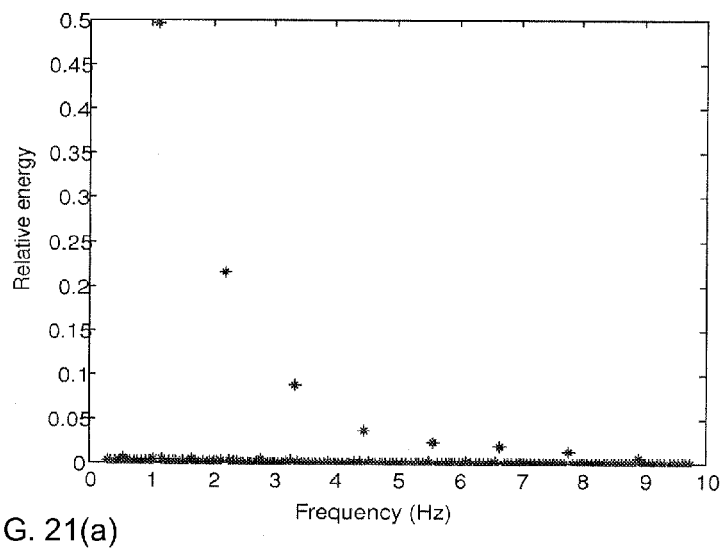
FIG. 21($a$) represents a frequency spectrum of a pressure pulse originating from a pumping device at one flow rate, FIG. 21($b$) represents corresponding frequency spectra for three different flow rates, wherein each frequency spectrum is given in logarithmic scale and mapped to harmonic numbers, FIG. 21($c$) is a plot of the data in FIG. 21($b$) in linear scale, and FIG. 21($d$) is a phase angle spectrum corresponding to the frequency spectrum in FIG. 21($a$).
Figure 21B:
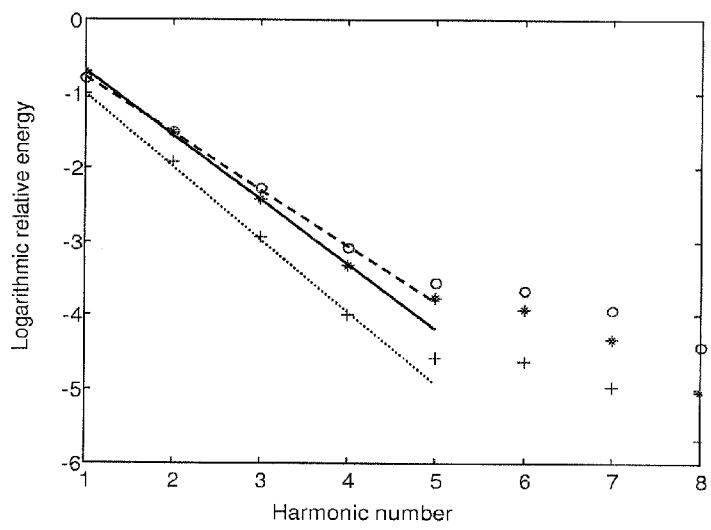

FIG. 21(a) represents an energy spectrum of a reference signal acquired at a flow rate of 300 ml/min in the system of FIG. 15. In this example, the reference signal essentially consists of a basic pump frequency at 1.2 Hz ($f_0$, first harmonic) and a set of overtones of this frequency (second and further harmonics). Compared to the power spectrum of FIG. 16(b), the pressure signals used for generating the graphs in FIG. 21(a)-21(d) do not contain any significant frequency component at 0.5 $f_0$ and its harmonics. The graph in FIG. 21(a) displays the relative energy distribution, wherein the energy values have been normalized to the total energy for frequencies in the range of 0-10 Hz. FIG. 21(b) represents energy spectra of reference signals acquired at three different flow rates in the system of FIG. 15. The energy spectra are given in logarithmic scale versus harmonic number (first, second, etc). As shown, an approximate linear relationship can be identified between the logarithmic energy and harmonic number for the first four to five harmonic numbers. This indicates that each energy spectrum may be represented by a respective exponential function.

Figure 21C:
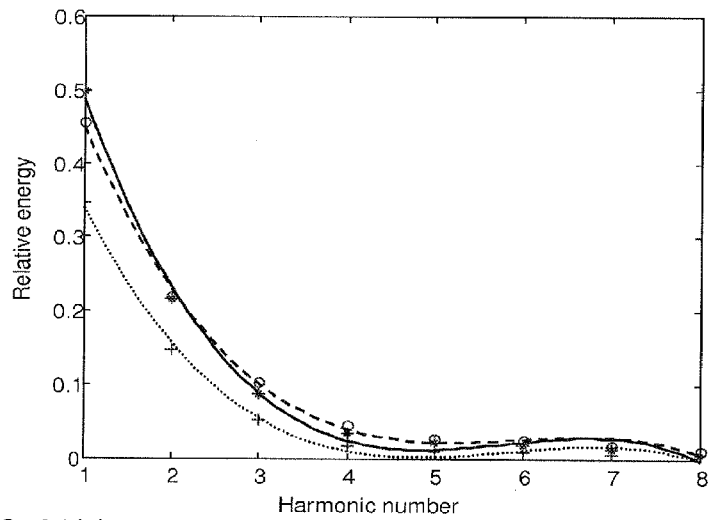

FIG. 21(c) illustrates the data of FIG. 21(b) in linear scale, wherein a respective polynomial function has been fitted to the data. As indicated in FIGS. 21(a)-21(c), the energy spectra may be represented in different formats in the reference library, e.g. as a set of energy values associated with discrete frequency values or harmonic numbers, or as an energy function representing energy versus frequency/harmonic number.

Figure 21D:
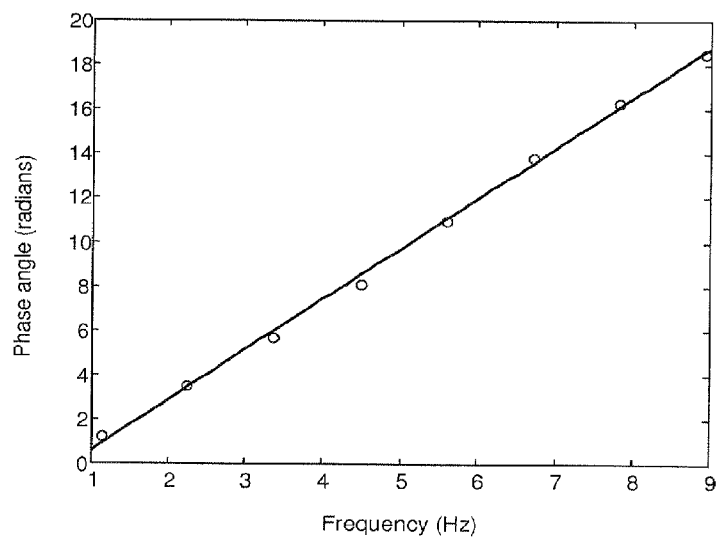

FIG. 21(d) illustrates a phase angle spectrum acquired together with the energy spectrum in FIG. 21(a), i.e. for a flow rate of 300 ml/min. The graph in FIG. 21(d) illustrates phase angle as a function of frequency, and a linear function has been fitted to the data. In an alternative representation (not shown), the phase spectrum may be given as a function of harmonic number. Like the energy spectra, the phase spectra may be represented in different formats in the reference library, e.g. as a set of phase angle values associated with discrete frequency values or harmonic numbers, or as a phase function representing phase angle versus frequency/harmonic number.

From the above, it should be understood that the energy and phase data that are stored the reference library can be used to generate the predicted signal profile. Each energy value in the energy data corresponds to an amplitude of a sinusoid with a given frequency (the frequency associated with the energy value), wherein the phase value for the given frequency indicates the proper phase angle of the sinousoid. This method of preparing the predicted signal profile by combining (typically adding) sinusoids of appropriate frequency, amplitude and phase angle allows the predicted signal profile to include all harmonics of the pump frequency within a desired frequency range.

When a predicted signal profile is to be generated, the reference library is first searched based on a current value of one or more system parameters, such as the current pump frequency. If no exact match is found in the reference library, a combination process may be executed to generate the predicted signal profile. For example, the two closest matching pump frequencies may be identified in the reference library and the associated energy and phase data may be retrieved and combined to form the predicted signal profile. The combination may be done by interpolating the energy data and the phase data. In the example of FIGS. 21(a)-21(d), an interpolated energy value may be calculated for each harmonic number, and similarly an interpolated phase value could be calculated for each harmonic number. Any type of interpolation function could be used, be it linear or non-linear.

In the first, second and third embodiments, the reference signals and the measurement signals are suitably obtained from the same pressure sensor unit in the fluid containing system. Alternatively, different pressure sensor units could be used, provided that the pressure sensor units yield identical signal responses with respect to the first pulses or that the signal responses can be matched using a known mathematical relationship.

To further improve the first, second and third embodiments, the process of generating the predicted signal profile may also involve compensating for other potentially relevant factors that differ between the reference measurement and the current operational state. These so-called confounding factors may comprise one or more of the system parameters listed above, such as absolute average venous and arterial pressures, temperature, blood hematocrit/viscosity, gas volumes, etc. This compensation may be done with the use of predefined compensation formulas or look-up tables.

In further variations, the second and third embodiments may be combined, e.g. in that the reference library stores not only energy and phase data, but also reference profiles, in association with system parameter value(s). When an exact match is found in the library, the reference profile is retrieved from the library and used as the predicted signal profile, otherwise the predicted signal profile is obtained by retrieving and combining (e.g. interpolating) the energy and phase data, as in the third embodiment. In a variant, the predicted signal profile u(n) at the current pump frequency v is obtained by:

$$u(n) = r_i(n) - r^f_i(n) + r^f(n),$$

wherein $r_i(n)$ denotes a reference profile that is associated with the closest matching pump frequency $v_i$ in the reference library, $r^f_i(n)$ denotes a reference profile that is reconstructed from the energy and phase data associated with the closest matching pump frequency $v_i$ in the reference library, and $r^f(n)$ denotes an estimated reference profile at the current pump frequency v. The estimated reference profile $r^f(n)$ may be obtained by applying predetermined functions to estimate the energy and phase data, respectively, at the current pump frequency v based on the energy and phase data associated with the closest matching pump frequency $v_i$. With reference to FIGS. 21(b)-21(c), such a predetermined function may thus represent the change in energy data between different flow rates. Alternatively, the estimated reference profile $r^f(n)$ may be obtained by retrieving and combining (e.g. interpolating) energy and phase data for the two closest matching pump frequencies $v_i$ and $v_j$ as in the third embodiment.

In a further variant, the reference measurement is made during regular operation of the fluid containing system, instead of or in addition to any reference measurements made before regular operation (e.g. during priming or simulated treatments with blood). Such a variant presumes that it is possible to intermittently shut off the second pulse generator, or to intermittently prevent the second pulses from reaching the relevant pressure sensor. This approach is more difficult in the extracorporeal circuit 20 of FIG. 15 if the reference signals and the measurement signals are obtained from the one and the same pressure sensor. However, this approach can e.g. be applied if the fluid system includes one pressure sensor that is substantially isolated from the second pulses. In such a situation, the reference profile (or reference spectra) may be obtained from the isolated sensor, and used for generating the predicted signal profile (optionally after adjustment/modification for differences in confounding factors), which is then used for removing first pulses from a measurement signal that contains both first and second pulses. For example, the pressure signal from the system sensor 4c in the circuit 20 of FIG. 15 may be essentially isolated from the second pulses that originate from the patient, and this pressure signal may thus be used in a reference measurement.

As explained above, the extracorporeal circuit 20 in FIG. 15 may be switched into a HDF mode, in which an additional HDF pump is activated to supply an infusion liquid into the blood line of the extracorporeal circuit 20. Such a change of operating mode may cause a change in the signal characteristics of the first pulses in the measurement signal. Thus, it may be necessary to account for this change, by ensuring that the reference library includes appropriate reference data (reference profiles and/or energy and phase angle data) associated with this operational state.

Alternatively, it may be desirable to isolate the pressure pulses originating from the HDF pump. This could be achieved by obtaining a reference profile from the pressure signal of the arterial sensor 4b (FIG. 15). The arterial pressure signal includes pressure pulses originating from the patient and from the blood pump 3, whereas pressure pulses originating from the HDF pump are significantly damped by the patient and the blood pump 3, respectively, and thus barely reach the arterial sensor 4b. On the other hand, the pressure signals of the venous sensor 4a and the system sensor 4c contain pressure pulses originating from both the patient, the blood pump 3 and the HDF pump. Thus, the arterial pressure signal may be used for obtaining the predicted signal profile of the combined pressure pulses originating from the blood pump 3 and the patient as they should look in the pressure signal from the venous sensor 4a or the system sensor 4c. The predicted signal profile may then be used for isolating the pressure pulses originating from the HDF pump in the pressure signal from the venous sensor 4a or the system sensor 4c. In this example, the patient and the extracorporeal circuit 20 could be regarded as a first sub-system (S1 in FIG. 12) and the HDF pump and the associated infusion tubing could be regarded as a second sub-system (S2 in FIG. 12), which are connected via a fluid connection. Thus, in this example, the inventive data processing is not applied to isolate pulses originating from a cyclic physiological phenomenon in the patient, but pulses originating from another pump in the fluid system. It should be realized that in other arrangements, the reference profile may be obtained from the pressure signal of the venous sensor 4a (FIG. 15), and used for processing the pressure signal of the arterial sensor 4b or system sensor 4c.

Simulations

As an alternative to the use of reference measurements, the predicted signal profile may be obtained directly through simulations, i.e. calculations using a mathematical model of the fluid containing system, based on current state information indicating the current operational state of the system. Such current state information may include a current value of one or more of the above-mentioned system parameters. The model may be based on known physical relationships of the system components (or via an equivalent representation, e.g. by representing the system as an electrical circuit with fluid flow and pressure being given by electrical current and voltage, respectively). The model may be expressed, implicitly or explicitly, in analytical terms. Alternatively, a numerical model may be used. The model could be anything from a complete physical description of the system to a simple function. In one example, such a simple function could convert data on the instantaneous angular velocity of the pump rotor 3a to a predicted signal profile, using empirical or theoretical data. Such data on the instantaneous angular velocity might be obtained from the pump sensor 26 in FIG. 15.

In another embodiment, simulations are used to generate reference profiles for different operational states of the system. These reference profiles may then be stored in a reference library, which may be accessed and used in the same way as described above for the second and third embodiments. It is also to be understood that reference profiles (and/or corresponding energy and phase angle data) obtained by simulations may be stored together with reference profiles (and/or corresponding energy and phase angle data) obtained by reference measurement.

Removal of First Pulses

There are several different ways of removing one or more first pulses from the measurement signal, using the predicted signal profile. Here, two different removal processes will be described: Single Subtraction and Adaptive Filtering. Of course, the description of removal processes and their implementations is not comprehensive (neither of the different alternatives nor of the implementations), which is obvious to a person skilled in the art.

Depending on implementation, the predicted signal profile may be input to the removal process as is, or the predicted signal profile may be duplicated to construct an input signal of suitable length for the removal process.

Single Subtraction

In this removal process, a single predicted signal profile is subtracted from the measurement signal. The predicted signal profile may be shifted and scaled in time and scaled in amplitude in any way, e.g. to minimize the error of the removal. Different minimization criterions may be used for such an auto-scaling, e.g., minimizing the sum of the squared errors, or the sum of the absolute errors. Alternatively or additionally, the predicted signal profile is shifted in time based on timing information that indicates the expected timing of the first pulse(s) in the measurement signal. The timing information may be obtained in the same way as described above in relation to the averaging of pressure segments in the reference signal.

One potential limitation of this removal process is that the relationship between different frequencies in the predicted signal profile is always the same, since the process only shifts and scales the predicted signal profile. Thus, it is not possible to change the relationship between different harmonic frequencies, neither is it possible to use only some of the frequency content in the predicted signal profile and to suppress other frequencies. To overcome this limitation, adaptive filtering may be used since it uses a linear filter before subtraction, e.g. as described in the following.

Adaptive Filtering

Figure 22:
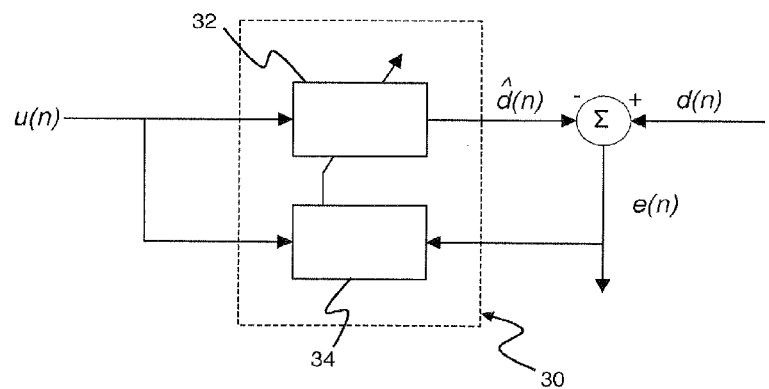
FIG. 22 is schematic view of an adaptive filter structure operable to filter a measurement signal based on a predicted signal profile.

FIG. 22 is a schematic overview of an adaptive filter 30 and an adaptive filter structure which is designed to receive the predicted signal profile u(n) and a measurement signal d(n), and to output an error signal e(n) which forms the aforesaid monitoring signal in which the first pulses are removed.

Adaptive filters are well-known electronic filters (digital or analog) that self-adjust their transfer function according to an optimizing algorithm. Specifically, the adaptive filter 30 includes a variable filter 32, typically a finite impulse response (FIR) filter of length M with filter coefficients w(n).

Even if adaptive filters are known in the art, they are not readily applicable to cancel the first pulses in the measurement signal d(n). In the illustrated embodiment, this has been achieved by inputting the predicted signal profile u(n) to the variable filter 32, which processes the predicted signal profile u(n) to generate an estimated measurement signal $\hat{d}(n)$, and to an adaptive update algorithm 34, which calculates the filter coefficients of the variable filter 32 based on the predicted signal profile u(n) and the error signal e(n). The error signal e(n) is given by the difference between the measurement signal d(n) and the estimated measurement signal $\hat{d}(n)$.

Basically, the adaptive filtering also involves a subtraction of the predicted signal profile u(n) from the measurement signal d(n), since each of the filter coefficients operates to shift and possibly re-scale the amplitude of the predicted signal profile u(n). The estimated measurement signal $\hat{d}(n)$, which is subtracted from the measurement signal d(n) to generate the error signal e(n), is thus formed as a linear combination of M shifted predicted signal profiles u(n), i.e. a linear filtering of u(n).

The adaptive update algorithm 34 may be implemented in many different ways, some of which will be described below. The disclosure is in no way limited to these examples, and the skilled person should have no difficulty of finding further alternatives based on the following description.

There are two main approaches to adaptive filtering: stochastic and deterministic. The difference lies in the minimization of the error signal e(n) by the update algorithm 34, where different minimization criteria are obtained whether e(n) is assumed to be stochastic or deterministic. A stochastic approach typically uses a cost function J with an expectation in the minimization criterion, while a deterministic approach typically uses a mean. The squared error signal $e^2(n)$ is typically used in a cost function when minimizing e(n), since this results in one global minimum. In some situations, the absolute error |e(n)| may be used in the minimization, as well as different forms of constrained minimizations. Of course, any form of the error signal may be used, however convergence towards a global minimum is not always guaranteed and the minimization may not always be solvable.

In a stochastic description of the signal, the cost function may typically be according to, $$J(n)=E\{|e(n)|^2\},$$

and in a deterministic description of the signal the cost function may typically be according to, $$J(n)=\Sigma e^2(n).$$

The first pulses will be removed from the measurement signal d(n) when the error signal e(n) (cost function J(n)) is minimized. Thus, the error signal e(n) will be cleaned from first pulses while retaining the second pulses, once the adaptive filter 30 has converged and reached the minimum error.

In order to obtain the optimal filter coefficients w(n) for the variable filter 32, the cost function J needs to be minimized with respect to the filter coefficients w(n). This may be achieved with the cost function gradient vector ∇J, which is the derivative of J with respect to the different filter coefficients $w_0, w_1, \ldots, w_{M-1}$. Steepest Descent is a recursive method (not an adaptive filter) for obtaining the optimal filter coefficients that minimize the cost function J. The recursive method is started by giving the filter coefficients an initial value, which is often set to zero, i.e., w(0)=0. The filter coefficients is then updated according to, $$w(n+1) = w(n) + \frac{1}{2}\mu[-\nabla J(n)],$$

where w is given by, $$w=[w_0 w_1 \ldots w_{M-1}]^T M\times 1.$$

Furthermore, the gradient vector ∇J points in the direction in which the cost is growing the fastest. Thus, the filter coefficients are corrected in the direction opposite to the gradient, where the length of the correction is influenced through the step size parameter μ. There is always a risk for the Steepest Descent algorithm to diverge, since the algorithm contains a feedback. This sets boundaries on the step size parameter μ in order to ensure convergence. It may be shown that the stability criterion for the Steepest Descent algorithm is given by, $$0 < \mu < \frac{2}{\lambda_{max}}$$

where $\lambda_{max}$ is the largest eigenvalue of R, the correlation matrix of the predicted signal profile u(n), given by $$R = E[\bar{u}(n)\bar{u}^T(n)] = \begin{bmatrix} r(0) & r(1) & \cdots & r(M-1) \\ r(1) & r(0) & & r(M-2) \\ \vdots & \vdots & \ddots & \vdots \\ r(M-1) & r(M-2) & \cdots & r(0) \end{bmatrix},$$

where $\bar{\mu}(n)$ is given by, $$\mu(n)=[u(n)u(n-1)\ldots u(n-M+1)]^T M\times 1.$$

If the mean squared error (MSE) cost function (defined by $J=E\{|e(n)|^2\}$) is used, it may be shown that the filter coefficients are updated according to, $$w(n+1)=w(n)+\mu E[\bar{u}(n)e(n)],$$

where e(n) is given by, $$e(n)=d(n)-\bar{u}^T(n)w(n).$$

The Steepest Descent algorithm is a recursive algorithm for calculation of the optimal filter coefficients when the statistics of the signals are known. However, this information is often unknown. The Least Mean Squares (LMS) algorithm is a method that is based on the same principles as the Steepest Descent algorithm, but where the statistics is estimated continuously. Thus, the LMS algorithm is an adaptive filter, since the algorithm can adapt to changes in the signal statistics (due to continuous statistic estimations), although the gradient may become noisy. Because of the noise in the gradient, the LMS algorithm is unlikely to reach the minimum error $J_{min}$, which the Steepest Descent algorithm does. Instantaneous estimates of the expectation are used in the LMS algorithm, i.e., the expectation is removed. Thus, for the LMS algorithm, the update equation of the filter coefficients becomes $$w(n+1)=w(n)+\mu\bar{u}(n)e(n).$$

The convergence criterion of the LMS algorithm is the same as for the Steepest Descent algorithm. In the LMS algorithm, the step size is proportional to the predicted signal profile u(n), i.e., the gradient noise is amplified when the predicted signal profile is strong. One solution to this problem is to normalize the update of the filter coefficients with $$\|\bar{u}(n)\|^2 = \bar{u}^T(n)\bar{u}(n).$$

The new update equation of the filter coefficients is called the Normalized LMS, and is given by $$w(n+1) = w(n) + \frac{\tilde{\mu}}{a+\|\bar{u}(n)\|^2}\bar{u}(n)e(n),$$

where $0<\tilde{\mu}<2$, and a is a positive protection constant.

There are many more different alternatives to the LMS algorithm, where the step size is modified. One of them is to use a variable adaptation step, $$w(n+1)=w(n)+\alpha(n)\bar{u}(n)e(n),$$

where α(n) for example may be, $$\alpha(n) = \frac{1}{n+c},$$

where c is a positive constant. It is also possible to choose independent adaptation steps for each filter coefficient in the LMS algorithm, e.g., according to, $$w(n+1)=w(n)+A\bar{u}(n)e(n),$$

where A is given by, $$A = \begin{bmatrix} \alpha_1 & 0 & 0 & \cdots & 0 \\ 0 & \alpha_2 & 0 & \cdots & 0 \\ 0 & 0 & \alpha_3 & \cdots & 0 \\ \vdots & \vdots & \vdots & \ddots & \vdots \\ 0 & 0 & 0 & \cdots & \alpha_M \end{bmatrix}.$$

If instead the following cost function $$J(n)=E\{|e(n)|\}$$

is used, then the update equation becomes $$w(n+1)=w(n)+\alpha\operatorname{sign}[e(n)]\bar{u}(n).$$

This adaptive filter is called the Sign LMS, which is used in applications with extremely high requirements on low computational complexity.

Another adaptive filter is the Leaky LMS, which uses a constrained minimization with the following cost function $$J(n)=E\{|e(n)|^2\}+\alpha\|w(n)\|^2.$$

This constraint has the same effect as if white noise with variance α was added to the predicted signal profile u(n). As a result, the uncertainty in the input signal u(n) is increased, which tends to hold the filter coefficients back. The Leaky LMS is preferably used when R, the correlation matrix of u(n), has one or more eigenvalues equal to zero. However, in systems without noise, the Leaky LMS makes performance poorer. The update equation of the filter coefficients for the Leaky LMS is given by, $$w(n+1)=(1-\mu\alpha)w(n)+\mu\bar{u}(n)e(n).$$

Instead of minimizing the MSE cost function as above, the Recursive Least Squares (RLS) adaptive filter algorithm minimizes the following cost function $$J(n) = \sum_{i=1}^{n} \lambda^{n-i} |e(i)|^2,$$

where λ is called forgetting factor, 0≤λ≤1, and the method is called Exponentially Weighted Least Squares. It may be shown that the update equations of the filter coefficients for the RLS algorithm are, after the following initialization $$w(0)=0_{M\times 1}$$

$$P(0)=\delta^{-1}I_{M\times M}$$

where $I_{M \times M}$ is the identity matrix M×M, given according to $$k(n) = \frac{\lambda^{-1}P(n-1)\bar{u}(n)}{1+\lambda^{-1}\bar{u}^T(n)P(n-1)\bar{u}(n)}$$

$$\xi(n) = d(n) - w^T(n-1)\bar{u}(n)$$

$$w(n) = w(n-1) + k(n)\xi(n)$$

$$P(n) = \lambda^{-1}P(n-1) - \lambda^{-1}k(n)\bar{u}^T(n)P(n-1),$$

where ζ is a small positive constant for high signal-to-noise ratio (SNR), and a large positive constant for low SNR, $\delta<<0.01\sigma_u^2$, and ζ(n) corresponds to e(n) in the preceding algorithms. During the initialization phase the following cost function $$J(n) = \sum_{i=1}^{n} \lambda^{n-i} |e(i)|^2 + \delta\lambda^n \|w(n)\|^2,$$

is minimized instead, due to the use of the initialization $P(0)=\delta^{-1}$ I. The RLS algorithm converges in approximately 2M iterations, which is considerably faster than for the LMS algorithm. Another advantage is that the convergence of the RLS algorithm is independent of the eigenvalues of R, which is not the case for the LMS algorithm.

Several RLS algorithms running in parallel may be used with different λ and δ, which may be combined in order to improve performance, i.e., λ=1 may also be used in the algorithm (steady state solution) with many different δ:s.

It should be noted that both the LMS algorithm and the RLS algorithm can be implemented in fixed-point arithmetic, such that they can be run on a processor that has no floating point unit, such as a low-cost embedded microprocessor or microcontroller.

Figure 23A:
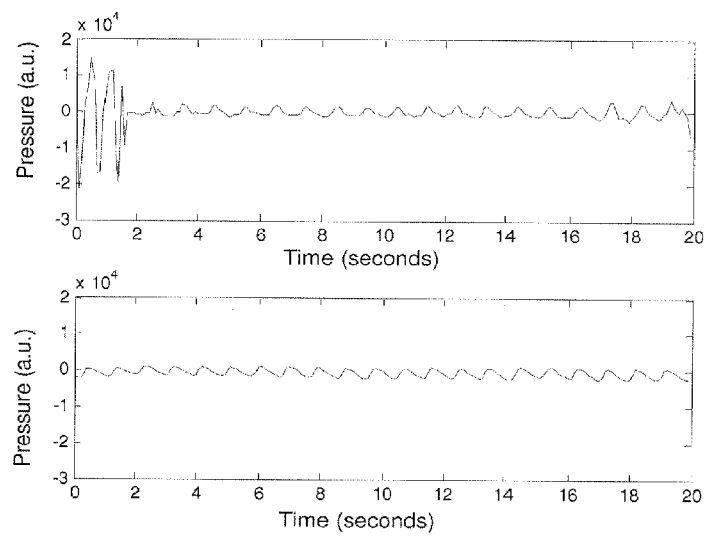
FIG. 23(*a*) illustrates a filtered pressure signal (top) and a corresponding heart signal (bottom), obtained from a venous pressure sensor, and FIG. 23(*b*) illustrates a filtered pressure signal (top) and a corresponding heart signal (bottom), obtained from an arterial pressure sensor.

To illustrate the effectiveness of the removal process using an adaptive filter, the top graph in FIG. 23(a) illustrates the error signal e(n) output by the adaptive filter structure in FIG. 22, using an RLS algorithm as adaptive update algorithm 32, operating on a measurement signal from the venous sensor 4a in FIG. 15, at a flow rate of 430 ml/min. The adaptive filter structure is provided with a predicted signal profile obtained in a reference measurement at the same flow rate. The RLS algorithm, designed with M=15, converges after about 2M, which equals 3 seconds with the current sampling frequency of 10 Hz. The top graph thus shows the measurement signal after elimination of the first pulses. The bottom graph in FIG. 23(a) is included for reference, and shows the measurement signal from the venous sensor 4a while the blood pump 3 is stopped. Clearly, the adaptive filtering is operable to provide, after a convergence period, a monitoring signal that properly represents the second pulses.

Figure 23B:
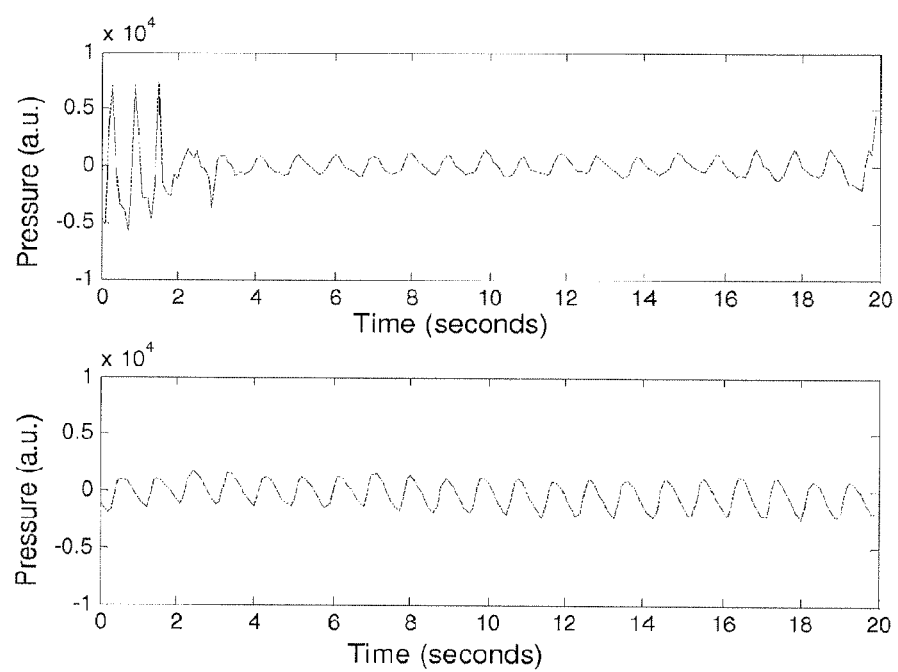

FIG. 23(b) corresponds to FIG. 23(a), but is obtained for a measurement signal from the arterial sensor 4b in FIG. 15.

Irrespective of implementation, the performance of the adaptive filter 30 (FIG. 22) may be further improved by switching the adaptive filter 30 to a static mode, in which the update algorithm 34 is disabled and thus the filter coefficients of the filter 32 (FIG. 22) are locked to a current set of values. The switching of the adaptive filter 30 may be controlled by an external process that analyses the second pulses in the error signal e(n), typically in relation to first pulse data. The first pulse data may be obtained from the measurement signal, a reference signal (see above), a dedicated pulse sensor, a control unit for the first pulse generator, etc. The adaptive filter 30 may be switched into the static mode if the external process reveals that the rate of second pulses starts to approach the rate of the first pulses and/or that the amplitude of the second pulses is very weak (in relation to an absolute limit, or in relation to a limit given by the amplitude of the first pulses). The adaptive filter may remain in static mode for a predetermined time period, or until released by the process.

The invention has mainly been described above with reference to a few embodiments. However, as readily appreciated by a person skilled in the art, other embodiments than the ones disclosed above are equally possible with the scope and spirit of the invention, which is defined and limited only by the appended patent claims.

For example, the measurement and reference signals may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, accelerometers, etc.

Although FIG. 12 indicates that the pressure sensor 4a-4c is connected to the first sub-system S1, it may instead be connected to measure the fluid pressure in the second sub-system S2. Further, the fluid containing system need not be partitioned into first and second sub-systems S1, S2 connected via a fluid connection C, but could instead be a unitary fluid containing system associated with a first pulse generator and a second pulse generator, wherein the each pressure sensor is arranged in the fluid containing system to detect a first pulse originating from the first pulse generator and a second pulse originating from the second pulse generator.

Further, the inventive technique is applicable for monitoring in all types of extracorporeal blood flow circuits in which blood is taken from the systemic blood circuit of the patient to have a process applied to it before it is returned to the patient. Such blood flow circuits include circuits for hemodialysis, hemofiltration, hemodiafiltration, plasmapheresis, apheresis, extracorporeal membrane oxygenation, assisted blood circulation, and extracorporeal liver support/dialysis. The inventive technique is likewise applicable for monitoring in other types of extracorporeal blood flow circuits, such as circuits for blood transfusion, infusion, as well as heart-lung-machines.

The inventive technique is also applicable to fluid systems containing other liquids than blood.

Further, the inventive technique is applicable to remove pressure pulses originating from any type of pumping device, not only rotary peristaltic pumps as disclosed above, but also other types of positive displacement pumps, such as linear peristaltic pumps, diaphragm pumps, as well as centrifugal pumps. In fact, the inventive technique is applicable for removing pressure pulses that originate from any type of pulse generator, be it mechanic or human.

Likewise, the inventive technique is applicable to isolate pressure pulses originating from any type of pulse generator, be it human or mechanic.

The inventive technique need not operate on real-time data, but could be used for processing off-line data, such as a previously recorded measurement signal.

This section makes reference to FIGS. 24-43 to describe methods and devices for monitoring the integrity of a fluid connection.

Figure 24:
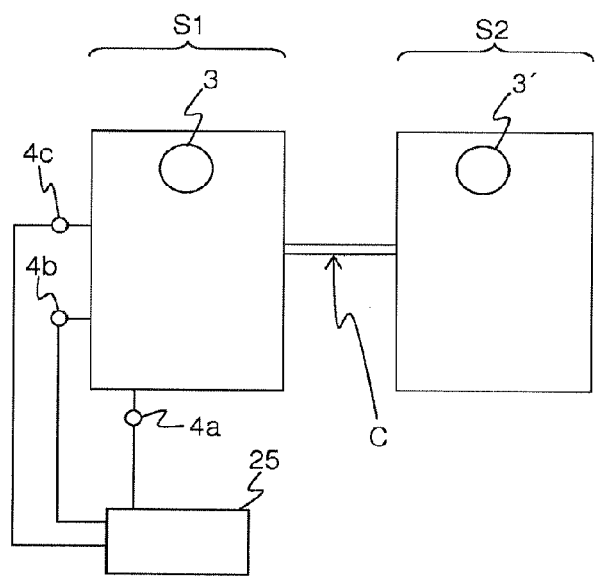
FIG. 24 is a schematic view of a general fluid arrangement in which the inventive concepts may be used for monitoring the integrity of a fluid connection.

FIG. 24 illustrates a general fluid arrangement in which a fluid connection C is established between a first fluid containing system S1 and a second fluid containing system S2. The fluid connection C may or may not transfer fluid from one system to the other. A first pulse generator 3 is arranged to generate a series of pressure waves in the fluid within the first system S1, and a second pulse generator 3' is arranged to generate a series of pressure waves in the fluid within the second system S2. A pressure sensor 4c is arranged to measure the fluid pressure in the first system S1. As long as the fluid connection C is intact, pressure waves generated by the second pulse generator 3' will travel from the second system S2 to the first system S1, and thus second pulses originating from the second pulse generator 3' will be detected by the pressure sensor 4c in addition to first pulses originating from the first pulse generator 3. It is to be noted that either one of the first and second pulse generators 3, 3' may include more than one pulse-generating device. Further, any such pulse-generating device may or may not be part of the respective fluid containing system S1, S2.

The fluid arrangement of FIG. 24 further includes a surveillance device 25 which is connected to the pressure sensor 4c, and possibly to one or more further pressure sensors 4a, 4b, as indicated in FIG. 24. Thereby, the surveillance device 25 acquires one or more measurement signals that are time-dependent to provide a real time representation of the fluid pressure in the first system S1. The surveillance device 25 monitors the integrity of the fluid connection C, based on the principle that the presence of second pulses indicates that the fluid connection C is intact, whereas absence of second pulses indicates that the fluid connection C is compromised. The absence of second pulses may bring the surveillance device 25 to issue an alarm or warning signal, and/or alert a control system of the first or second fluid containing systems S1, S2 to take appropriate action.

The surveillance device 25 is thus configured to continuously process the time-dependent measurement signal(s) to determine whether second pulses are present or not. Typically, the determination involves analyzing the measurement signal(s), or a pre-processed version thereof, in the time domain to calculate a value of an evaluation parameter which is indicative of the presence or absence of second pulses in the measurement signal(s). Depending on implementation, the surveillance device 25 may use digital components or analog components, or a combination thereof, for receiving and processing the measurement signal(s).

In the context of the present disclosure, "absence" of a pulse may imply that the pulse has disappeared, or at least that it has decreased sufficiently in magnitude compared to the pulse deemed to be "present". The assessment of presence or absence may involve calculating an evaluation parameter value based on the measurement signal(s) and comparing the parameter value to a threshold value.

First Inventive Concept

Figure 25:
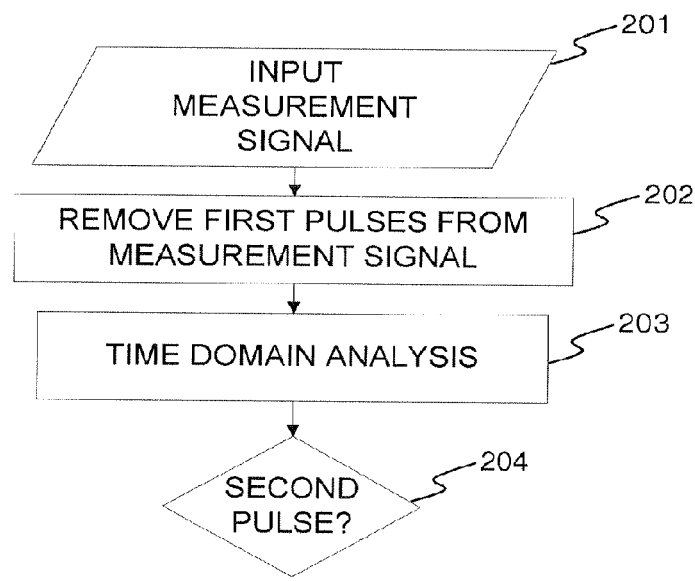
FIG. 25 is a flow chart of a monitoring process according to a first inventive concept.
Figure 26:
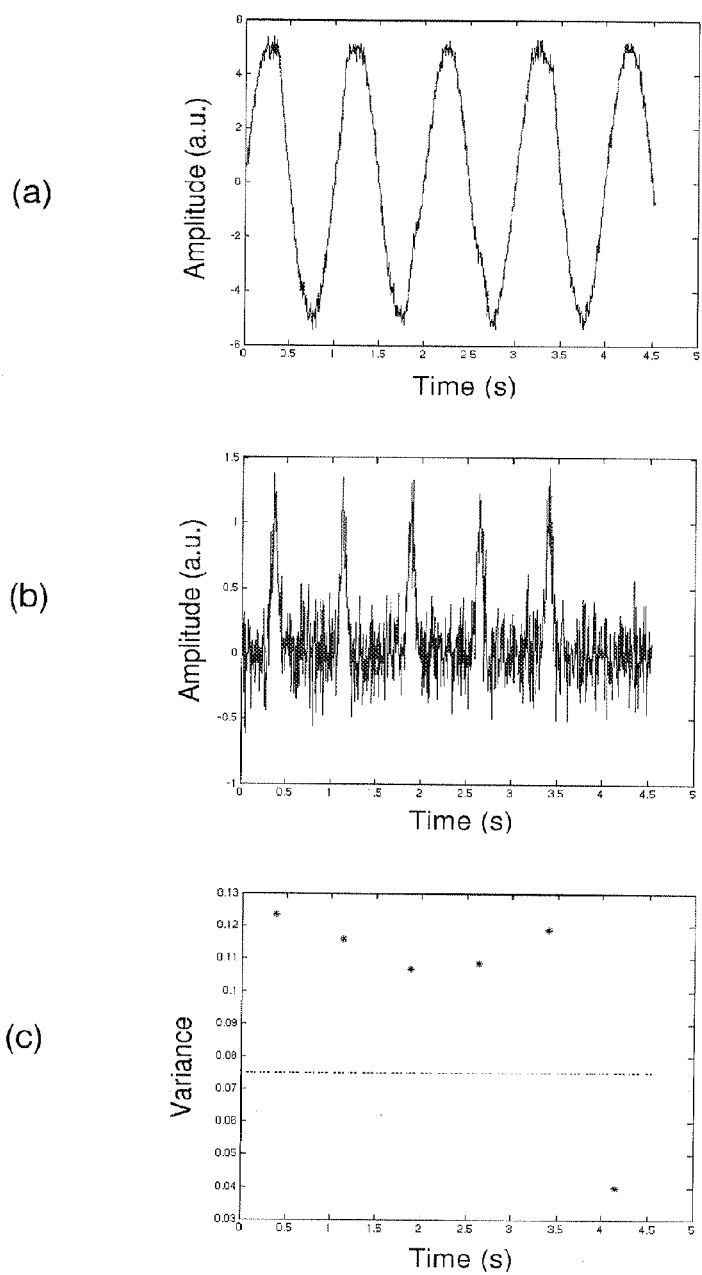
FIG. 26(*a*) is a plot of the measurement signal as a function of time, FIG. 26(*b*) is a plot of the measurement signal in FIG. 26(*a*) after filtering, and FIG. 26(*c*) illustrates a statistical dispersion measure calculated for a sequence of time windows in the signal in FIG. 26(*b*).
Figure 27:
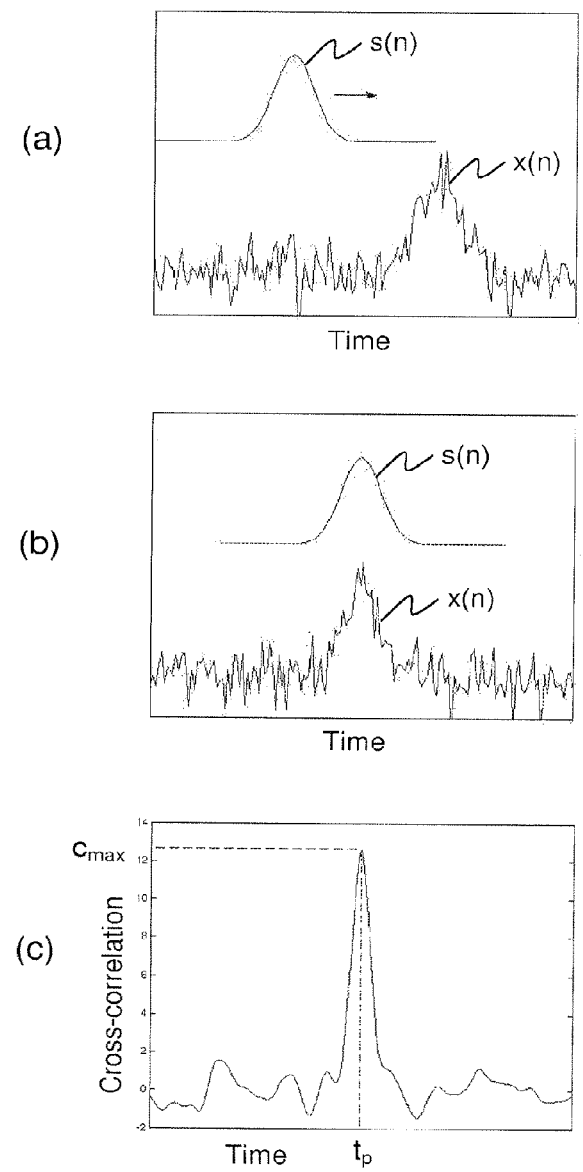
FIG. 27(*a*) illustrates a matching procedure between a measurement signal and a predicted signal profile, FIG. 27(*b*) illustrates the position of best match, and FIG. 27(*c*) is a correlation curve resulting from the matching procedure in FIG. 27(*a*).
Figure 28:
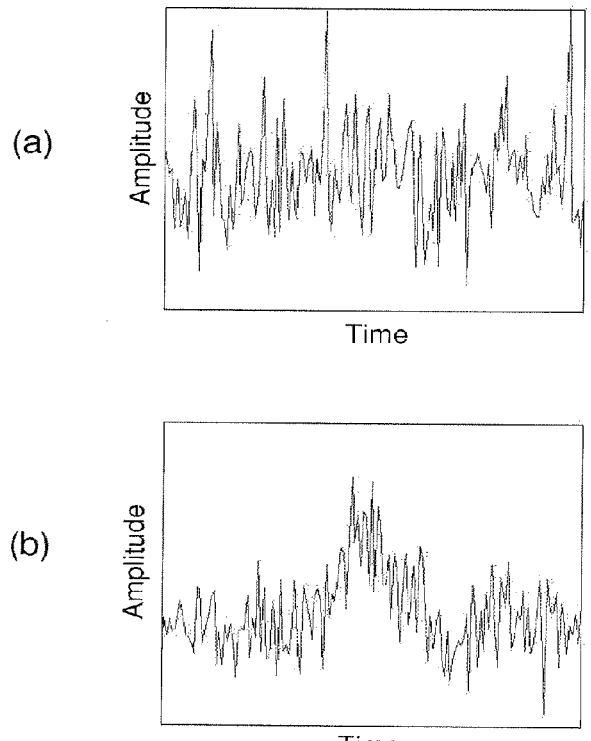
FIG. 28(*a*) is a plot of a signal segment containing a second pulse, and FIG. 28(*b*) is plot of an evaluation segment generated by averaging ten signal segments.

FIG. 25 is a flow chart that illustrates steps of a monitoring process according to a first inventive concept. A measurement signal is received (step 201) and subjected to a filtering process (step 202) that essentially removes the first pulses from the measurement signal, while leaving at least part of the second pulses intact. The filtered measurement signal is then subjected to a time domain analysis (step 203), in which a value of an evaluation parameter is calculated based on signal values within a time window in the filtered measurement signal, which is denoted "evaluation segment" in the following. The calculation is typically designed such that the evaluation parameter represents the distribution of signal values within the evaluation segment. Based on the resulting value of the evaluation parameter, it is decided (step 204) whether the fluid connection is intact or not, typically by comparing the resulting value to a threshold value.

For continuous surveillance, a time sequence of evaluation parameter values is calculated based on a time sequence of evaluation segments obtained from the measurement signal. These evaluation segments may be overlapping or non-overlapping in time. In one embodiment, individual sections of the measurement signal are acquired, filtered and analyzed, one after the other. Each evaluation segment may correspond to one such section of the measurement signal; the time window is thus applied already when the measurement signal is acquired. In another embodiment, the measurement signal is continuously acquired and filtered, whereupon evaluation segments are extracted from the filtered signal and analyzed.

FIG. 26(a) shows an example of a time-dependent measurement signal containing first and second pulses with a relative magnitude of 10:1. The first and second pulses have a frequency of 1 Hz and 1.33 Hz, respectively. FIG. 26(b) shows the time-dependent measurement signal after removal of the first pulses, leaving only second pulses and noise. It should be noted that there is an absence of second pulses after about 4 seconds. FIG. 26(c) illustrates a variance measure calculated for a sequence of non-overlapping time windows in the filtered measurement signal in FIG. 26(b), each time window being about 0.75 seconds. Clearly, by using the variance measure as an evaluation parameter, it is possible to detect the absence of the second pulse at the time point of about 4 seconds. An exemplifying threshold value is indicated by a dotted line.

The first inventive concept has the potential of providing a comparatively robust measure of the integrity of the fluid connection C. By analyzing the temporal distribution of signal values within the evaluation segment, an improved tolerance to noise and disturbing signals may be obtained.

Furthermore, compared to techniques that rely on frequency domain analysis of the measurement signal for detecting the presence of second pulses, the first inventive concept may provide an improved tolerance to variations in the pulse repetition interval of the second pulse generator 3', since the first inventive concept relies on a time domain analysis. Such variations may occur, e.g., when the second pulse generator 3' is a human heart, and the second system S2 thus is the blood system of a human. Variations in heart rhythm (heart rate variability, HRV) will cause the peak from the heart in the frequency domain to be smeared out, making it harder to detect. In healthy subjects under calm conditions, HRV may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients.

As long as the time window is selected such that each evaluation segment contains at least one second pulse, the presence/absence of second pulses will affect the evaluation parameter, if properly chosen. A fixed-length time window may be used, with the length of the time window being chosen with respect to a maximum pulse repetition rate of the second pulse generator 3'. The length of the time window may be set by constraints in the second pulse generator 3' or by a selected performance limit of the surveillance method. Alternatively, the length of the time window and/or the location of the time window in the filtered measurement signal may be selected based on a predicted timing of the second pulse(s) to be detected. The acquisition and use of such a predicted timing ("timing information") will be further exemplified below with reference to the second inventive concept.

Still further, the time domain analysis according to the first inventive concept may allow for faster detection than a frequency domain analysis, since the former may have the ability to detect a single second pulse in the evaluation segment whereas the generation of a frequency spectrum requires a greater number of second pulses in the evaluation segment. Thus, frequency domain analysis may be associated with a greater time lag than time domain analysis.

The evaluation parameter may be calculated as a statistical dispersion measure of the signal values within the evaluation segment. Non-limiting examples of potentially useful statistical dispersion measures include standard deviation ($\sigma$), variance ($\sigma^2$), coefficient of variation ($\sigma/\mu$) and variance-to-mean ($\sigma^2/\mu$). Other examples include a sum of differences, e.g. given by $$\sum_{i=2}^{n} |x_i - x_{i-1}|, \text{ or } \sum_{i=1}^{n} \sum_{j=1}^{n} |x_i - x_j|,$$

or an energy or power measure, such as $$\sum_{i=1}^{n} x_i^2,$$

with n being the number of signal values x in the evaluation segment. Yet other examples include a measure based on a sum of absolute differences from an average value m, with the average value m being calculated for the signal values in the evaluation segment using any suitable function, such as arithmetic mean, geometric mean, median, etc. It is to be noted that all of the above suggested dispersion measures also include normalized and/or weighted variants thereof.

As an alternative or supplement to calculating a statistical dispersion measure, the evaluation parameter may result from a matching procedure, in which the evaluation segment is matched to one or more predicted signal profiles of a second pulse. Preferably, but not necessarily, each predicted signal profile represents a single second pulse. Typically, the matching procedure involves convolving or cross-correlating the evaluation segment and the predicted signal profile, and the evaluation parameter value is a resulting correlation value, typically the maximum correlation value.

A matching procedure based on cross-correlation is further exemplified in FIGS. 27(a)-27(c). The matching procedure is used to distinguish between the hypotheses $H_0: x(n) = w(n)$ $H_1: x(n) = s(n) + w(n)$ with x(n) being the evaluation segment, w(n) being an error signal representing disturbances introduced by noise/signal interference/measurement errors, etc, and s(n) being the predicted signal profile of the second pulse. If $H_1$ is deemed more likely than $H_0$, then a second pulse has been identified and the fluid connection C is deemed intact. If $H_0$ is deemed more likely than $H_1$, then a second pulse cannot be identified and the fluid connection C may be compromised.

FIG. 27(a) is a graph showing an example of a predicted signal profile s(n) and an evaluation segment x(n). In this particular example, the evaluation segment has a signal-to-noise ratio (SNR) of 4.8 dB, i.e. the energy of the signal profile s(n) is 3 times the energy of the error signal w(n). During the cross-correlation, the signal profile s(n) is slid in a number of time steps along the time axis, as indicated by arrow in FIG. 27(a), and the integral of the product s(n)·x(n) is calculated for each time step. The cross-correlation thus results in a time sequence of correlation values, with the maximum correlation value indicating the time point of best match between x(n) and s(n). FIG. 27(b) illustrates the relative position between x(n) and s(n) at the time point for best match, and FIG. 27(c) illustrates the resulting correlation values as a function of said time steps. The magnitude of the maximum correlation value, optionally calculated as a weighted average within a range around the maximum correlation value ($c_{max}$), may thus be used to distinguish between the above hypotheses.

As indicated in FIG. 27(c), the matching procedure not only identifies the presence of a second pulse, it also provides an indication of the location of the second pulse in the evaluation segment, given by the time point ($t_p$) for the maximum correlation value ($c_{max}$). This time point may be used to assess the reliability of the determined maximum correlation value, by comparing this time point to a predicted time point. Such a predicted time point may be obtained from aforesaid timing information, as will be further explained below in relation to the second inventive concept.

The predicted signal profile may be generated as an average of a number of recordings of second pulses. For example, it may be generated by averaging a number of evaluation segments, before and/or during the monitoring process.

To improve the signal quality of the predicted profile, with or without averaging, the measurement signal may be acquired while the first pulse generator is stopped, whereby the measurement signal is free of first pulses. Thus, the first pulse generator may be intermittently stopped during the monitoring process for calculation of an updated signal profile of the second pulses.

In another variant, the predicted signal profile is obtained from one or more reference signals originating from a reference pressure sensor (e.g. any one of pressure sensors 4a-4c in FIG. 24) in the first system. Such a reference pressure sensor is suitably arranged to detect second pulses even if the fluid connection is compromised, e.g. via a second fluid connection between the first and second fluid containing systems. The reference pressure sensor may be installed to be isolated from the first pulses, such that the reference signal is essentially free of first pulses. Alternatively, if the reference signal includes both first and second pulses, the reference signal may be subjected to a filtering process (e.g. according to step 202 in FIG. 25) to remove the first pulses while leaving the second pulses intact in the reference signal. An example of such a reference pressure sensor is an arterial pressure sensor in an extracorporeal blood flow circuit, to be further described below. In such an extracorporeal blood flow circuit, the measurement signal(s) may originate from one or more venous pressure sensors, e.g. if the monitoring process aims at monitoring the integrity of the venous-side fluid connection between the extracorporeal blood flow circuit and a patient.

In one specific implementation, the reference signal is obtained continuously or intermittently during the monitoring process, and the predicted signal profile is continuously or intermittently calculated based on the reference signal. Thus, in the context of the above-mentioned extracorporeal blood flow circuit, the integrity of the venous-side fluid connection may be monitored by continuously matching evaluation segments from the venous pressure sensor against a predicted signal profile obtained from the arterial pressure sensor. It is even conceivable that the predicted signal profile is updated for each evaluation segment (denoted "synchronous monitoring" in the following). The matching procedure may benefit from the use of timing information, as will be further explained below in relation to the second inventive concept. Alternatively, the predicted signal profile may be pre-generated, e.g. by averaging recordings of second pulses from a number of fluid arrangements, similar to the one that is being monitored (cf. FIG. 24). Optionally, such a pre-generated signal profile may be adapted to specifics of the fluid arrangement to be monitored, by applying a mathematical model taking into account arrangement-specific parameters, such a type of fluid connection, flow rate, fluid characteristics, etc. Alternatively, the predicted signal profile may be obtained entirely by mathematical modelling based on arrangement-specific parameters. According to yet another alternative, a standard profile is used as predicted signal profile, e.g. a bell-shaped function such as a Gaussian distribution function.

In order to improve the detection of second pulses, it is conceivable to subject the filtered measurement signal/evaluation segment to a signal enhancement process, which removes high-frequency components (cf. error signal w(n)), before calculation of the evaluation parameter value. Such a signal enhancement process may involve subjecting the filtered measurement signal/evaluation segment to a low-pass filtering. However, a more significant improvement in SNR of the evaluation segment may be achieved by averaging several consecutive second pulses in the filtered measurement signal, again based on the above-mentioned predicted timing of the second pulse(s) (i.e. timing information). Such a signal enhancement process would thus involve using the predicted timing to identify a set of second pulse segments in the filtered measurement signal, aligning the second pulse segments in the time domain based on the predicted timing, and generating an average representation by summing the aligned signal values for each time value in the time domain. Optionally, the average representation is normalized by the number of second pulse segments to generate a true average. The average representation may then be used as the above-mentioned evaluation segment, or the evaluation segment may be extracted from a time window within the average representation.

The signal enhancement process is further exemplified in FIGS. 28(a)-28(b). FIG. 28(a) is a time domain representation of a filtered measurement signal x(n)=s(n)+w(n) with a SNR of −9 dB, i.e. the energy of the error signal w(n) is 8 times the energy of the signal profile s(n), making time domain analysis for detection of the second pulse difficult, if not impossible. FIG. 28(b) is a time domain representation after averaging of 10 different second pulse segments similar to the one in FIG. 28(a). Clearly, the SNR has been improved significantly, allowing a second pulse to be detected using time domain analysis.

It is to be understood that the monitoring process of FIG. 25 may operate on more than one measurement signal, if the fluid arrangement to be monitored includes more than one pressure sensor (cf. 4a, 4b in FIG. 24). In such a configuration, the above-described signal enhancement process may involve using aforesaid timing information to identify and average second pulse segments from at least two filtered measurement signals originating from different pressure sensors. Thus, the second pulse segments may be extracted from plural time windows in each measurement signal, and/or from one or more time windows in different measurement signals.

The filtering process according to step 202 in FIG. 25 aims at removing the first pulses from the measurement signal to such an extent that the second pulses can be detected by the subsequent time domain analysis (step 203). For example, a comb filter and/or a combination of bandstop or notch filters, typically cascade coupled, may be operated on the measurement signal to block out all frequency components originating from the first pulse generator 3. Alternatively, such blocking may be achieved by the use of one or more adaptive filters and notch-equivalent filters, e.g. as disclosed in aforesaid WO 97/10013. In yet another alternative embodiment, the measurement signal is processed in the time domain to cancel the first pulses. In such an embodiment, a standard signal profile of the first pulses may be obtained, which is then subtracted from the measurement signal at suitable amplitude and phase. The phase is indicated by phase information which may be obtained from a signal generated by a phase sensor coupled to the first pulse generator 3, or from a control signal for the first pulse generator 3. The standard signal profile may be obtained from one or more of the pressure sensors 4a-4c in the first fluid containing circuit S1, suitably by identifying and averaging a set of first pulse segments in the measurement signal(s) similarly to the above-mentioned signal enhancement process. The standard signal profile may or may not be updated intermittently during the monitoring process. Alternatively, a predetermined standard signal profile is used, which optionally may be modified according to a mathematical model accounting for wear in the first pulse generator, fluid flow rates, tubing dimensions, speed of sound in the fluid, etc. It should be noted that by filtering the measurement signal in the time domain, instead of the frequency domain, it is possible to eliminate the first pulses and still retain the second pulses, even if the first and second pulses overlap in the frequency domain.

Second Inventive Concept

Figure 29:
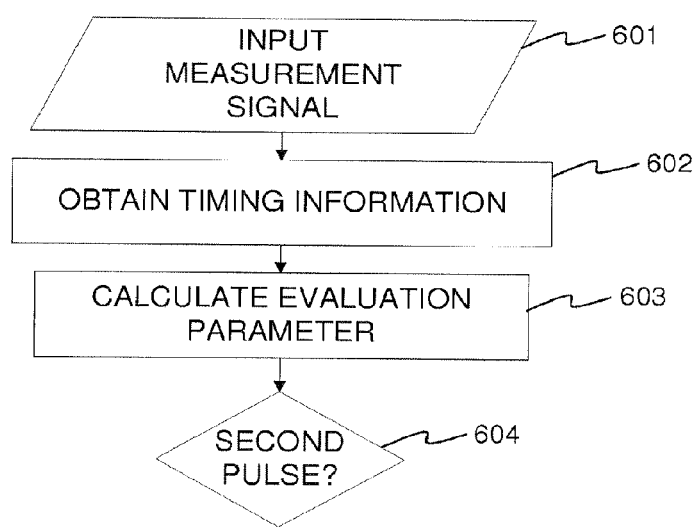
FIG. 29 is a flow chart of a monitoring process according to a second inventive concept.

FIG. 29 is a flow chart that illustrates steps of a monitoring process according to a second inventive concept. In this process, a measurement signal is received (step 601) and timing information is obtained, from the measurement signal or otherwise (step 602). The timing information is indicative of the timing of second pulses in the measurement signal. Subsequently, the measurement signal is processed (step 603) based on the timing information, to calculate a value of an evaluation parameter which is indicative of the presence or absence of a second pulse in the measurement signal. Based on the resulting value of the evaluation parameter, it is decided (step 604) whether the fluid connection is intact or not, typically by comparing the resulting value to a threshold value.

Thus, in the second inventive concept, timing information indicates the expected position of a second pulse in the measurement signal. This additional information may allow the second pulse to be identified from other types of signal features, e.g. different/simpler evaluation parameters, and/or it may allow for an increased reliability in detecting presence/absence of second pulses.

Furthermore, as explained above, the provision of timing information allows for signal enhancement by identifying and averaging second pulse segments in one or more measurement signals. The signal enhancement may increase the SNR of the measurement signal, allowing for the use of a rudimentary measure as evaluation parameter, such as signal amplitude, local maximum, local average, etc. This may serve to improve the processing speed and/or allow for less sophisticated detection equipment.

It is to be understood that the second inventive concept can be combined with any of the features of the first inventive concept. For example, the measurement signal may be filtered to remove first pulses, and the evaluation parameter may be calculated for an evaluation segment given by signal values within a time window in the filtered measurement signal. Also, any one of the evaluation parameters suggested in relation to the first inventive concept is equally applicable to the second inventive concept. It is to be noted, however, that the filtering of the measurement signal is not an essential feature of the second inventive concept, since the use of timing information may allow second pulses to be detected in the measurement signal even in the presence of first pulses.

The second inventive concept may also improve the detection speed, since the timing information may provide a predicted time point for the second pulse in the measurement signal/filtered measurement signal/evaluation segment. Thereby, the number of signal values that need to be processed for calculation of the evaluation parameter value may be reduced. For example, the aforesaid matching procedure may be simplified, since the correlation between the predicted signal profile and the evaluation segment need only be calculated for the predicted time point, or a confined time range around this predicted time point. Correspondingly, the calculation of a statistical dispersion measure or the above-mentioned rudimentary measure may be simplified, since the provision of timing information makes it possible to reduce the size of the time window for extracting the evaluation segment, while still ensuring that each evaluation segment includes at least one second pulse. For example, the size of the time window may be reduced if the timing information indicates a shortened pulse interval between the second pulses, and/or the time window may be centred on the predicted time point of each second pulse.

Still further, the second inventive concept allows for assessing the reliability of a calculated evaluation parameter value, by comparing a time point associated with the evaluation parameter value with a predicted time point given by the timing information. For example, the time point for a maximum correlation value obtained in the aforesaid matching procedure may be compared with a predicted time point for a second pulse. If these time points deviate too much, the monitoring process may determine that a second pulse is absent, even though the magnitude of the correlation value might indicate presence of a second pulse.

The timing information may be obtained in any one of a plurality of different ways. For example, the timing information may be extracted from the output signal of a pulse sensor coupled to the second fluid containing system. The output signal may indicate individual second pulses or an average time between second pulses. In either case, a predicted time point for a second pulse in the measurement signal can be calculated based on the output signal of the pulse sensor and a known difference in arrival time between the pulse sensor and the pressure sensor(s) that generates the measurement signal(s). The pulse sensor may sense the pressure waves that are generated in the fluid by second pulse generator, or it may directly reflect the pulse generation process in the second pulse generator, e.g. via a control signal for the second pulse generator or a pulse rate meter mechanically coupled to the second pulse generator. In one application, to be further exemplified below, the second fluid containing system is a blood system of a human, and the pulse generator is a human heart. In such an application, the timing information may be provided by any conventional pulse sensor such as a pulse watch, a pulse oximeter, an electrocardiograph, etc.

Alternatively, the timing information may be obtained based on the relative timing of previously detected second pulses in the measurement signal, e.g. given by the time points associated with previously calculated evaluation parameter values. For example, the time difference between the two most recently detected second pulses may be used to predict the time point for subsequent second pulse(s).

Alternatively, the timing information may be obtained from one or more reference signals originating from a reference pressure sensor in the first system. Such a reference pressure sensor is suitably arranged to detect second pulses even if the fluid connection is compromised, e.g. via a second fluid connection between the first and second fluid containing systems.

An example of such a reference pressure sensor is an arterial pressure sensor in an extracorporeal blood flow circuit, to be further described below. In such an extracorporeal blood flow circuit, the measurement signal(s) may originate from one or more venous pressure sensors, e.g. if the monitoring process aims at monitoring the integrity of the venous-side fluid connection between the extracorporeal blood flow circuit and a patient. The reference signal may be processed for detection of at least one second pulse, using any suitable technique, including the time domain techniques disclosed herein. The time point of the detected second pulse in the reference signal can then be converted to a predicted time point in the measurement signal/filtered measurement signal/evaluation segment using a known/measured difference in pulse arrival/transit time between the reference sensor and the pressure sensor(s) used for monitoring. Thus, in one embodiment, the difference in transit time is given by a fixed and predefined value.

In another embodiment, the difference in transit time between a blood line on the arterial side and a blood line on the venous side in the extracorporeal blood flow circuit is determined based on the actual arterial and venous pressures (absolute, relative, or average), which may be derived from any suitable sensor in the extracorporeal blood flow circuit (including the venous and arterial pressure sensors). The transit time decreases if the pressure increases, i.e., high pressure equals short transit time. During operation of the extracorporeal blood flow circuit, the venous pressure should be higher than the arterial pressure, and thus the transit time should be shorter in the venous blood line compared to the transit time in the arterial blood line. The difference in transit time may be determined based on, e.g., a physical model or a look-up table. The model/table may not only include information about pressure (absolute, relative, or average), but also information about material (elasticity, plasticity, etc), geometry (length, diameter, wall thickness, etc), temperature (both fluids and ambient temperature), mechanical factors (clamp, tension, actuators, kinking/occlusion, etc), fluid properties (viscosity, water/blood, chemical composition, etc), etc. The thus-determined difference in transit time may then be used to relate a time point of a detected second pulse in the reference signal from the arterial pressure sensor to a predicted time point in the measurement signal/filtered measurement signal/evaluation segment originating from the venous pressure sensor.

In a variant, an improved estimation of the timing information may be obtained by aligning and adding the filtered measurement signal/evaluation segment (derived from the venous pressure signal) with a correspondingly filtered reference signal (derived from the arterial pressure signal), to thereby calculate an average time-dependent signal with improved SNR. The aligning may be based on the aforesaid difference in transit time, given by the actual arterial and venous pressures (absolute, relative, or average). By identifying one or more second pulse(s) in the average time-dependent signal, an improved estimation of the timing information is obtained.

Alternatively or additionally, to potentially improve the precision of the timing information, the timing information may be obtained by intermittently stopping the first pulse generator, while identifying at least one second pulse in the reference signal or the measurement signal.

Optionally, the process of obtaining timing information based on an identified second pulse, be it in the reference signal or the measurement signal, may involve validating the identified second pulse (a candidate pulse) against a temporal criterion. Such a temporal criterion may, e.g., indicate an upper limit and/or a lower limit for the time difference between the time point for the candidate pulse and one or more previously identified (and suitably validated) second pulses. These limits may be fixed, or they may be set dynamically in relation to a preceding time difference. Any candidate pulse that violates the temporal criterion may be removed/discarded from use in obtaining the timing information.

In yet another alternative, the timing information is obtained from a measurement signal using an iterative approach. In this iterative approach, the measurement signal is processed to calculate a time-sequence of evaluation parameter values, e.g. based on the first inventive concept. These evaluation parameter values identify a sequence of candidate pulses and associated candidate time points, which is validated against a temporal criterion.

Such a temporal criterion may, e.g., indicate an upper limit and/or a lower limit for the time difference between the candidate time points. The temporal criterion may be given by constraints in the second pulse generator 3'. Any candidate time points that violate the temporal criterion may be removed/discarded, and the timing information may be obtained from the remaining time points.

Different validation methods may be used depending on the availability of previous timing information, i.e. information about time points of preceding second pulses. Such previous timing information may be given by any one of the methods described in the foregoing, or resulting from a previous iteration of the iterative approach.

FIG. 30(a) illustrates a sequence of candidate pulses (denoted by X), as well as a sequence of preceding second pulses (denoted by Y), laid out on a time axis. In a first validation step, predicted time points (arrows ↓ in FIG. 30(b)) are calculated based on the previous timing information (e.g. second pulses Y). In a second validation step, a first temporal criterion is applied to remove/discard any candidate pulses that lie too far from the predicted time points, as also shown in FIG. 30(b). In a third validation step, a second temporal criterion is applied to retain only the candidate pulse with the largest evaluation parameter value among any candidate pulses that lie too close to each other, as shown in FIG. 30(c).

Figure 30:
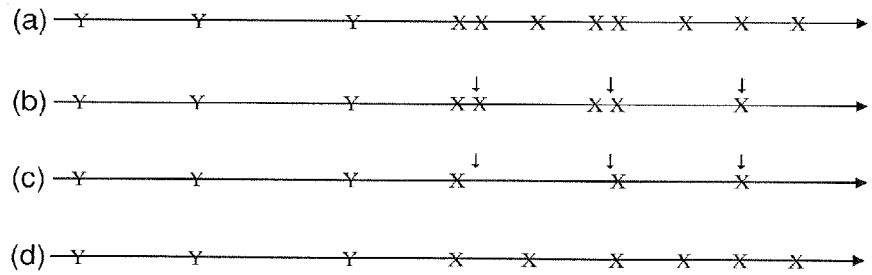
FIGS. 30(*a*)-(*d*) illustrate processing of candidate pulses identified in a measurement signal.
Figure 31:
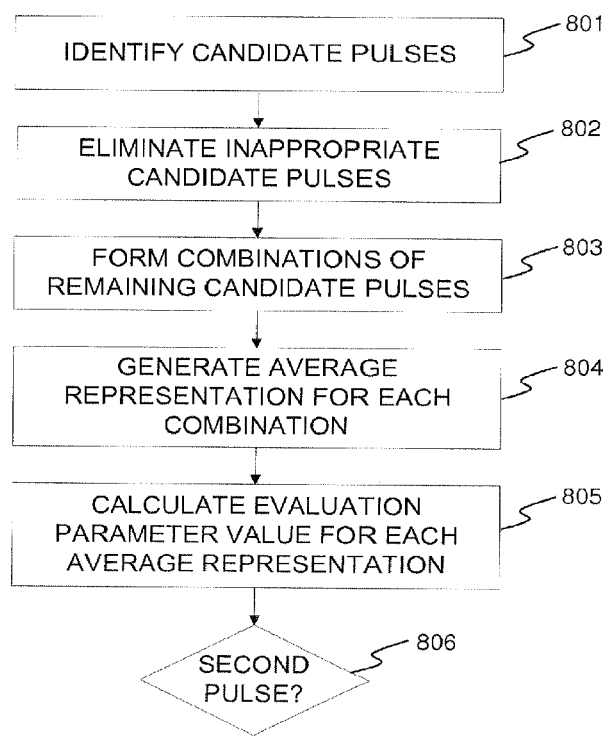
FIG. 31 is a flow chart of part of a monitoring process according to the second inventive concept.

A different validation method may be used if previous timing information is not available. FIG. 31 is a flow chart for such a validation method. The initial step 801 of identifying candidate pulses is followed by a first validation step 802, in which a first temporal criterion is applied to retain only the candidate pulse with the largest evaluation parameter value among any candidate pulses that lie too close to each other. FIG. 30(*d*) shows an exemplifying result of applying the first validation step 802 to the sequence of candidate pulses in FIG. 30(*a*). Then, in step 803, different combinations of the remaining candidate pulses are formed. In step 804, an average representation is calculated for each such combination, by aligning and summing corresponding signal segments of the measurement signal/filtered measurement signal. The combinations may be formed based on a second temporal criterion that defines an upper limit and/or a lower limit for the time difference between the candidate pulses. In a second validation step 805, an evaluation parameter value is calculated for each such average representation, and the maximum evaluation parameter value is extracted. Finally, in step 806, it is decided whether the fluid connection is intact or not, by comparing the maximum evaluation parameter value to a threshold value. If the maximum evaluation parameter value exceeds the threshold value, it may be concluded that a second pulse is present and that the fluid connection is intact. It may be noted that there is no need to explicitly extract the timing information in the validation method in FIG. 31, since the use of the timing information is embedded in the final step 806 of determining the integrity of the fluid connection.

It should also be noted that different evaluation parameters and/or threshold values may be used in steps 801 and 806. It is also conceivable to use a combination of two or more of the above alternative methods for obtaining the timing information.

Figure 32:
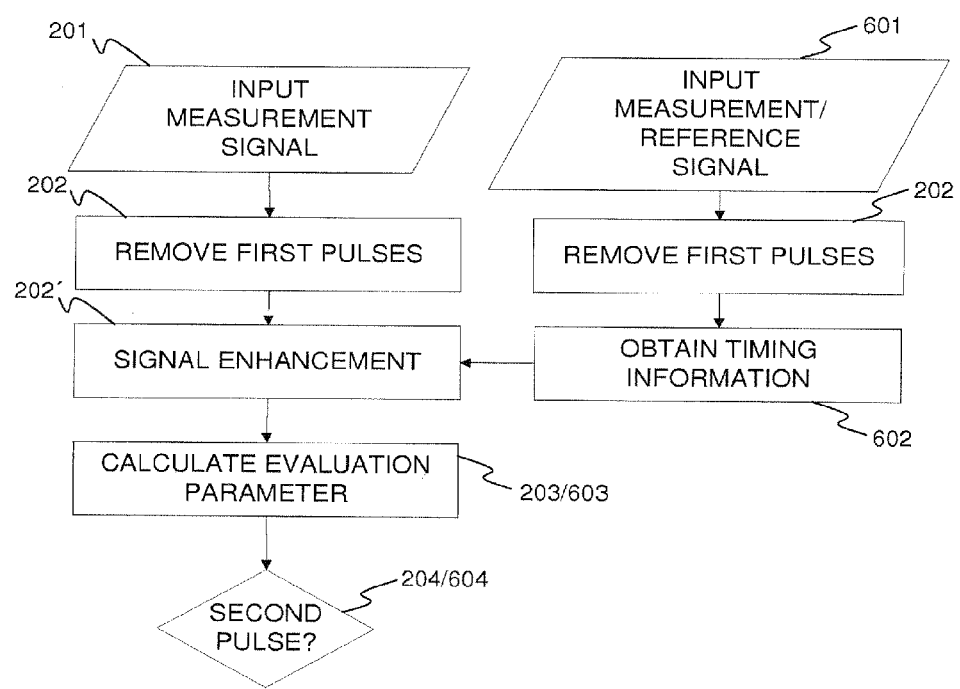
FIG. 32 is a flow chart of a monitoring process that combines the first and second inventive concepts.

FIG. 32 is a flow chart of an embodiment that combines features of the first and second inventive concepts. Specifically, a measurement signal is obtained and filtered according to steps 201 and 202 of the first inventive concept. Then, in step 202', the filtered measurement signal is processed for signal enhancement, based on timing information. As discussed above in relation to FIG. 28, step 202' typically involves identifying, aligning and summing a set of second pulse segments in the filtered measurement signal, to create an average signal representation. An evaluation parameter value is then calculated based on the enhanced signal representation according to step 203/603 of the first/second inventive concept, and it is decided whether the fluid connection is intact or not (steps 204/604). The method also involves receiving a measurement signal (which may be the same measurement signal as in step 201, or the aforesaid reference signal) according to step 601 of the second inventive concept. Then, the measurement/reference signal is filtered to remove the first pulse, if required, according to step 202 of the first inventive concept. Finally, the timing information is obtained according to step 602 of the second inventive concept.

Combinations of Monitoring Techniques

As explained in the foregoing, the technique for monitoring the integrity of the fluid connection can be based on either of the first and second inventive concepts, or a combination thereof. It is also possible to combine such an inventive monitoring technique with one or more conventional monitoring techniques, which e.g. involve the use of an air detector, or a comparison of average pressure levels with threshold values as described by way of introduction. Other conventional monitoring techniques are disclosed in aforesaid WO 97110013 and U52005/0010118.

It might also be desirable to combine the inventive monitoring techniques with other techniques that are specially designed to handle adverse operating conditions. One such operating condition may arise when the first and second pulses overlap in the frequency domain. As discussed above in relation to step 202 of FIG. 25, such an operating condition could be handled by filtering the measurement signal in the time domain. However, the monitoring precision may be increased further by combining the inventive monitoring technique with a phase-locking technique or a beating detection method, to be described in the following.

The phase-locking technique involves controlling the first/second pulse generator 3, 3' so as to synchronize the pulse rate of the first and second pulse generators 3, 3' while applying a phase difference between the first and second pulses. Thereby, the first and second pulses will be separated in time, and can be detected using the time domain analysis according to the first and/or second inventive concepts. The phase difference may be approximately 180°, since this may maximize the separation of the first and second pulses in the time domain. The phase-locking technique may be activated when it is detected that the frequency of the second pulse generator approaches a frequency of the first pulse generator, or vice versa.

The beating detection method is an alternative or complementary monitoring technique which involves evaluating the presence or absence of a beating signal in the measurement signal to determine the integrity of the fluid connection. The beating signal manifests itself as an amplitude modulation of the measurement signal and is formed by interference between pressure waves generated by the first pulse generator and pressure waves generated by the second pulse generator. Instead of trying to identify second pulses in the measurement signal, the presence of second pulses is identified via the secondary effect of beating. Generally, beating is a phenomenon which is especially noticeable when two signals with closely spaced frequencies are added together. Thus, the beating signal detection is inherently well-suited to be used when the first and second pulses are closely spaced in the frequency domain. The beating signal may or may not be detected by analysing the measurement signal in the time domain. Suitably, the beating detection involves obtaining one or more specific frequencies related to the first pulse generator, and creating at least one filtered measurement signal in which all but one of said specific frequencies are removed. The beating signal may then be detected by determining an envelope of the filtered measurement signal. The beating detection method is the subject of Applicant's co-pending Swedish patent application No. 0800890-6 and U.S. provisional patent application No. 61/045,642, both filed on Apr. 17, 2008.

It is to be understood that in any one of the above combinations, the different monitoring techniques may be carried out in series, in any order, or in parallel.

Performance Improvements

The performance of the different methods for monitoring the integrity of a fluid connection as described herein may be improved by applying any of the following variations.

Hypothesis Test

The determination of the integrity of the fluid connection between the first and second fluid containing systems could be represented by a hypothesis test. In this hypothesis test, the above-mentioned evaluation parameter value $\beta$ is compared to a threshold. The output of the hypothesis test is a decision, which may be "intact fluid connection" ($H_1$) if $\beta > \gamma_i$, "compromised fluid connection" ($H_0$) if $\beta < \gamma_0$, or "uncertain decision" if $\gamma_0 \leq \beta \leq \gamma_1$, wherein $\gamma_0$ and $\gamma_1$ are different thresholds.

Magnitude Dependent Monitoring Technique

The monitoring technique may be dynamically adjusted based on the magnitude of the first and/or second pulses in the measurement signal and/or in the reference signal. The dynamic adjustment may affect the process for obtaining timing information and/or the process for obtaining the parameter value based on the measurement signal.

For example, if the magnitude (e.g. amplitude) of second pulses in the reference signal are found to be smaller than the magnitude (e.g. amplitude) of second pulses in the measurement signal, or smaller than a predetermined absolute limit, the timing information may be obtained based on the measurement signal, whereas the timing information otherwise is obtained based on the reference signal (or vice versa). Thus, with reference to FIG. 32, step 601 is adjusted based on the magnitude of second pulses.

In another example, if the magnitude (amplitude) of the second pulses in the reference signal again are found to be too small, the monitoring method may switch to another method for detecting presence or absence of second pulses in the measurement signal, e.g. a method that operates without timing information (e.g. by omitting steps 601, 602, 202 and 202' in FIG. 32).

In the above examples, if the magnitude of first and second pulses are covariant entities, the dynamic adjustment may alternatively be based on the magnitude of first pulses, or the magnitude of a combination of first and second pulses.

Monitoring Technique Based on Patient Data Records

When the second fluid containing system (S2 in FIG. 24) is a blood system of a patient, the monitoring method may be configured to access and use patient-specific information, i.e. existing data records for the patient, e.g. obtained in earlier treatments of the same patient. The patient-specific information may be stored in an internal memory of the surveillance device (25 in FIG. 24), on an external memory which is made accessible to the surveillance device, or on a patient card where the information is e.g. transmitted wirelessly to the surveillance device, e.g. by RFID (Radio Frequency IDentification). For example, the surveillance device may compare the filtered measurement signal, or a parameter derived therefrom, to the patient-specific information. If large differences are identified, a warning may be issued and/or the monitoring technique may be modified (or chosen according to a predetermined table). Furthermore, the patient-specific information may be used by the surveillance device to optimize the monitoring technique by e.g. determining personal threshold values for use in the foregoing algorithms/processes. The patient-specific information may also be used by the surveillance device to determine if an alternative monitoring technique or combinations of monitoring techniques should be used.

Use of Information from Regular Stops of First Pulse Generator

In one embodiment, the first pulse generator is regularly (intermittently or periodically) stopped, and the measurement signal and/or reference signal is analysed for determination of amplitude, frequency and phase of second pulses. This resulting information may then be used to achieve detection by the above-mentioned phase-locking technique.

Alternatively or additionally, if the magnitude (e.g. amplitude) of the second pulse(s) detected during such a stop is smaller than a certain limit (chosen with a margin for safe detection), an alert on "uncertain detection" may be issued. Alternatively, if the magnitude is smaller than another limit, the first pulse generator may be actively controlled to be stopped at specific time intervals, where the information obtained during each stop may be used to modify the monitoring technique. For example, the thus-obtained information may be used to change (or add) threshold values in the foregoing algorithms/processes, or to determine if an alternative monitoring technique or combinations of monitoring techniques should be used. In another example, if the thus-obtained information indicates the pulse rate of second pulses, a dedicated bandpass filter (e.g. centred on the thus-obtained pulse rate) may be operated on the measurement signal/filtered measurement signal/evaluation segment to further improve the input to the process for obtaining timing information (cf. step 602 in FIG. 29) and/or the process for obtaining the parameter value based on the measurement signal (cf. step 203/603 in FIGS. 25 and 32). In one embodiment, such a bandpass filter is applied if the rates of first and second pulses are found to differ by more than a certain limit, e.g. about 10%.

In another embodiment, the first pulse generator is selectively controlled so as to reduce the flow rate through the fluid arrangement. By reducing the flow rate, it is possible to accept a longer response time of the monitoring process to a fault condition, while such a longer response time may serve to improve the precision of the monitoring process in detecting fault conditions.

Monitoring of an Extracorporeal Blood Flow Circuit

In the following, for the purpose of illustration only, an implementation of the first and second inventive concepts for monitoring the integrity of a fluid connection is described in the context of extracorporeal blood treatment. The following example involves a combination with the above-mentioned beating detection method. This is only an example, and the monitoring process could be equally implemented without the beating detection method and/or in combination with any one of the other monitoring techniques discussed above.

It should also be understood that the following implementation of the first and second inventive concepts, as well as the beating detection method, is not limited to extracorporeal blood treatment, but is generally applicable for monitoring the integrity of a fluid connection between first and second fluid containing systems.

Figure 33:
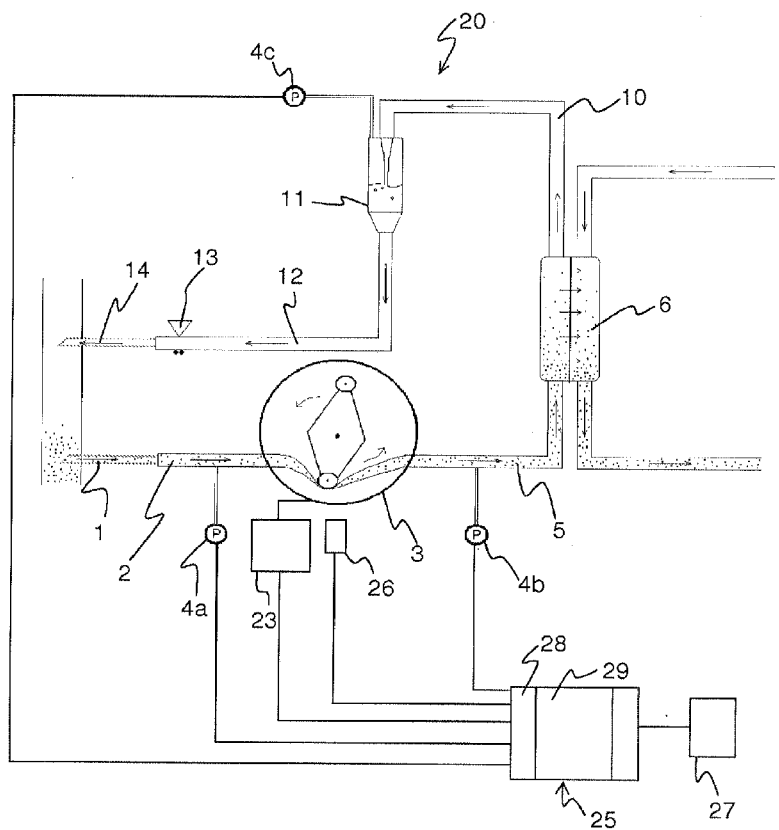
FIG. 33 is a schematic view of a system for hemodialysis treatment including an extracorporeal blood flow circuit.

FIG. 33 shows an example of an extracorporeal blood flow circuit 20 of the type which is used for dialysis. The extracorporeal blood flow circuit 20 comprises components 1-14 to be described in the following. Thus, the extracorporeal blood flow circuit 20 comprises an access device for blood extraction in the form of an arterial needle 1, and an arterial tube segment 2 which connects the arterial needle 1 to a blood pump 3 which may be of peristaltic type, as indicated in FIG. 33. At the inlet of the pump there is a pressure sensor 4a (hereafter referred to as arterial sensor) which measures the pressure before the pump in the arterial tube segment 2. The blood pump 3 forces the blood, via a tube segment 5, to the blood-side of a dialyser 6. Many dialysis machines are additionally provided with a pressure sensor 4b that measures the pressure between the blood pump 3 and the dialyser 6. The blood is lead via a tube segment 10 from the blood-side of the dialyser 6 to a venous drip chamber or deaeration chamber 11 and from there back to the patient via a venous tube segment 12 and an access device for blood reintroduction in the form of a venous needle 14. A pressure sensor 4c (hereafter referred to as venous sensor) is provided to measure the pressure on the venous side of the dialyser 6. In the illustrated example, the pressure sensor 4c measures the pressure in the venous drip chamber. Both the arterial needle 1 and the venous needle 14 are connected to the patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters.

As discussed by way of introduction, it may be vital to monitor the integrity of the fluid connection to the blood vessel access with respect to malfunction in the injection and/or extraction of blood therethrough. In many dialysis machines, one or more of said pressure detectors 4a-4c are not present. However, there will be at least one venous pressure sensor. The following description is focused on monitoring the integrity of the fluid connection between the blood vessel access and the venous needle based on a measurement signal from the venous pressure sensor. The monitoring process involves a so-called direct detection method, which may implement one of the first and second inventive concepts, and its different embodiments, as discussed above. Thus, in relation to the general arrangement in FIG. 24, the extracorporeal blood flow circuit 20 corresponds to the first fluid containing system S1, the blood pump 3 (as well as any further pulse source(s) within or associated with the extracorporeal blood flow circuit 20, such as a dialysis solution pump, valves, etc) corresponds to the first pulse generator 3, the blood system of the patient corresponds to the second fluid containing system S2, and the heart of the patient corresponds to the second pulse generator 3'.

In FIG. 33, a control unit 23 is provided, i.a., to control the blood flow in the circuit 20 by controlling the revolution speed of the blood pump 3. The extracorporeal blood flow circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

Further, in FIG. 33, a surveillance/monitoring device 25 is configured to monitor the integrity of the venous-side fluid connection between the patient and the extracorporeal blood flow circuit 20, specifically by monitoring the presence of a signal component originating from the patient's heart in a blood pressure signal. Absence of such a signal component is taken as an indication of a failure in the integrity of the fluid connection, and brings the device 25 to activate an alarm and/or stop the blood flow, e.g. by stopping the blood pump 3 and activating a clamping device 13 on tube segment 12. The surveillance device 25 is at least connected to receive a measurement signal of the pressure sensor 4c. The device 25 may also be connected to pressure sensors 4a, 4b, as well as any additional pressure sensors included in the extracorporeal blood flow circuit 20. As indicated in FIG. 33, the device 25 may also be connected to the control unit 23. Alternatively or additionally, the device 25 may be connected to a measurement device 26 for indicating the frequency and phase of the blood pump 3. The device 25 is tethered or wirelessly connected to a local or remote device 27 for generating an audible/visual/tactile alarm or warning signal. The surveillance device 25 and/or the alarm device 27 may alternatively be incorporated as part of a dialysis apparatus.

In FIG. 33, the surveillance device 25 comprises a data acquisition part 28 for pre-processing the incoming signal(s), e.g. including an A/D converter with a required minimum sampling rate and resolution, one or more signal amplifiers, one or more filters to remove undesired components of the incoming signal(s), such as offset, high frequency noise and supply voltage disturbances.

In the examples given herein, the data acquisition part 28 comprises a DAQ card USB-6210 from National Instruments with a sampling rate of 1 kHz and resolution of 16 bits, an operation amplifying circuit AD620 from Analog Devices, a high-pass filter with a cut-off frequency of 0.03 Hz (i.a., for removal of signal offset) together with a low-pass filter with a cut-off frequency of 402 Hz (i.a., for removal of high frequency noise). To obtain a short convergence time, a low-order filter is used for the high-pass filter. Furthermore, the data acquisition part 28 may include an additional fixed band-pass filter with upper and lower cut-off frequencies of 0.5 Hz and 2.7 Hz, respectively, which corresponds to heart pulse rates between 30 and 160 beats per minute. This filter may be used to suppress disturbances outside the frequency interval of interest.

After the pre-processing in the data acquisition part 28, the signal from the pressure sensor 4c is provided as input to a data analysis part 29, which executes the actual monitoring process. FIG. 34(a) shows an example of such a pre-processed pressure signal in the time domain, and FIG. 34(b) shows the corresponding power spectrum, i.e. the pressure signal in the frequency domain. The power spectrum reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics $2 f_0$, $3 f_0$ and $4 f_0$. The base frequency, also denoted pumping frequency in the following, is the frequency of the pump strokes that generate pressure waves in the extracorporeal blood flow circuit. For example, in a peristaltic pump of the type shown in FIG. 33, two pump strokes are generated for each full revolution of the rotor. FIG. 34(b) also indicates the presence of a frequency component at half the pumping frequency (0.50 and harmonics thereof, in this example at least $f_0$, $1.5 f_0$, $2 f_0$ and $2.5 f_0$. FIG. 34(b) also shows a heart signal (at 1.1 Hz) which in this example is approximately 40 times weaker than the blood pump signal at the base frequency $f_0$.

Figure 36:
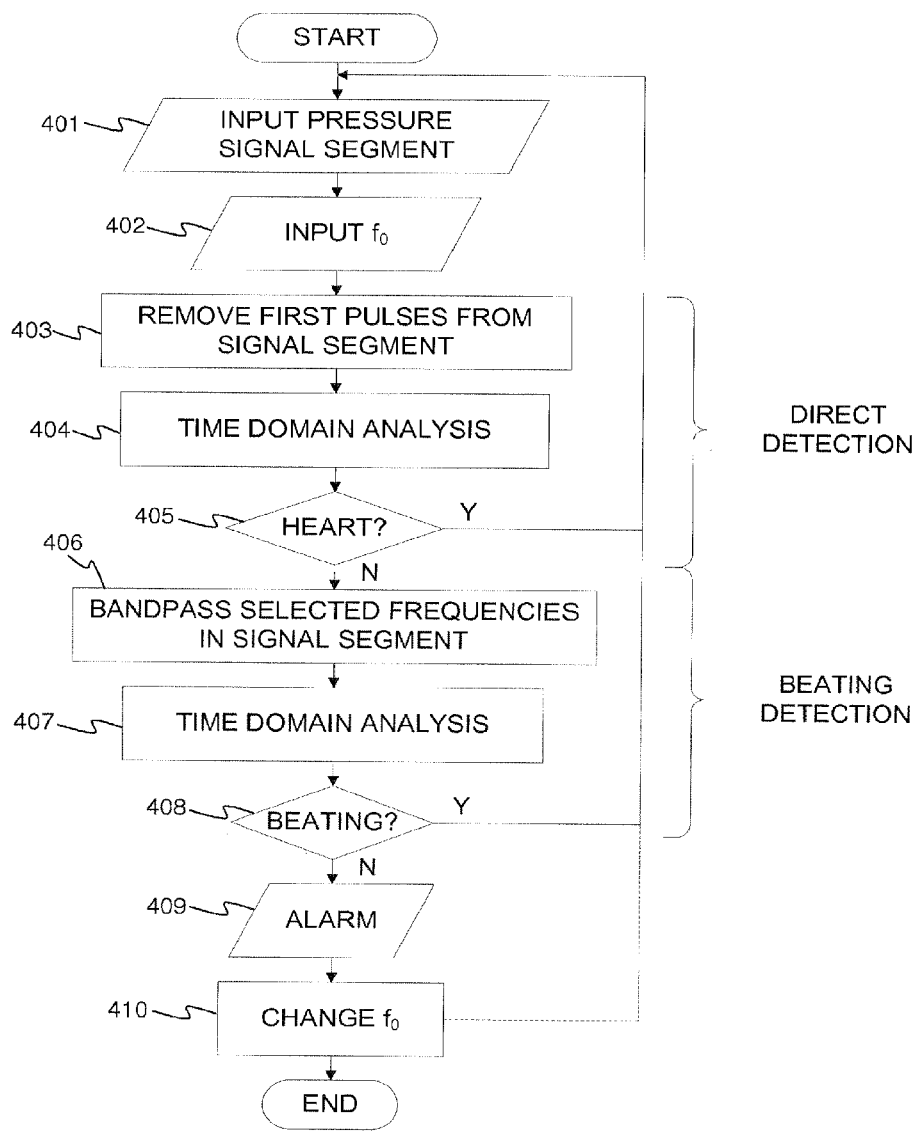
FIG. 36 is a flow chart of an exemplifying monitoring process.
Figure 37:
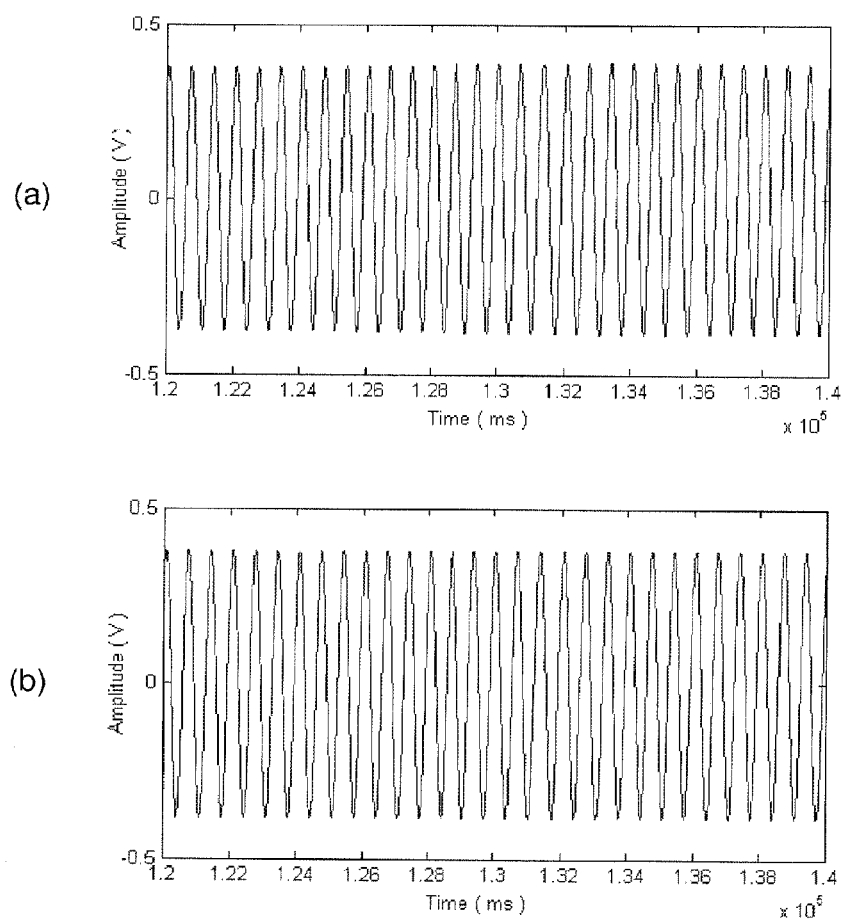
FIGS. 37(*a*) and 37(*b*) are plots in the time domain of a pressure signal after processing in a beating detection module in the data analyser of FIG. 35, with and without a heart signal.
Figure 38:
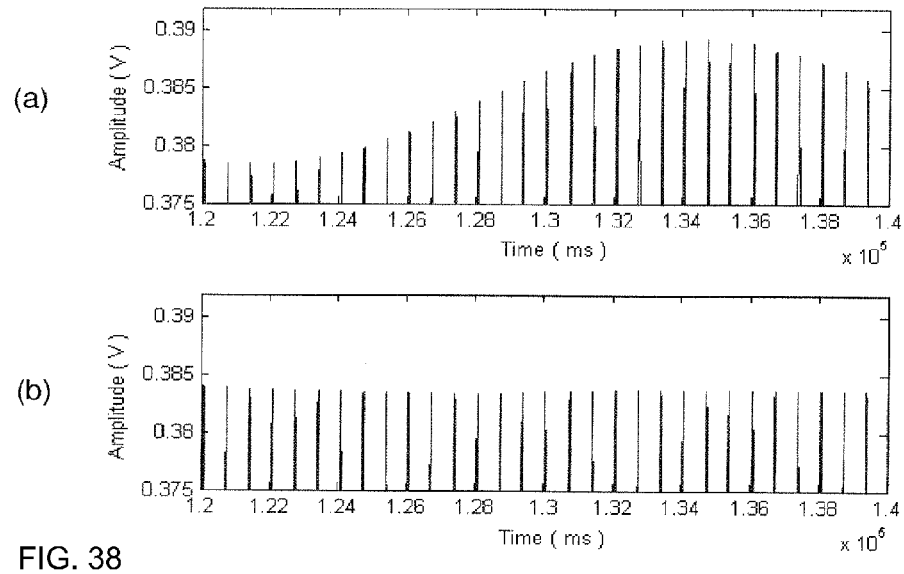
FIGS. 38(*a*) and 38(*b*) are enlarged view of the plots in FIGS. 37(*a*) and 37(*b*).

FIG. 36 is a flow chart for a data analysis or monitoring process according to an embodiment of the present invention. The illustrated process implements a combination of detection methods to monitor the integrity of the fluid connection between the extracorporeal blood flow circuit 20 and the blood system of a human. One detection method ("direct detection") involves using a time domain analysis for detecting a heart pulse in the pressure signal. Another detection method ("beating detection") involves detecting an amplitude modulation (beating signal) in the pressure signal, the amplitude modulation being caused by interference between pressure waves originating from the patient's heart and the blood pump. These detection methods will be described in further detail below, but first the overall operation of the process will be briefly outlined.

The monitoring process starts by inputting a signal segment of the pressure signal (step 401), as well as information on the base frequency ($f_0$) of the blood pump (step 402).

This frequency information may be obtained from processing of the pressure signal itself. Alternatively, it may be obtained from a signal generated by a dedicated measurement device (cf. 26 in FIG. 33), or from a signal indicative of a set value or actual value used by the control unit (cf. 23 in FIG. 33). It is to be understood that step 402 need not be executed for every iteration of the monitoring process.

Figure 34:
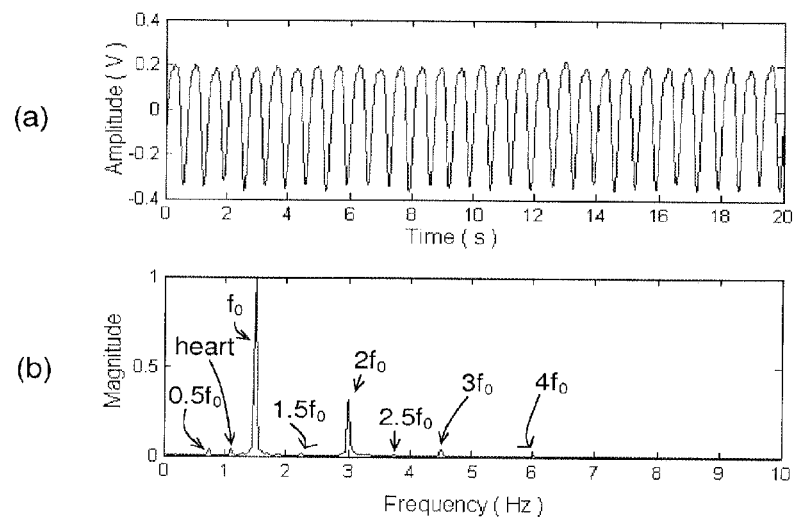
FIG. 34(*a*) is a plot in the time domain of a venous pressure signal containing both pump frequency components and a heart signal, and FIG. 34(*b*) is a plot of the corresponding signal in the frequency domain.

The direct detection method involves steps 403-405, in which the signal segment is processed so as to remove first pulses originating from the blood pump, e.g. by blocking one or more of the frequency components (see 0.5 $f_0$, $f_0$, 1.5 $f_0$, 2 $f_0$, 2.5 $f_0$, 3 $f_0$ and 4 $f_0$ in FIG. 34) related to the blood pump. Typically, step 403 (corresponding to step 202 in FIG. 25) is designed to effectively "clean" the signal segment from all frequency components emanating from the blood pump. In step 404 (corresponding to step 203 in FIG. 25), the signal segment is analysed in the time domain to identify any remaining signal pulse emanating from the patient's heart. If such a heart pulse is detected in step 405 (corresponding to step 204 in FIG. 25), the monitoring is returned to step 401, in which a new pressure signal segment is inputted for processing. As mentioned above, this new signal segment may or may not partially overlap the preceding signal segment. If no heart component is detected in step 405, the monitoring proceeds to beating detection. The lack of a heart pulse may result from a malfunction of the venous-side fluid connection, e.g. by the venous needle detaching from the blood vessel access, or by the heart pulse being too weak to be detected. Alternatively, the heart beat frequency may essentially coincide with any of the frequency components of the blood pump, causing the heart pulse to be accidentally eliminated in the filtering step 403.

In an alternative implementation, the direct detection method steps 403-405 correspond to steps 602-604 according to the second inventive concept discussed above in relation to FIG. 29.

In either implementation, the direct detection method may utilize timing information, which may be obtained as described above in relation to the second inventive concept.

The beating detection method involves steps 406-408, in which the signal segment is processed so as to identify a beating signal caused by interference between pressure waves originating from the heart and the blood pump, respectively. The beating signal is perceived as periodic variations in signal amplitude with a frequency equal to the difference in frequency between these two pressure waves. Thus, instead of searching for the heart pulse itself in the pressure signal, the beating detection looks at indirect effects of the heart pulse on the pressure signal in the time domain.

In step 406, the signal segment is processed to remove all frequencies except for one or more selected frequency bands. Each such selected frequency band is a band surrounding only one of the frequency components (see 0.5 $f_0$, $f_0$, 1.5 $f_0$, 2 $f_0$, 2.5 $f_0$, 3 $f_0$ and 4 $f_0$ in FIG. 34) related to the blood pump. This selective bandpass filtering may be effected to facilitate the detection of the beating signal. The pressure wave from the heart is generally much smaller (typically 20-200 times) than the pressure wave from the blood pump, so a potential beating wave will be weak and possibly difficult to detect. Typically, all frequencies outside one such selected frequency band are removed from the signal segment, whereupon the resulting filtered signal segment is analysed in the time domain for detection of a beating signal (step 407). If the blood pump is known to produce a number of frequency components (as shown in FIG. 34), step 406 results in a set of filtered signal segments, each including only frequencies around one of these frequency components. These filtered signal segments may be generated in parallel and then analysed in step 407. Alternatively, filtered signal segments may be generated in sequence, based on a given order of blood pump frequency components. Each filtered signal segment may be passed on to step 407 for analysis before another filtered signal segment is generated, such that the generating of filtered signal segments is interrupted as soon as a beating signal is detected.

In yet another embodiment, the heart pulse rate is known. In such a situation, step 406 may be limited to generating only one filtered signal segment, which includes only frequencies around the frequency component that lies closest to the known heart frequency. The heart pulse rate is suitably obtained in similar way as the timing information.

The selective bandpass filtering of step 406 may use a fixed width of the frequency band(s), which is set in view of a desired performance of the beating detection method, typically the maximum frequency spacing between a heart pulse and a pump frequency component that should result in a beating signal. For example, the frequency bands used by the beating detection method may be small compared to the spacing of the pump frequency components, if the beating detection method is used in combination with another detection method (e.g. the direct detection method) which is capable of detecting presence/absence of a heart signal in specific frequency regions in between these frequency components. In other situations, the frequency bands may have about the same total width as the spacing of the pump frequency components, or the frequency bands of adjacent pump frequency components may even overlap. In another embodiment, the width of the frequency band(s) may be adaptively set as a function of a previously determined heart frequency. For example, the width may be reduced as the heart frequency approaches one of the pump frequency components. As mentioned above, the heart frequency may e.g. be obtained from a separate pulse rate meter, another pressure sensor, or in a preceding iteration of the monitoring process.

However, it is to be understood that the selective bandpass filtering around different frequency components of the blood pump is included to facilitate beating detection, but may be dispensed with.

If a beating signal is detected in step 408, the monitoring is returned to step 401, in which a new pressure signal segment is inputted for processing. If no beating signal is detected in step 408, the monitoring proceeds to activate an alarm that indicates a malfunction, or at least a warning that such a malfunction may have occurred (step 409). Concurrently with activating the alarm/warning, the process may proceed to step 410 in which the pumping frequency is changed, whereupon the monitoring process may return to step 401 to continue to monitor the integrity of the fluid connection between the blood vessel access and the venous needle. If a heart component/beating signal is discovered during subsequent iteration(s) of the monitoring process, the alarm/warning may be shut off. Alternatively, to minimize the number of false alarms, the alarm/warning may be activated only if the monitoring process fails to detect the heart signal both before and after such a change in pumping frequency.

In one embodiment of step 410, the pump is kept operative, but its pumping frequency is changed. In one variant, the pumping frequency is lowered in order to reduce the blood flow and thereby minimize any blood loss caused by the potential malfunction that has been detected. In another variant, the pumping frequency is actively shifted such that its frequency components are non-coincident with its previous frequency components. For example, the base frequency could be shifted by a fraction of the spacing between the frequency components originating from the pump. In the example of FIG. 34, this would mean a fraction of 0.5 $f_0$. Typically, the shift represents a reduction in the pumping frequency.

In another embodiment of step 410, the pump is shutdown (i.e. $f_0=0$) to remove the interference from the blood pump while also minimizing any blood loss caused by the potential malfunction that has been detected. In a variant of such an embodiment, step 410 also involves identifying the frequency of the heart while the blood pump is shut-down, and then re-starting the blood pump with a pumping frequency shifted from the thus-identified heart frequency. The heart frequency may be identified from the pressure signal, e.g. using the spectral signal analysis of step 404.

Figure 35:
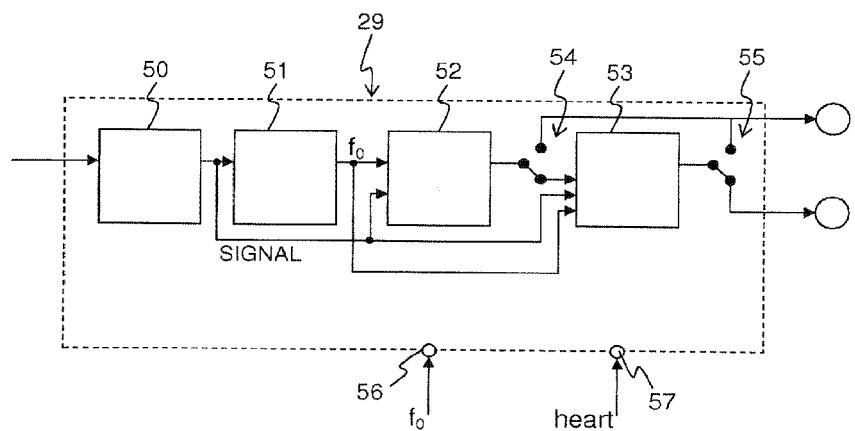
FIG. 35 is a block diagram of a data analyser for executing the process of FIG. 36.

FIG. 35 is a block diagram of the data analysis part (cf. 29 in FIG. 33) which is configured to carry out the monitoring process shown in FIG. 36. In the illustrated embodiment, the data analysis part includes a storage block 50, a pump frequency determination block 51, a direct detection block 52, a beating detection block 53, and switching blocks 54, 55 for connecting the output of the direct detection block 52 and the beating detection block 53 to an alarm device. Although not shown, a control block may be provided to synchronize the operation of the blocks 50-55.

The data analysis part 29 may be implemented by software running on a processing device, such as a general- or special-purpose computer device or a programmed microprocessor. The storage block 50 may be a volatile or non-volatile memory of such a computer device, whereas the other blocks 51-55 may be implemented by software instructions. However, it is conceivable that some or all blocks are fully or partially implemented by dedicated hardware, such as an FPGA, an ASIC, or an assembly of discrete electronic components (resistors, capacitors, operational amplifier, transistors, etc), as is well-known in the art.

The storage block 50 is operated to store the incoming pressure signal as a sequence of data samples. The other blocks 51-53 are then operated to receive or retrieve segments of the stored pressure signal from the storage block 50. The storage block 50 thus buffers the incoming pressure signal, allowing overlapping or non-overlapping signal segments to be individually processed and analysed. The storage block 50 may, e.g., be implemented as a plurality of linear buffers or as a circular buffer.

Block 51 is configured to determine the frequency of the blood pump based on a signal segment. An example of an algorithm used by such a block will be further described below.

Block 52 implements the direct detection steps 403-405 (FIG. 36), based on an estimated pumping frequency provided by the pump frequency determination block 51. If the outcome of the determination step 405 is negative, i.e. no heart component is found, switching block 54 is operated to activate block 53. If a heart component is found, switching block 54 may be operated to provide a positive status indication to the alarm device, and a new signal segment may be received or retrieved by blocks 51, 52.

Block 53 implements the beating detection steps 406-408 (FIG. 36), again based on the estimated pumping frequency. If the outcome of determination step 408 is negative, i.e. no beating signal is detected, switching block 55 is operated to provide a negative status indication to the alarm device, which issues an alarm. If a beating signal is found, switching block 55 may be operated to provide a positive status indication to the alarm device, and a new signal segment may be received or retrieved by the blocks 51, 52.

In FIG. 35, the data analysis part also includes an input 56 for receiving a signal indicative of the pumping frequency (e.g. from the measurement device 26 or the control unit 23 in FIG. 33). As discussed in relation to step 410 (FIG. 36), frequency information obtained from this signal may supplement or replace the frequency determined by block 51.

FIG. 35 also indicates the provision of an input 57 for a measurement signal indicative of the patient's heart frequency, e.g. to provide timing information to block 52 or to be used by block 53 when executing step 406.

An exemplifying operation for each of the blocks 51-53 will now be described, starting with the pump frequency determination block 51.

The pump frequency determination block 51 is configured to calculate a power spectrum from a pressure signal segment, and identify the base pumping frequency in the power spectrum. The power spectrum can be calculated in any known way, e.g. by operating a DFT (Discrete Fourier Transform) or an FFT (Fast Fourier Transform) on the pressure signal segment. The base pumping frequency may be identified as the frequency of the largest peak in the power spectrum, or at least among one of the largest peaks.

If the resolution of the power spectrum is low, special measures may be employed to increase the accuracy of the estimated frequency. The resolution is dependent on the sampling frequency $f_s$ and the number of samples N in the signal segment as $f_s/N$. In one example, signal segments of 20 seconds are sampled at 10 Hz, with a resolution of 0.05 Hz. This accuracy may be inadequate for the processing in the direct detection block 52 and/or beating detection block 53. To increase the accuracy, the signal segment may be bandpass filtered in a narrow range around the estimated frequency obtained from the power spectrum, resulting in a comparatively noiseless and sinusoid-like signal segment. A precise estimation of the base frequency can then be obtained by determining the period of the filtered signal segment in the time domain, e.g. by adapting a sinusoid to the filtered signal and identifying the time difference between zero-crossings.

The direct detection block 52 may comprise components for cancelling the signal pulses that emanate from the blood pump, and any further interfering pulse sources (i.e. the "first pulses" discussed above in relation to the first and second inventive concepts). Furthermore, the direct detection block 52 may comprise components that obtain the aforesaid timing information, as well as components that carry out the time domain analysis according to the first and/or second aspects for identification of heart pulses in the pressure signal.

The beating detection block 53 is configured to filter the signal segment with respect to a set of passbands, each containing one frequency component of the blood pump. Each resulting filtered signal segment is essentially a sinusoid. If the frequency of the heart lies within one of these passbands, then the corresponding filtered signal segment will have a waveform not to be found in any of the other filtered signal segments.

FIG. 37(a) shows a 20 second signal segment which has been filtered with a narrow bandpass surrounding the base frequency of the blood pump at 1.5029 Hz. The filtered signal also contains a heart pulse, which has a frequency shift of 0.037 Hz with respect to the base frequency. The relative magnitude between the blood pump and heart pulse is 40:1. FIG. 37(b) shows a corresponding filtered signal segment without a heart signal. Although being very small, it is possible to distinguish a difference between the signal segments, where the presence of the heart causes an overlying variation in signal amplitude in FIG. 37(a) which is lacking in FIG. 37(b). FIGS. 38(a) and 38(b) are enlarged views of the signal peaks in FIGS. 37(a) and 37(b), respectively, showing a clear difference between the filtered signal segments with and without a heart pulse.

In one embodiment, the beating detection block 53 is configured to detect the beating signal based on an envelope obtained from the filtered signal segment.

Figure 39:
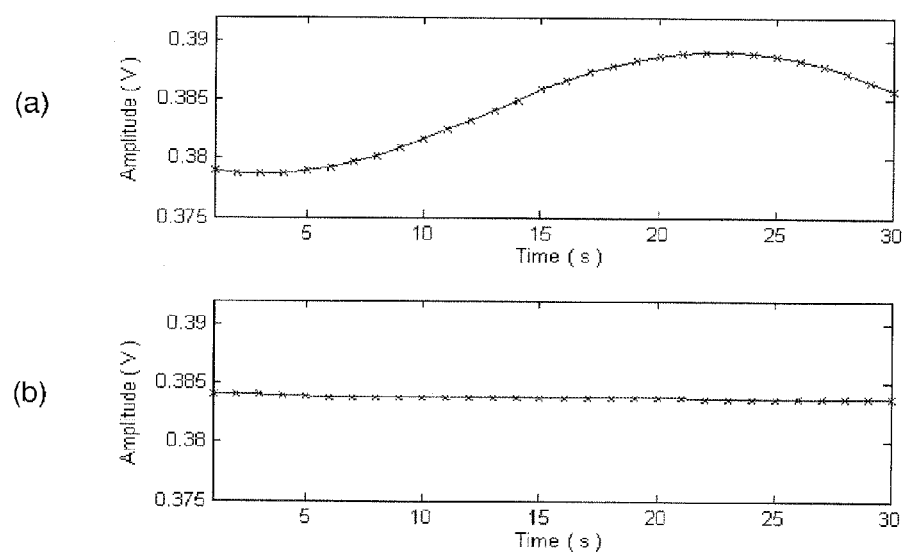
FIGS. 39(*a*) and 39(*b*) are plots of envelopes extracted from the data in FIGS. 38(*a*) and 38(*b*).

In one such variant, the beating detection block 53 obtains the envelope by extracting an array of peak values from the signal segment. The extracted peak values may be given by extracting signal values of individual peaks identified in the signal segment. To improve noise robustness, each extracted peak value may instead be calculated as an average or sum of the signal values forming each peak in the signal segment, e.g. including signal values within 10-25% of the peak value or within a given time range around the peak value. The obtained envelope (peak value array) is then processed for calculation of an evaluation parameter. FIGS. 39(*a*) and 39(*b*) show peak value arrays extracted from FIGS. 38(*a*) and 38(*b*), respectively.

In another variant, block 53 obtains the envelope by applying a linear, time-invariant filter known as a Hilbert transformer to the signal segment x. This operation results in a transformed signal segment x̌, which is a 90° phase-shifted version of the signal segment. The envelope b(n) can then be obtained from $$b(n) = \sqrt{x^2(n) + \check{x}^2(n)},$$

with n being the different positions in the signal segment.

For improved processing efficiency, block 53 may obtain an approximate envelope b̂(n) from the signal segment x based on the relation $$\hat{b}(n) = |x(n)| + \frac{2}{\pi}|x(n+1) - x(n-1)|.$$

The obtained envelope, be it approximate or not, is then processed for calculation of an evaluation parameter.

In either variant, the obtained envelope may be low-pass filtered to further remove envelope noise, before being processed for calculation of the evaluation parameter.

In either variant, the resulting value of the evaluation parameter may be compared to a threshold value for determining presence or absence of a beating signal.

In one example, the evaluation parameter is the absolute sum of derivatives of the values of the envelope, given by:

$$\sum_{n=0}^{N-1} |(b(n+1) - b(n))|$$

with b(n) being the envelope value at position n, and N being the number of values in the envelope.

Figure 40:
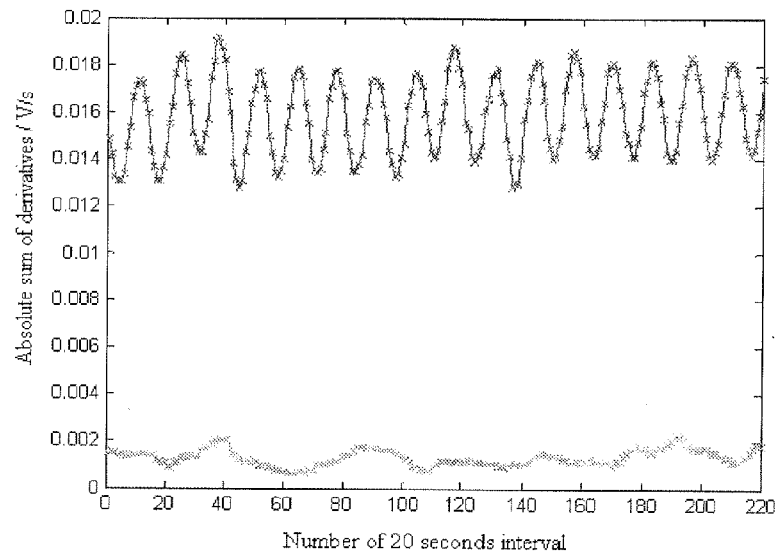
FIG. 40 is a plot of the sum of derivatives as a function of time, calculated from envelopes with and without a heart signal.

FIG. 40 illustrates a result of moving a 20 second window over a 5 minute pressure signal, one second at the time, and calculating the absolute sum of derivatives on an envelope obtained for each 20-second signal segment. The upper curve is calculated for filtered signal segments containing a heart signal, and the lower curve is calculated for filtered signal segments without a heart signal. Clearly, a threshold value can be defined to distinguish between the presence and absence of a heart signal.

The upper curve exhibits a waveform due to the fact that the signal segment contains part of a full beating signal period. Thus, over time, the signal segments will contain different parts of the beating signal. Since the gradient is small around the peaks and valleys of the envelope and larger therebetween, the calculated sum of derivatives will vary correspondingly over time. It should be realized that, for a given length (time window) of the signal segment, the detectability of the gradients will decrease with decreasing frequency difference between heart and blood pump, since this lowers the beating frequency and flattens the envelope. A wider time window will improve the detectability until the point where the amplitude of the beating becomes smaller than the noise.

Figure 41:
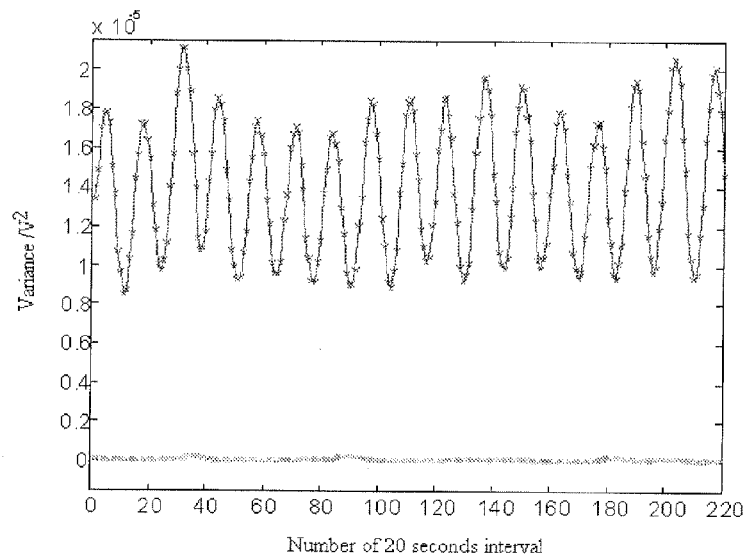
FIG. 41 is a plot of variance as a function of time, calculated from envelopes with and without a heart signal.

In another example, the evaluation parameter is the variance of the values of the envelope. FIG. 41 is a plot corresponding to FIG. 40, but illustrating the variance as a function of time, with (upper) and without (lower) a heart signal. Clearly, a threshold value can be defined to distinguish between the presence and absence of a heart signal.

In yet another example, which may reduce influence of envelope noise, the evaluation parameter is an averaged sum of derivatives, e.g. given by $$\sum_{n=1}^{N-1} \left| \frac{(b(n+1) - b(n-1))}{2} \right|.$$

In another embodiment, the beating detection block 53 determines the presence or absence of a beating signal based on pattern recognition processing. For example, all or part of the signal segment or the envelope may be matched against one or more predetermined signal patterns that are representative of a beating signal. In one example, the obtained envelope (optionally low-pass filtered) may be cross-correlated or otherwise convolved with each of a set of sinus waves of different frequencies. Each cross-correlation/convolution results in a correlation curve, from which a maximum correlation value can be obtained. The resulting set of maximum correlation values may then be compared to a threshold value for determining presence/absence of a beating signal, where a high enough maximum correlation value may be taken as an indication of such presence.

In an alternative implementation, the beating detection block 53 operates on signal segments that are long in relation to the period of the beating signal, and processes these signal segments to detect the beating signal in the frequency domain, e.g. by operating a Fourier transformation on the envelope.

All of the above examples of determining presence of a beating signal may involve the further step of assessing the reliability of the determined beating signal. This assessment may involve determining the beating frequency of the beating signal and checking if this beating frequency is reasonable. Depending on how the beating signal is identified, the beating frequency may be determined by processing the obtained envelope in the time/frequency domain, or by identifying the frequency of the sinus wave that yields the maximum correlation value. The beating frequency may be checked in absolute terms and/or in relation to one or more beating frequencies determined in preceding iterations of the monitoring process (FIG. 36), where large enough deviations from the preceding beating frequency/frequencies may be taken as an indication that the determined beating signal is unreliable. The assessment may result in a reliability score that indicates the reliability of the determined beating signal. Alternatively or additionally, the reliability assessment may include the step of controlling the pump to change its pumping frequency and checking if a corresponding change occurs in the beating signal. For example, the pumping frequency may be shifted slightly, or the pump may be intermittently shut-down. The outcome of the reliability assessment may affect the execution of steps 409-410, e.g. whether an alarm/warning is activated, whether further iterations of the monitoring process is required before activating the alarm/warning, whether the pumping frequency is to be changed, etc.

Tests have shown that different evaluation parameters may be preferable in different situations. For example, the use of variance may increase the detectability when looking for a beating signal around one of the harmonics, whereas the use of absolute sum of derivatives or averaged sum of derivatives may be better when looking for a beating signal around the base frequency. Pattern recognition may be resorted to when other detection methods fail. Thus, the beating detection block 53 may be configured to use one or any combination of these evaluation parameters.

Figure 42:
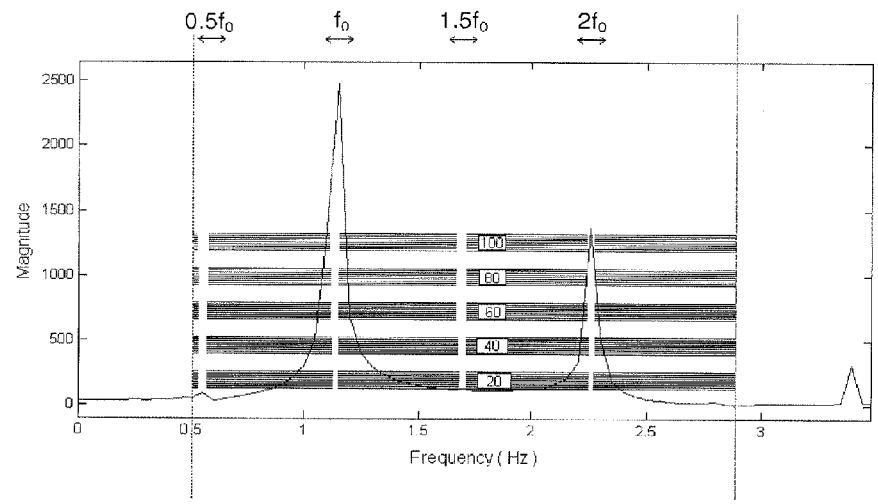
FIG. 42 is a diagram illustrating the performance of a beating detection module, for different relative magnitudes between the blood pulse and the heart pulse.

FIG. 42 is an example of frequency and amplitude ranges in which a heart pulse is detectable using the beating detection block 53. The dotted lines indicate the frequency range of a normal heart, and the dark horizontal bands indicate the frequencies at which a heart pulse could be detected in a system using a pumping frequency of 1.13 Hz. The five rows of horizontal bands represent different relative magnitudes between the blood pump and heart pulses, ranging from 20:1, 40:1, 60:1, 80:1 and 100:1 from the bottom row to the top row.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

For example, the pressure signal may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, etc.

Further, the illustrated embodiments are applicable for surveillance of all types of extracorporeal blood flow circuits in which blood is taken from a patient's circulation to have a process applied to it before it is returned to the circulation. Such blood flow circuits include hemodialysis, hemofiltration, hemodiafiltration, plasmapheresis, apheresis, extracorporeal membrane oxygenation, assisted blood circulation, and extracorporeal liver support/dialysis.

Further, the inventive monitoring techniques are applicable to any type of pumping device that generates pressure pulses in the first fluid containing system, not only rotary peristaltic pumps as disclosed above, but also other types of positive displacement pumps, such as linear peristaltic pumps, diaphragm pumps, as well as centrifugal pumps.

Still further, the inventive monitoring techniques are applicable also for monitoring the integrity of the fluid connection between the blood vessel access and the arterial needle based on a measurement signal from one or more arterial pressure sensors. Such a monitoring technique may provide a faster detection of malfunction than the conventional air detector, and more reliable detection of malfunction than conventional comparison of average pressure levels to threshold values. In such an application, the aforesaid reference signal may be derived from one or more venous pressure sensors in the extracorporeal blood flow circuit.

Also, it is to be understood that the monitoring technique is equally applicable to single-needle dialysis.

The inventive monitoring techniques are also applicable when the measurement signal originates from a pressure sensor arranged to sense the pressure in the human blood system. In such an embodiment, the first fluid containing system (S1) is the human blood system, the second fluid containing system (S2) is the extracorporeal blood flow circuit, and the fluid connection (C) may be formed by a connection between an access device and a blood vessel access. The first pulses thus originate from the human heart, and the second pulses originate from the pumping device in the extracorporeal blood flow circuit (and/or any other pulse generator within or associated with the extracorporeal blood flow circuit), and the integrity of the fluid connection is determined by applying the first and/or second inventive concepts to detect the presence/absence of the second pulses in the measurement signal.

Figure 43:
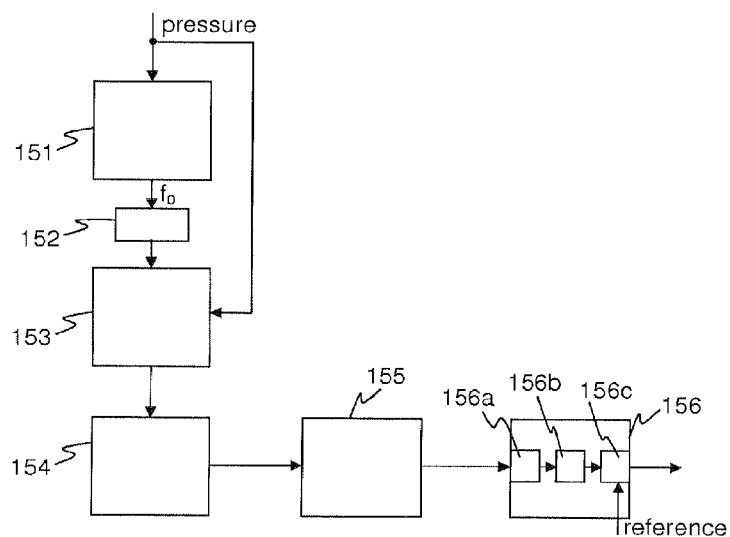
FIG. 43 is a schematic view of an arrangement of analog devices for detection of a beating component in a pressure signal.

Furthermore, the monitoring process is not limited to digital signal processing. FIG. 43 illustrates an exemplary combination of analog devices for detection of a beating component in a pressure signal. The individual devices are known per se, and alternative implementations are readily available to the skilled person. The exemplary combination of analog devices includes a bandpass filter 151 which is adapted to filter an incoming pressure signal to isolate a signal component at the base frequency ($f_0$) of the pumping device. A frequency multiplier 152 is arranged to receive the filtered pressure signal and is controllable to generate a corresponding output signal at a selected multiple (0.5, 1, 2.5, 3 etc) of the base frequency. The output signal from the multiplier 152 is input as a control signal to a controllable bandpass filter 153, which is adapted to receive and filter the incoming pressure signal. The filter 153 is thereby controlled to process the pressure signal by removing all frequencies except for a frequency band around the frequency of the control signal from the multiplier 152 (cf. step 406 in FIG. 36). The processed pressure signal is input to a peak detector 154 which thereby generates an envelope signal, which in turn is fed to a high-pass filter 155 which removes any DC component from the envelope signal. Optionally, a low-pass filter (not shown) may be included to remove high-frequency noise from the envelope signal. Finally, the envelope signal is received by an amplitude detector 156 which is adapted to determine presence/absence of a beating signal. The amplitude detector may include, in sequence, a full wave rectifier 156a, a low-pass filter 156b and a comparator 156c which is fed with a reference signal. If the amplitude of the input signal to the comparator 156c exceeds the reference signal, the comparator 156c may output a signal indicating presence of a beating signal, otherwise not, or vice versa.

The above-described inventive concepts may also be applicable to monitoring the integrity of fluid connections for transferring other liquids than blood. Likewise, the fluid connections need not be provided in relation to a human, but could be provided in relation to any other type of fluid containing system.

In one example, the fluid connection is provided between a blood processing circuit and a container/machine, wherein blood is pumped from one container/machine through a blood processing device in the blood processing circuit and back to the container/machine, or to another container/machine downstream of the blood processing device. The blood processing device could be any known device configured to modify and/or analyse the blood.

In a further example, the fluid connection is provided between a dialyser and a reprocessing system, which reprocesses the dialyser by pumping water, optionally together with suitable chemicals through the dialyser. An example of a dialyser reprocessing system is known from US2005/0051472.

In another example, the fluid connection is provided between a dialysate supply and a dialysate regeneration system, which circulates dialysate from the dialysate supply through a dialysate regeneration device and back to the supply. An example of a dialysate regeneration device is known from WO 05/062973.

In yet another example, the fluid connection is provided in an arrangement for priming an extracorporeal blood flow circuit by pumping a priming fluid from a supply via the blood flow circuit to a dialyser. The priming fluid may e.g. be dialysis solution, saline, purified water, etc.

In a still further example, the fluid connection is provided in an arrangement for cleaning and disinfecting the dialysis solution flow path of a dialysis machine, which pumps a cleaning fluid via a flow path to a dialyser/dialyser tubing. The cleaning fluid may e.g. be hot water, a chemical solution, etc.

In a further example, the fluid connection is provided in an arrangement for purifying water, which pumps water from a supply through a purifying device. The purifying device may use any known water purification technique, e.g. reverse osmosis, deionization or carbon absorption.

In another example, the fluid connection is provided in an arrangement for providing purified water to a dialysis machine, e.g. to be used in the preparation of dialysis solution therein.

In all of these examples, and in other applications related to medical treatment of human or animal patients, it may be vital to monitor the integrity of the fluid connection. Such monitoring can be accomplished according to the inventive concepts disclosed herein.

The invention claimed is:

1. A device for monitoring the integrity of a fluid connection between an extracorporeal fluid system and a vascular system of a subject having a natural breathing system, said system comprising:
    a mechanical pulse generator configured to generate a first pulse;
    a pressure sensor configured to sense the first pulse and a second pulse originating from the natural breathing system, and output a measurement signal;
    a signal processor; and
    a memory device storing a plurality of instructions, which when executed by the signal processor, cause the signal processor to:
    (i) analyze the measurement signal to isolate the first pulse and the second pulse;
    (ii) monitor whether the second pulse remains present in the measurement signal, and
    (iii) when the second pulse originating from the natural breathing system is not present in the measurement signal, send a signal causing at least one of: (a) an alarm device to activate an alarm, (b) a blood pump to stop, or (c) a valve to close.

2. The device of claim 1,
    wherein said measurement signal is a time-dependent monitoring signal, and
    wherein said memory device further stores instructions which, when executed by the signal processor, cause the signal processor to calculate a parameter value based on signal values within a time window in the time-dependent monitoring signal, the parameter value representing a distribution of the signal values, and monitor the integrity of the fluid connection based at least partly on the parameter value.

3. The device of claim 2 wherein said memory device further stores instructions which, when executed by the signal processor, cause the signal processor to calculate the parameter value by performing at least one of:
    calculating the parameter value as a statistical dispersion measure of the signal values within the time window;
    matching the signal values within the time window to a predicted temporal signal profile of the second pulse; and
    identifying a candidate second pulse in the time-dependent monitoring signal and a corresponding candidate time point, and validating the candidate second pulse based on the candidate time point in relation to timing information indicative of the timing of the second pulses in the time-dependent monitoring signal.

4. The device of claim 1 wherein said measurement signal is a time-dependent monitoring signal, and said memory device further stores instructions which, when executed by the signal processor, cause the signal processor to:
    obtain timing information indicative of the timing of the second pulses in the time-dependent monitoring signal;
    process the time-dependent monitoring signal based on the timing information;
    calculate a parameter value indicative of presence or absence of the second pulses; and
    monitor the integrity of the fluid connection based at least partly on the parameter value.

5. The device of claim 1 wherein said signal processor is not configured to process the measurement signal for identification of heart data originating from heart beats of said subject, and monitor the integrity of the fluid connection based on said heart data.

6. The device of claim 1 wherein said memory device further stores instructions which, when executed by the signal processor, cause the signal processor to process the measurement signal to isolate the second pulses originating from the breathing system of said subject from pluses originating from other physiological phenomena.

7. The device of claim 6 wherein said other physiological phenomenon is a repetitive physiological pulse generator.

8. The device of claim 1 wherein said memory device further stores instructions which, when executed by the signal processor, cause the signal processor to filter the measurement signal in the frequency domain.

9. The device of claim 1 wherein said memory device further stores instructions which, when executed by the signal processor, cause the signal processor to perform at least one of: low-pass filtering the measurement signal to remove frequencies below about 0.5 Hz, and high-pass filtering the measurement signal to remove frequencies above about 3.5 Hz.

10. The device of claim 9 wherein said memory device further stores instructions which, when executed by the signal processor, cause the signal processor to band-pass filter the measurement signal with respect to at least one frequency range included in the group consisting of 0.15 Hz to 0.4 Hz, 0.04 Hz to 0.15 Hz, and 0.001 Hz to 0.1 Hz.

* * * * *